US009073984B2

(12) United States Patent
Brophy et al.

(10) Patent No.: US 9,073,984 B2
(45) Date of Patent: Jul. 7, 2015

(54) ANTI-*T. CRUZI* ANTIBODIES AND METHODS OF USE

(75) Inventors: Susan E. Brophy, Lindenhurst, IL (US);
David J. Hawksworth, Lake Villa, IL (US); Dinesh O. Shah, Libertyville, IL (US); Robert W. Siegel, Fountaintown, IN (US); Bryan C. Tieman, Elmhurst, IL (US); Bailin Tu, Libertyville, IL (US); Joan D. Tyner, Beach Park, IL (US); Robert N. Ziemann, Lindenhurst, IL (US)

(73) Assignee: ABBOTT LABORATORIES, Abbott Park, IL (US)

( * ) Notice: Subject to any disclaimer, the term of this patent is extended or adjusted under 35 U.S.C. 154(b) by 0 days.

(21) Appl. No.: 13/353,678

(22) Filed: Jan. 19, 2012

(65) Prior Publication Data
US 2012/0122125 A1 May 17, 2012

Related U.S. Application Data

(63) Continuation of application No. 12/342,641, filed on Dec. 23, 2008, now abandoned.

(60) Provisional application No. 61/017,071, filed on Dec. 27, 2007.

(51) Int. Cl.
*G01N 33/53* (2006.01)
*C07K 16/00* (2006.01)
*C07K 16/20* (2006.01)
*G01N 33/569* (2006.01)

(52) U.S. Cl.
CPC .......... *C07K 16/20* (2013.01); *G01N 33/56905* (2013.01)

(58) Field of Classification Search
None
See application file for complete search history.

(56) References Cited

U.S. PATENT DOCUMENTS

| 5,006,309 | A | | 4/1991 | Khalil et al. |
| 5,063,081 | A | | 11/1991 | Cozzette et al. |
| 5,089,424 | A | | 2/1992 | Khalil et al. |
| 5,234,822 | A | | 8/1993 | Pereira et al. |
| 5,294,404 | A | | 3/1994 | Grandone et al. |
| 5,322,936 | A | | 6/1994 | Pereira et al. |
| 5,545,807 | A | | 8/1996 | Surani et al. |
| 5,569,825 | A | | 10/1996 | Lonberg et al. |
| 5,625,126 | A | | 4/1997 | Lonberg et al. |
| 5,633,425 | A | | 5/1997 | Lonberg et al. |
| 5,661,016 | A | | 8/1997 | Lonberg et al. |
| 6,054,135 | A | * | 4/2000 | Reed et al. ............... 424/269.1 |
| 6,180,370 | B1 | * | 1/2001 | Queen et al. ............... 435/69.6 |
| 7,491,515 | B2 | | 2/2009 | Kirchhoff et al. |
| 2003/0170881 | A1 | | 9/2003 | Davis et al. |
| 2004/0018577 | A1 | | 1/2004 | Emerson Campbell et al. |
| 2005/0054078 | A1 | | 3/2005 | Miller et al. |
| 2005/0227289 | A1 | | 10/2005 | Reilly et al. |
| 2006/0160164 | A1 | | 7/2006 | Miller et al. |
| 2006/0275329 | A1 | | 12/2006 | Urade et al. |

FOREIGN PATENT DOCUMENTS

| WO | WO-9002564 | 3/1990 |
| WO | WO-9308829 A1 | 5/1993 |
| WO | 96/29605 | 9/1996 |
| WO | WO-9627011 A1 | 9/1996 |
| WO | 00/50897 | 8/2000 |
| WO | WO-0158956 A2 | 8/2001 |
| WO | 2004050852 A2 | 6/2004 |
| WO | WO-2007056114 A2 | 5/2007 |

OTHER PUBLICATIONS

Harlow and Lane (Antibodies A Laboratory Manual, Cold Spring Harbor Press, 1988, pp. 27-28).*
Campbell (Monoclonal Antibody Technology, Elsevier Science Publishing Company Inc, 1986, Chapter 1, pp. 1-32).*
Kussie et al (J. Immunology, 152:146-52, 1994).*
Bendig (Methods: A Companion to Methods in Enzymology 1995; 8:83-93).*
Chen et al, (The Embo Journal, 14(12):2784-2794, 1995).*
Almeida IC, Covas DT, Soussumi LM, Travassos LR, "A highly sensitive and specific chemiluminescent enzyme-linked immunosorbent assay for diagnosis of active *Trypanosoma cruzi* infection.", Transfusion, 1997, 37/8, 850-7.
Altschul SF, et al., "Basic Local Alignment Search Tool", J Mol Biol, 1990, 215, 403-410.
Barbas CF 3RD, Bain JD, Hoekstra DM, Lerner RA, "Semisynthetic combinatorial antibody libraries: a chemical solution to the diversity problem", Proc Natl Acad Sci USA, 1992, 89-10, 4457-61.
Berzofsky JA, et al.; Paul WE, ED, Antigen-Antibody Interactions and Monoclonal Antibodies excerpt from undamental Immunology, 2nd ed. Raven Press, 1989, pp. 315-336.
Bittencourt AL, "Congenital Chagas Disease", Am J Dis Child, 1976, 130, 97-103.
Boerner P, Lafond R, Lu WZ, Brams P, Royston I, "Production of antigen-specific human monoclonal antibodies from in vitro-primed human splenocytes", J Immunol, 1991, 147/1, 86-95.
Brennan M, Davison PF, Paulus H, "Preparation of bispecific antibodies by chemical recombination of monoclonal immunoglobulin G1 fragments", Science, 1985, 229, 81-3.
Brodeur BR, Lagace J, Larose Y W/ Schook LB, ED., "Monoclonal Antibody Production Techniques and Applications: Mouse-Human Myeloma Partners for the Production of Heterohybridomas", Monoclonal Antibody Production Techniques and Applications, Marcel Dekker, Inc., 1987, 51-63.
Chagas C, "[Nova tripanozomiaze humana: Estudos sobre a morfolojia e o ciclo evolutive do *Schizotrypanum cruzi* n. gen., n. sp., ajente etiolojico de nova entidade morbida do homem]", Memorias do Instituto Oswaldo Cruz, 1909, 1, 159-218.

(Continued)

*Primary Examiner* — Patricia A Duffy
(74) *Attorney, Agent, or Firm* — Irene M. Reininger

(57) ABSTRACT

The present disclosure is directed to reagents and methods of using the reagents to detect epitopes of *Trypanosoma cruzi*.

11 Claims, 7 Drawing Sheets

(56) References Cited

OTHER PUBLICATIONS

Chagas C, "Neue Trypanosomen. Vorlaufige Mittielung", Arch Schiff Tropenhyg, 1909, 13, 120-122.
Chao et al., J. Mol. Biol, 2004, 342, pp. 539-550.
Cheng KY, Chang CD, Salbilla VA, et al., "Immunoblot assay using recombinant antigens as a supplemental test to confirm the presence of antibodies to *Trypanosoma cruzi*.", Clin Vaccine Immunol, 2007, 14/4, 355-61.
Clackson T, Hoogenboom HR, Griffiths AD, et al., "Making antibody fragments using phage display libraries", Nature, 1991, 352/6336, 624-8.
Coura JR, De Castro SL, "A critical review on Chagas disease chemotherapy", Mem Inst Oswaldo Cruz, 2002, 97/1, 3-24.
Fieck A, Wyborski DL, Short JM, "Modifications of the *E.coli* Lac repressor for expression in eukaryotic cells: effects of nuclear signal sequences on protein activity and nuclear accumulation", Nucleic Acids Res, 1992, 20/7, 1785-91.
Fishwild DM, O'Donnell SL, Bengoechea T, et al., "High-avidity human IgG kappa monoclonal antibodies from a novel strain of minilocus transgenic mice", Nat Biotechnol, 1996, 14/7, 845-51.
Galfre G, Howe SC, Milstein C, et al., "Antibodies to major histocompatibility antigens produced by hybrid cell lines", Nature, 1977, 266/5602, 550-2.
Goding, Monoclonal Antibodies: Principles & Practice: 3, Production of Monoclonal Antibodies, 1986, pp. 59-103.
Gomes ML, Galvao LM, Macedo AM, et al, "Chagas' disease diagnosis: comparative analysis of parasitologic, molecular, and serologic methods", Am J Trop Med Hyg, 1999, 60/2, 205-10.
Gonzalez A, Lerner TJ, Huecas M, et al., "Apparent generation of a segmented mRNA from two separate tandem gene families in *Trypanosoma cruzi*.", Nucleic Acids Res, 1985, 13/16, 5789-804.
Grant IH, Gold JW, Wittner M, et al., "Transfusion-associated acute Chagas disease acquired in the United States", Ann Intern Med, 1989, 111/10, 849-51.
Gruber M, Schodin BA, Wilson ER, Kranz DM, "Efficient tumor cell lysis mediated by a bispecific single chain antibody expressed in *Escherichia coli*", J Immunol, 1994, 152/11, 5368-74.
Harlow E, Lane D, Using Antibodies: A Laboratory Manual (Table of Contents).
Hoff R, Mott KE, Milanesi ML, et al., "Congenital Chagas's disease in an urban population: investigation of infected twins.", Trans R Soc Trop Med Hyg, 1978, 72/3, 247-50.
Holliger, P. et al., ""Diabodies": Small bivalent and Bispecific Antibody Fragments," Proc. Natl. Acad. Sci., 1993, 90, 6444-6448.
Hoogenboom HR, Griffiths AD, Johnson KS, et al., "Multi-subunit proteins on the surface of filamentous phage: methodologies for displaying antibody (Fab) heavy and light chains.", Nucleic Acids Res, 1991, 19/15, 4133-7.
Johnson KS, Chiswell DJ, "Human antibody engineering: Current Opinion in Structural Biology 1993, 3:564-571", Curr Opin Structural Biology, 1993, 3, 564-571.
Johnsson, B. et al., "Comparison of Methods for Immobilizatoin to Carboxymethyl Dextran Sensor Surfaces by Analysis of the Specific Activity of Monoclonal Antibodies," J. of Molecular Recog, 1995, 8, 125-131.
Johnsson, B. et al., "Immobilization of Proteins to a Carboxymethyldextran-Modified Gold Surface for Biospecific Interaction Analysis I Surface Plasmon Resonance Sensors," Analyt. Biochem., 1991, 198, 268-277.
Jones P.T. et al., "Replacing the complementarity-determining regions in a human antibody with those from a mouse," Nature, vol. 321, pp. 522-525, 1986.
Jonsson U, Fagerstam L, Lofas S, et al., "Introducing a biosensor based technology for real-time biospecific interaction analysis", Ann Biol Clin (Paris), 1993, 51/1, 19-26.
Kaufman RJ, "Vectors used for expression in mammalian cells", Methods Enzymol, 1990, 185, 487-511.
Kirchhoff LV, "Is *Trypanosoma cruzi* a new threat to our blood supply?", Ann Intern Med, 1989, 110/10, 773-5.
Kirchhoff LV; Guerrant RL, Walker DH, Weller PF, EDS., American Trypanosomiasis (Chagas' Disease) in Tropical Infectious Disease Principles, Pathogens, & Practice, $2^{nd}$ edition, Guerrant R.L.., et al., eds., Churchill Livingstone, 2006, pp. 1082-1094.
Kohler G, Milstein C, "Continuous cultures of fused cells secreting antibody of predefined specificity", Nature, 1975, 256/5517, 495-7.
Kostelny SA, Cole MS, Tso JY, "Formation of a bispecific antibody by the use of leucine zippers", J Immunol, 1992, 148/5, 1547-53.
Kozak M, "At least six nucleotides preceding the AUG initiator codon enhance translation in mammalian cells", J Mol Biol, 1987, 196/4, 947-50.
Kozbor D, Tripputi P, Roder JC, Croce CM, "A human hybrid myeloma for production of human monoclonal antibodies.", J Immunol, 1984, 133/6, 3001-5.
Lafaille JJ, Linss J, Krieger MA, et al., "Structure and expression of two *Trypanosoma cruzi* genes encoding antigenic proteins bearing repetitive epitopes", Mol Biochem Parasitol, 1989, 35/2, 127-36.
Leiby DA, Wendel S, Takaoka DT, et al., "Serologic testing for *Trypanosoma cruzi*: comparison of radioimmunoprecipitation assay with commercially available indirect immunofluorescence assay, indirect hemagglutionation assay, and enzyme-linked immunosorbent assay kits.", J Clin Microbiol, 2000, 38/2, 639-42.
Marks JD, Hoogenboom HR, Bonnert TP, et al., "By-passing immunization. Human antibodies from V-gene libraries displayed on phage", J Mol Biol, 1991, 222/3, 581-97.
Mizushima, S. et al., "pEF-BOS, a powerful mammalian expression vector," Nucl. Acids Res., 18 (17), 5322.
Morrison et al., "Chimeric human antibody molecules: mouse antigen-binding domains with human constant region domains.," Proc. Natl. Acad. Sci., 1984, 81, 6851-6855.
Munson PJ, Rodbard D, "Ligand: a versatile computerized approach for characterization of ligand-binding systems", Anal Biochem, 1980, 107/1, 220-39.
Otsu K, Donelson JE, Kirchhoff LV, "Interruption of a *Trypanosoma cruzi* gene encoding a protein containing 14-amino acid repeats by targeted insertion of the neomycin phosphotransferase gene.", Mol Biochem Parasitol, 1993, 57/2, 317-30.
Ouaissi A, Aguirre T, Plumas-Marty B, et al., "Cloning and sequencing of a 24-kDa *Trypanosoma cruzi* specific antigen released in association with membrane vesicles and defined by a monoclonal antibody", Biol Cell, 1992, 75/1, 11-7.
PCT Search Report for PCT/US2008/088199.
Redhead SA, Cushion MT, Frenkel JK, Stringer JR, "Pneumocystis and *Trypanosoma cruzi*: nomenclature and typifications.", J Eukaryot Microbiol, 2006, 53/1, 2-11.
Reisfeld RA, Sell S, Eds., Monoclonal Antibodies and Cancer Therapy: Proceedings of the Roche-UCLA Symposium Held in Park City, Utah Jan. 26-Feb. 2, 1985.
Riechmann L, Clark M, Waldmann H, Winter G, "Reshaping human antibodies for therapy.", Nature, 1988, 332, 323-7.
Schade R, Staak C, Hendriksen C, et al., "The Production of Avian (Egg Yolk) Antibodies: IgY", ATLA, 1996, 24, 925-34.
Schwartz RM; Dayhoff M, ED, Matrices for Detecting Distant Relationships in: Atlas of Protein Sequence and Structure, vol. 5 (Suppl. 3), Dayhoff M.O., ed., National Biomedical Research Foundation, 1978, pp. 353-358.
Segura E.L. et al.,"Xenodiagnosis" in Chagas' Disease Vectors: vol. II Anatomic and Physiological Aspects; Brenner R.R. et al.,eds., CRC Press, 1987, pp. 41-45.
Shalaby MR, "Development of Humanized Bispecific Antibodies Reactive with Cytotoxic Lymphocytes and Tumor Cells Overexpressing the HER2 Protooncogene", J Exp Med, 1992, 175, 217-225.
Skolnick A, "Does Influx From Endemic Areas Mean More Transfusion-Associated Chagas' Disease?", JAMA, 1989, 262/11, 1433.
Smith TF, Waterman MS, "Comparison of Biosequences", Adv App Math, 1981, 2, 482-489.
Smith TF, Waterman MS, "Identification of common molecular subsequences", J Mol Biol, 1981, 147/1, 195-7.
Suresh MR, Cuello AC, Milstein C, "Bispecific monoclonal antibodies from hybrid hybridomas in: Production of Hybridomas", Methods in Enzymology, 1986, 121, 210-228.

(56) References Cited

OTHER PUBLICATIONS

Tachibana H, Nagakura K, Kaneda Y, "Serodiagnosis of Chagas' disease using monoclonal antibody against *Trypanosoma cruzi*-specific Mr 25,000 antigen", Parasitol Res, 1988, 74/5, 409-14.

Traunecker A, Aliveri F, Karjalainen K, "Myeloma based expression system for production of large mammalian proteins.", Trends Biotechnol, 1991, 9/4, 109-13.

Tutt A, Stevenson GT, Glennie MJ, "Trispecific F(ab')3 derivatives that use cooperative signaling via the TCR/CD3 complex and CD2 to activate and redirect resting cytotoxic T cells.", J Immunol, 1991, 147, 60-9.

Verhoeyen M, Milstein C, Winter G, "Reshaping human antibodies: grafting an antilysozyme activity.", Science, 1988, 239/4847, 1534-6.

Wands JR, Zurawski VR, "High affinity monoclonal antibodies to hepatitis B surface antigen (HBsAg) produced by somatic cell hybrids.", Gastroenterol, 1981, 80/2, 225-32.

Wu C, Ying H, Grinnel C, et al., "Simultaneous targeting of multiple disease mediators by a dual-variable-domain immunoglobulin.", Nat Biotechnol, 2007, 25/11, 1290-7.

Wyborski DL, Ducoeur LC, Short JM, "Parameters affecting the use of the lac repressor system in eukaryotic cells and transgenic animals.", Environ Mol Mutagen, 1996, 28/4, 447-58.

Wyborski DL, Short JM, "Analysis of inducers of the *E.coli* lac repressor system in mammalian cells and whole animals.", Nucleic Acids Res, 1991, 19/17, 4647-53.

Brown, M. et al., "Tolerance to single, but not multiple, amino acid replacements in antibody VH CDR2. A means of minimizing B cell wastage from somatic hypermutation," J. Immunol. (1996) 156(9):3285-3291.

Ofran, Y. et al., "Automated identification of complementarity determining regions (CDRs) reveals peculiar characteristics of CDRs and B cell epitopes," J. Immunol. (2008) 181:6230-6235.

Winkler, K. et al., "Changing the antigen binding specificity by single point mutations of an anti-p24 (HIV-1) antibody," J. Immunol. (2000) 165:4505-4514.

International Preliminary Report on Patentability for Application No. PCT/US2008/088199, mailed on Jun. 29, 2010, 1 page.

* cited by examiner

Heavy Chain Signal Peptide
```
2701                                                              TGGAGTTT GGGCTGAGCT GGCTTTTCT (SEQ ID NO.:21)
                                                         ACCTCAAA CCCGACTCGA CCGAAAAGA (SEQ ID NO.:22)
                                                                              VH5

Heavy Chain Signal Peptide
      ------------------------------------------------------------------------------------------------------
2801  TGTCGCGATT TTAAAAGTTG TCCAGTGCGA TGTGCAGCTG GTGGAGTCTG GGGGAGGCTT AGTGCAGCCT GGAGGGTCCC GAAACTCTC  CTGTGCAGCC
      ACAGCGCTAA AATTTTCCAC AGGTCACGCT ACACGTCGAC CACCTCAGAC CCCCTCCGAA TCAGTCGGA CCTCCCAGGG CCTTTGAGAG GACACGTCGG
                                                                       VH5

2901  TCTGGATTCA CTTTCAGTGT CTTTGAATG CACTGGGTTC GTCAGGCTCC AGAGAAGGGG CTGGAGTGGG TCGCATACAT TAGTAGTGGC AGTACTATCA
      AGACCTAAGT GAAAGTCACA GAAACTTAC GTGACCCAAG CAGTCCGAGG TCTCTTCCCC GACCTCACCC AGCGTATGTA ATCATCACCG TCATGATAGT
                                                                       VH5

3001  TCTATTATGC AGACACAGTG AAGGGCCGAT TCACCATCTC CAGAGACAAT CCCAAGAACA CCCTGTTCCT GCAAATGACC GGTCTAAGGT CTGAGGACAC
      AGATAATACG TCTGTGTCAC TTCCCGGCTA AGTGGTAGAG GTCTCTGTTA GGGTTCTTGT GGGACAAGGA CGTTTACTGG CCAGATTCCA GACTCCTGTG
                                                                       VH5                               hCg1,z,non-a 3101  GGCCATGTAT TACTGTGCAA GACCGCTCTA CTATGATTAC GACGACTATG CTATGGACTA GAACCTCAG TCACCGTCTC CTCAGCGTCG
      CCGGTACATA ATGACACGTT CTGGCGAGAT GATACTAATG CTGCTGATAC CTTGGAGTC AGTGGCAGAG GAGTCGCAGC
                                                   hCg1,z,non-a 3201  ACCAAGGGCC CATCGGTCTT CCCCCTGGCA CCCTCCTCCA AGAGCACCTC TGGGGGCACA GCGGCCCTGG GCTGCCTGGT CAAGGACTAC TTCCCCGAAC
      TGGTTCCCGG GTAGCCAGAA GGGGGACCGT TCTCGTGGAG ACCCCCGTGT CGCCGGGACC CGACGGACGA GTTCCTGATG AAGGGGCTTG
                                                   hCg1,z,non-a 3301  CGGTGACGGT GTCGTGGAAC TCAGGCGCCC TGACCAGCGG CGTGCACACC TTCCCGGCTG TCCTACAGTC CTCAGGACTC TACTCCCTCA GCAGCGTGGT
      GCCACTGCCA CAGCACCTTG AGTCCGCGGG ACTGGTCGCC GCACGTGTGG AAGGGCCGAC ACTGGTCAG GAGTCCTGAG ATGAGGGAGT CGTCGCACCA
                                                   hCg1,z,non-a 3401  GACCGTGCCC TCCAGCAGCT TGGGCACCCA GACCTACATC TGCAACGTGA ATCACAAGCC CAGCAACACC AAGGTGGACA AGAAAGTTGA GCCCAAATCT
      CTGGCACGGG AGGTCGTCGA ACCCGTGGGT CTGGATGTAG ACGTTGCACT TAGTGTTCGG GTCGTTGTGG TTCCACCTGT TCTTTCAACT CGGGTTTAGA
```

Figure 3A

```
                                     hCg1,z,non-a
3501  TGTGACAAAA CTCACACATG CCCACCGTGC CCAGCACCTG AACTCCTGGG GGGACCGTCA GTCTTCCTCT TCCCCCAAA ACCCAAGGAC ACCCTCATGA
      ACACTGTTTT GAGTGTGTAC GGGTGGCACG GGTCGTGGAC TTGAGGACCC CCCTGGCAGT CAGAAGGAGA AGGGGGGTTT TGGGTTCCTG TGGGAGTACT
                                     hCg1,z,non-a
3601  TCTCCCGGAC CCCTGAGGTC ACATGCGTGG TGGTGGACGT GAGCCACGAA GACCCTGAGG TCAAGTTCAA CTGGTACGTG GACGGCGTGG AGGTGCATAA
      AGAGGGCCTG GGGACTCCAG TGTACGCACC ACCACCTGCA CTCGGTGCTT CTGGGACTCC AGTTCAAGTT GACCATGCAC CTGCCGCACC TCCACGTATT
                                     hCg1,z,non-a
3701  TGCCAAGACA AAGCCGCGGG AGGAGCAGTA CAACAGCACG TACCGTGTGG TCAGCGTCCT CACCGTCCTG CACCAGGACT GGCTGAATGG CAAGGAGTAC
      ACGGTTCTGT TTCGGCGCCC TCCTCGTCAT GTTGTCGTGC ATGGCACACC AGTCGCAGGA GTGGCAGGAC GTGGTCCTGA CCGACTTACC GTTCCTCATG
                                     hCg1,z,non-a
3801  AAGTGCAAGG TCTCCAACAA AGCCCTCCCA GCCCCCATCG AGAAAACCAT CTCCAAAGCC AAAGGGCAGC CCCGAGAACC ACAGGTGTAC ACCCTGCCCC
      TTCACGTTCC AGAGGTTGTT TCGGGAGGGT CGGGGGTAGC TCTTTTGGTA GAGGTTTCGG TTTCCCGTCG GGGCTCTTGG TGTCCACATG TGGGACGGGG
                                     hCg1,z,non-a
3901  CATCCCGCGA GGAGATGACC AAGAACCAGG TCAGCCTGAC CTGCCTGGTC AAAGGCTTCT ATCCCAGCGA CATCGCCGTG GAGTGGGAGA GCAATGGGCA
      GTAGGGCGCT CCTCTACTGG TTCTTGGTCC AGTCGGACTG GACGGACCAG TTTCCGAAGA TAGGGTCGCT GTAGCGGCAC CTCACCCTCT CGTTACCCGT
                                     hCg1,z,non-a
4001  GCCGGAGAAC AACTACAAGA CCACGCCTCC CGTGCTGGAC TCCGACGGCT CCTTCTTCCT CTACAGCAAG CTCACCGTGG ACAAGAGCAG GTGGCAGCAG
      CGGCCTCTTG TTGATGTTCT GGTGCGGAGG GCACGACCTG AGGCTGCCGA GGAAGAAGGA GATGTCGTTC GAGTGGCACC TGTTCTCGTC CACCGTCGTC
                                     hCg1,z,non-a
4101  GGGAACGTCT TCTCATGCTC CGTGATGCAT GAGGCTCTGC ACAACCACTA CACGCAGAAG AGCCTCTCCC TGTCTCCGGG TAAATGA
      CCCTTGCAGA AGAGTACGAG GCACTACGTA CTCCGAGACG TGTTGGTGAT GTGCGTCTTC TCGGAGAGGG ACAGAGGCCC ATTTACT
```

Figure 3B

```
                                                                Kappa Signal Peptide
                                                        ------------------------------------------
                                          TGGACATGCG CGTGCCCGCC CAGCTGCTGG GCCTGCTGCT (SEQ ID NO.:23)
                                          ACCTGTACGC GCACGGGCGG GTCGACGACC CGGACGACGA (SEQ ID NO.:24)
                                          ------------------------------------------
                                                            Vk8

Kappa Signal Peptide
-------------------------------------
7401

7501   GCTGTGGTTC CCCGGCTCGC GATGCTACAT TGTGATGTCA CAGTCTCCAT CCTCCCTGCC TGTGTCAGCA GGAGAGAAGG TCACTATGAG CTGCAAATCC
       CGACACCAAG GGGCCGAGCG CTACGATGTA ACACTACAGT GTCAGAGGTA GGAGGGACCG ACACAGTCGT CCTCTCTTCC AGTGATACTC GACGTTTAGG
                                                        Vk8

7601   AGTCAGAGTC TGCTCAACAG TAGAACCCGA AAGAAGCACT TGGCTTGGTA TCAGCAGAAA CCAGGGCAGT CTCCTAAACT GCTGATCTAC TGGGCATCCA
       TCAGTCTCAG ACGAGTTGTC ATCTTGGGCT TTCTTGGTGA ACCGAACCAT AGTCGTCTTT GGTCCCGTCA GAGGATTTGA CGACTAGATG ACCGTAGGT
                                                        Vk8

7701   CTAGGGAATC TGGGGTCCCT GATCCGTTCA CAGGCAGTGG ATCTGGGACA GATTTCGCTC TCACCATCAG CAGTGTGCAG GCTGAAGACC TGGCAGTTTA
       GATCCCTTAG ACCCCAGGGA CTAGCGAAGT GTCCGTCACC TAGACCCTGT CTAAAGCGAG AGTGGTAGTC GTCACACGTC CGACTTCTGG ACCGTCAAAT
                                                                                                        hCk

7801   TTTCTGCAAG CAATCTTATA ATCTGTACAC AATTCGGTGCT GGGACCAAGC TGGAGCTGAA ACGTACGGTG GCTGCACCAT CTGTCTTCAT CTTCCCGCCA
       AAAGACGTTC GTTAGAATAT TAGACATGTG TTAAGCCACGA CCCTGGTTCG ACCTCGACTT TGCATGCCAC CGACTGGTA GACAGAAGTA GAAGGGCGGT
                                                            hCk

7901   TCTGATGAGC AGTTGAAATC TGGAACTGCC TCTGTTGTGT GCCTGCTGAA TAACTTCTAT CCCAGAGAGG CCAAAGTACA GTGGAAGGTG GATAACGCCC
       AGACTACTCG TCAACTTTAG ACCTTGACGG AGACAACACA CGGACGACTT ATTGAAGATA GGGTCTCTCC GGTTTCATGT CACCTTCCAC CTATTGCGGG
                                                             hCk

8001   TCCAATCGGG TAACTCCCAG GAGAGTGTCA CAGAGCAGGA CAGCAAGGAC AGCACCTACA GCCTCAGCAG CACCCTGACG CTGAGCAAAG CTGACTACGA
       AGGTTAGCCC ATTGAGGGTC CTCTCACAGT GTCTCGTCCT GTCGTTCCTG TCGTGGATGT CGGAGTCGTC GTGGGACTGC GACTCGTTTC GACTGATGCT
                                                            hCk

8101   GAAACACAAA GTCTACGCCT GCGAAGTCAC CCATCACGGG CTGAGCTCGC CCGTCACAAA GAGCTTCAAC AGGGGAGAGT GTTGA
       CTTTGTGTTT CAGATGCGGA CGCTTCAGTG GGTAGTGCCCG GACTCGAGCG GGCAGTGTTT CTCGAAGTTG TCCCCTCTCA CAACT
```

Figure 3C

SEQUENCE LISTING

<160> NUMBER OF SEQ ID NOS: 28

<210> SEQ ID NO 1
<211> LENGTH: 1518
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 1

| | | | | | |
|---|---|---|---|---|---|
| atggcccagc | tccaacaggc | agaaaataat | atcactaatt | ccaaaaaaga | aatgacaaag | 60 |
| ctacgagaaa | aagtgaaaaa | ggccgagaaa | gaaaaattgg | acgccattaa | ccgggcaacc | 120 |
| aagctggaag | aggaacgaaa | ccaagcgtac | aaagcagcac | acaaggcaga | ggaggaaaag | 180 |
| gctaaaacat | ttcaacgcct | tataacattt | gagtcggaaa | atattaactt | aaagaaaagg | 240 |
| ccaaatgacg | cagtttcaaa | tcgggataag | aaaaaaaatt | ctgaaaccgc | aaaaactgac | 300 |
| gaagtagaga | aacagagggc | ggctgaggct | gccaaggccg | tggagacgga | gaagcagagg | 360 |
| gcagctgagg | ccacgaaggt | tgccgaagcg | gagaagcgga | aggcagctga | ggccgccaag | 420 |
| gccgtggaga | cggagaagca | gagggcagct | gaagccacga | aggttgccga | agcggagaag | 480 |
| cagaaggcag | ctgaggccgc | caaggccgtg | gagacggaga | gcagagggc | agctgaagcc | 540 |
| acgaaggttg | ccgaagcgga | gaagcagagg | gcagctgaag | ccatgaaggt | tgccgaagcg | 600 |
| gagaagcaga | aggcagctga | ggccgccaag | gccgtggaga | cggagaagca | gagggcagct | 660 |
| gaagccacga | aggttgccga | agcggagaag | cagaaggcag | ctgaggccgc | caaggccgtg | 720 |
| gagacggaga | gcagagggc | agctgaagcc | acgaaggttg | ccgaagcgga | gaagcagaag | 780 |
| gcagctgagg | ccgccaaggc | cgtggagacg | gagaagcaga | gggcagctga | agccacgaag | 840 |
| gttgccgaag | cggagaagga | tatcgatccc | atgggtgctt | gtgggtcgaa | ggactcgacg | 900 |
| agcgacaagg | ggttggcgag | cgataaggac | ggcaagaacg | ccaaggaccg | caaggaagcg | 960 |
| tgggagcgca | ttcgccaggc | gattcctcgt | gagaagaccg | ccgaggcaaa | acagcgccgc | 1020 |
| atcgagctct | tcaagaagtt | cgacaagaac | gagaccggga | agctgtgcta | cgatgaggtg | 1080 |
| cacagcggct | gcctcgaggt | gctgaagttg | gacgagttca | cgccgcgagt | gcgcgacatc | 1140 |
| acgaagcgtg | cattcgacaa | ggcgagggcc | ctgggcagca | agctggagaa | caagggctcc | 1200 |
| gaggactttg | ttgaatttct | ggagttccgt | ctgatgctgt | gctacatcta | cgacttcttc | 1260 |
| gagctgacgg | tgatgttcga | cgagattgac | gcctccggca | acatgctggt | tgacgaggag | 1320 |
| gagttcaagc | gcgccgtgcc | caggcttgag | gcgtggggcg | ccaaggtcga | ggatcccgcg | 1380 |
| gcgctgttca | aggagctcga | taagaacggc | actgggtccg | tgacgttcga | cgagtttgct | 1440 |
| gcgtgggctt | ctgcagtcaa | actggacgcc | gacggcgacc | cggacaacgt | gccggagagc | 1500 |
| ccgagaccga | tgggaatc | | | | | 1518 |

<210> SEQ ID NO 2

```
<211> LENGTH: 506
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Met Ala Gln Leu Gln Gln Ala Glu Asn Asn Ile Thr Asn Ser Lys Lys
 1               5                  10                  15

Glu Met Thr Lys Leu Arg Glu Lys Val Lys Lys Ala Glu Lys Glu Lys
                20                  25                  30

Leu Asp Ala Ile Asn Arg Ala Thr Lys Leu Glu Glu Glu Arg Asn Gln
            35                  40                  45

Ala Tyr Lys Ala Ala His Lys Ala Glu Glu Lys Ala Lys Thr Phe
        50                  55                  60

Gln Arg Leu Ile Thr Phe Glu Ser Glu Asn Ile Asn Leu Lys Lys Arg
 65                  70                  75                  80

Pro Asn Asp Ala Val Ser Asn Arg Asp Lys Lys Asn Ser Glu Thr
                 85                  90                  95

Ala Lys Thr Asp Glu Val Glu Lys Gln Arg Ala Ala Glu Ala Ala Lys
                100                 105                 110

Ala Val Glu Thr Glu Lys Gln Arg Ala Ala Glu Ala Thr Lys Val Ala
            115                 120                 125

Glu Ala Glu Lys Arg Lys Ala Ala Glu Ala Ala Lys Ala Val Glu Thr
130                 135                 140

Glu Lys Gln Arg Ala Ala Glu Ala Thr Lys Val Ala Glu Ala Glu Lys
145                 150                 155                 160

Gln Lys Ala Ala Glu Ala Ala Lys Ala Val Glu Thr Glu Lys Gln Arg
                165                 170                 175

Ala Ala Glu Ala Thr Lys Val Ala Glu Ala Glu Lys Gln Arg Ala Ala
            180                 185                 190

Glu Ala Met Lys Val Ala Glu Ala Glu Lys Gln Lys Ala Ala Glu Ala
        195                 200                 205

Ala Lys Ala Val Glu Thr Glu Lys Gln Arg Ala Ala Glu Ala Thr Lys
    210                 215                 220

Val Ala Glu Ala Glu Lys Gln Lys Ala Ala Glu Ala Ala Lys Ala Val
225                 230                 235                 240

Glu Thr Glu Lys Gln Arg Ala Ala Glu Ala Thr Lys Val Ala Glu Ala
                245                 250                 255

Glu Lys Gln Lys Ala Ala Glu Ala Ala Lys Ala Val Glu Thr Glu Lys
            260                 265                 270

Gln Arg Ala Ala Glu Ala Thr Lys Val Ala Glu Ala Glu Lys Asp Ile
        275                 280                 285

Asp Pro Met Gly Ala Cys Gly Ser Lys Asp Ser Thr Ser Asp Lys Gly
    290                 295                 300

Leu Ala Ser Asp Lys Asp Gly Leu Asn Ala Lys Asp Arg Lys Glu Ala
305                 310                 315                 320

Trp Glu Arg Ile Arg Gln Ala Ile Pro Arg Glu Lys Thr Ala Glu Ala
                325                 330                 335

Lys Gln Arg Arg Ile Glu Leu Phe Lys Lys Phe Asp Lys Asn Glu Thr
            340                 345                 350

Gly Lys Leu Cys Tyr Asp Glu Val His Ser Gly Cys Leu Glu Val Leu
        355                 360                 365

Lys Leu Asp Glu Phe Thr Pro Arg Val Arg Asp Ile Thr Lys Arg Ala
```

```
                    370                 375                 380
Phe Asp Lys Ala Arg Ala Leu Gly Ser Lys Leu Glu Asn Lys Gly Ser
385                 390                 395                 400

Glu Asp Phe Val Glu Phe Leu Glu Phe Arg Leu Met Leu Cys Tyr Ile
                405                 410                 415

Tyr Asp Phe Phe Glu Leu Thr Val Met Phe Asp Glu Ile Asp Ala Ser
            420                 425                 430

Gly Asn Met Leu Val Asp Glu Glu Phe Lys Arg Ala Val Pro Arg
        435                 440                 445

Leu Glu Ala Trp Gly Ala Lys Val Glu Asp Pro Ala Ala Leu Phe Lys
    450                 455                 460

Glu Leu Asp Lys Asn Gly Thr Gly Ser Val Thr Phe Asp Glu Phe Ala
465                 470                 475                 480

Ala Trp Ala Ser Ala Val Lys Leu Asp Ala Asp Gly Asp Pro Asp Asn
                485                 490                 495

Val Pro Glu Ser Pro Arg Pro Met Gly Ile
            500                 505
```

```
<210> SEQ ID NO 3
<211> LENGTH: 66
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3
ggtgacaaac catcaccatt tggacaggcc gcagcaggtg acaaaccatc accatttgga     60
caggcc                                                               66

<210> SEQ ID NO 4
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gly Asp Lys Pro Ser Pro Phe Gly Gln Ala Ala Ala Gly Asp Lys Pro
  1               5                  10                  15

Ser Pro Phe Gly Gln Ala
             20

<210> SEQ ID NO 5
<211> LENGTH: 1557
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5
gatccaacgt atcgttttgc aaaccacgcg ttcacgctgg tggcgtcggt gacgattcac    60
gaggttccga gcgtcgcgag tcctttgctg ggtgcgagcc tggactcttc tggtggcaaa   120
aaactcctgg ggtctctcgta cgacgagaag caccagtggc agccaatata cggatcaacg   180
ccggtgacgc cgaccggatc gtgggagatg ggtaagaggt accacgtggt tcttacgatg   240
gcgaataaaa ttggctccgt gtacattgat ggagaacctc tggagggttc agggcagacc   300
```

```
gttgtgccag acgagaggac gcctgacatc tcccacttct acgttggcgg gtatggaagg    360
agtgatatgc caaccataag ccacgtgacg gtgaataatg ttcttcttta caaccgtcag    420
ctgaatgccg aggagatcag gaccttgttc ttgagccagg acctgattgg cacggaagca    480
cacatgggca gcagcagcgg cagcagtgcc acggtacgc cctcgattcc cgttgacagc     540
agtgcccacg gtacaccctc gactcccgtt gacagcagtg cccacggtac gccctcgact    600
cccgttgaca gcagtgccca cggtacaccc tcgactcccg ttgacagcag tgcccacggt    660
acaccctcga ctcccgttga cagcagtgcc acggtaagc cctcgactcc cgctgacagc     720
agtgcccaca gtacgccctc gactcccgct gacagcagtg cccacagtac gcctcaatt     780 cccgctgaca gcagtgccca gtacgccc tcagctcccg ctgacaacgg cgccaatggt      840
acggttttga ttttgtcgac tcatgacgcg tacaggcccg ttgatccctc ggcgtacaag    900
cgcgccttgc cgcaggaaga gcaagaggat gtggggccgc gccacgttga tcccgaccac    960
ttccgctcga cctcgacgac tcatgacgcg tacaggcccg ttgatccctc ggcgtacaag   1020
cgcgccttgc cgcaggaaga gcaagaggat gtggggccgc gccacgttga tcccgaccac   1080
ttccgctcga cgactcatga cgcgtacagg cccgttgatc cctcggcgta caagcgcgcc   1140
ttgccgcagg aagagcaaga ggatgtgggg ccgcgccacg ttgatcccga ccacttccgc   1200
tcgacctcga cgactcatga cgcgtacagg cccgttgatc cctcggcgta caagcgcgcc   1260
ttgccgcagg aagagcaaga ggatgtgggg ccgcgccacg ttgatcccga ccacttccgc   1320
tcgacctcga cgactcatga cgcgtacagg cccgttgatc cctcggcgta caagcgcgcc   1380
ttgccgcagg aagagcaaga ggatgtgggg ccgcgccacg ttgatcccga ccacttccgc   1440
tcgacgactc atgacgcgta caggcccgtt gatccctcgg cgtacaagcg cgccttgccg   1500
caggaagagc aagaggatgt ggggccgcgc cacgttgatc ccgaccactt ccgctcg      1557

<210> SEQ ID NO 6
<211> LENGTH: 519
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Asp Pro Thr Tyr Arg Phe Ala Asn His Ala Phe Thr Leu Val Ala Ser
 1               5                  10                  15

Val Thr Ile His Glu Val Pro Ser Val Ala Ser Pro Leu Leu Gly Ala
            20                  25                  30

Ser Leu Asp Ser Ser Gly Gly Lys Lys Leu Leu Gly Leu Ser Tyr Asp
        35                  40                  45

Glu Lys His Gln Trp Gln Pro Ile Tyr Gly Ser Thr Pro Val Thr Pro
    50                  55                  60

Thr Gly Ser Trp Glu Met Gly Lys Arg Tyr His Val Val Leu Thr Met
65                  70                  75                  80

Ala Asn Lys Ile Gly Ser Val Tyr Ile Asp Gly Glu Pro Leu Glu Gly
                85                  90                  95

Ser Gly Gln Thr Val Val Pro Asp Glu Arg Thr Pro Asp Ile Ser His
            100                 105                 110

Phe Tyr Val Gly Gly Tyr Gly Arg Ser Asp Met Pro Thr Ile Ser His
        115                 120                 125

Val Thr Val Asn Asn Val Leu Leu Tyr Asn Arg Gln Leu Asn Ala Glu
    130                 135                 140
```

```
Glu Ile Arg Thr Leu Phe Leu Ser Gln Asp Leu Ile Gly Thr Glu Ala
145                 150                 155                 160

His Met Gly Ser Ser Gly Ser Ser Ala His Gly Thr Pro Ser Ile
                165                 170                 175

Pro Val Asp Ser Ser Ala His Gly Thr Pro Ser Thr Pro Val Asp Ser
            180                 185                 190

Ser Ala His Gly Thr Pro Ser Thr Pro Val Asp Ser Ser Ala His Gly
        195                 200                 205

Thr Pro Ser Thr Pro Val Asp Ser Ser Ala His Gly Thr Pro Ser Thr
    210                 215                 220

Pro Val Asp Ser Ser Ala His Gly Lys Pro Ser Thr Pro Ala Asp Ser
225                 230                 235                 240

Ser Ala His Ser Thr Pro Ser Thr Pro Ala Asp Ser Ser Ala His Ser
                245                 250                 255

Thr Pro Ser Ile Pro Ala Asp Ser Ser Ala His Ser Thr Pro Ser Ala
            260                 265                 270

Pro Ala Asp Asn Gly Ala Asn Gly Thr Val Leu Ile Leu Ser Thr His
        275                 280                 285

Asp Ala Tyr Arg Pro Val Asp Pro Ser Ala Tyr Lys Arg Ala Leu Pro
    290                 295                 300

Gln Glu Glu Gln Glu Asp Val Gly Pro Arg His Val Asp Pro Asp His
305                 310                 315                 320

Phe Arg Ser Thr Ser Thr Thr His Asp Ala Tyr Arg Pro Val Asp Pro
                325                 330                 335

Ser Ala Tyr Lys Arg Ala Leu Pro Gln Glu Glu Gln Glu Asp Val Gly
            340                 345                 350

Pro Arg His Val Asp Pro Asp His Phe Arg Ser Thr Thr His Asp Ala
        355                 360                 365

Tyr Arg Pro Val Asp Pro Ser Ala Tyr Lys Arg Ala Leu Pro Gln Glu
    370                 375                 380

Glu Gln Glu Asp Val Gly Pro Arg His Val Asp Pro Asp His Phe Arg
385                 390                 395                 400

Ser Thr Ser Thr Thr His Asp Ala Tyr Arg Pro Val Asp Pro Ser Ala
                405                 410                 415

Tyr Lys Arg Ala Leu Pro Gln Glu Glu Gln Glu Asp Val Gly Pro Arg
            420                 425                 430

His Val Asp Pro Asp His Phe Arg Ser Thr Ser Thr Thr His Asp Ala
        435                 440                 445

Tyr Arg Pro Val Asp Pro Ser Ala Tyr Lys Arg Ala Leu Pro Gln Glu
    450                 455                 460

Glu Gln Glu Asp Val Gly Pro Arg His Val Asp Pro Asp His Phe Arg
465                 470                 475                 480

Ser Thr Thr His Asp Ala Tyr Arg Pro Val Asp Pro Ser Ala Tyr Lys
                485                 490                 495

Arg Ala Leu Pro Gln Glu Glu Gln Glu Asp Val Gly Pro Arg His Val
            500                 505                 510

Asp Pro Asp His Phe Arg Ser
        515

<210> SEQ ID NO 7
<211> LENGTH: 213
<212> TYPE: DNA
<213> ORGANISM: Artificial Sequence
<220> FEATURE:
```

<223> OTHER INFORMATION: Description of Artificial Sequence: Synthetic
    polynucleotide

<400> SEQUENCE: 7

```
atggagtcag agcgtcaga tcagctgctc gagaaggacc cgcgtcagga acgcgaagga    60
gattgctgcg cttgaggaga gtcatgaatg cccgcgtcat caggagctgg cgcgcgagaa   120
gaagcttgcc gaccgcgcgt tccttgactc agaagccgga gcgcgtgccg ctggctgacg   180
tgccgctcga cgacgatcag cgactttgtt gcg                                213
```

<210> SEQ ID NO 8
<211> LENGTH: 68
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 8

Met Glu Gln Glu Arg Arg Gln Leu Leu Glu Lys Asp Pro Arg Arg Asn
 1               5                  10                  15

Ala Lys Glu Ile Ala Ala Leu Glu Glu Ser Met Asn Ala Arg Ala Gln
                20                  25                  30

Glu Leu Ala Arg Glu Lys Lys Leu Ala Asp Arg Ala Phe Leu Asp Gln
            35                  40                  45

Lys Pro Glu Arg Val Pro Leu Ala Asp Val Pro Leu Asp Asp Asp Ser
        50                  55                  60

Asp Phe Val Ala
 65

<210> SEQ ID NO 9
<211> LENGTH: 336
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 9

```
tacattgtga tgtcacagtc tccatcctcc ctggctgtgt cagcaggaga gaaggtcact    60
atgagctgca aatccagtca gagtctgctc aacagtagaa cccgaaagaa ccacttggct   120
tggtatcagc agaaaccagg gcagtctcct aaactgctga tctactgggc atccactagg   180
gaatctgggg tccctgatcg cttcacaggc agtggatctg ggacagattt cgctctcacc   240
atcagcagtg tgcaggctga agacctggca gtttatttct gcaagcaatc ttataatctg   300
tacacattcg gtgctgggac caagctggag ctgaaa                             336
```

<210> SEQ ID NO 10
<211> LENGTH: 112
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 10

Tyr Ile Val Met Ser Gln Ser Pro Ser Ser Leu Ala Val Ser Ala Gly
 1               5                  10                  15

Glu Lys Val Thr Met Ser Cys Lys Ser Ser Gln Ser Leu Leu Asn Ser
                20                  25                  30

Arg Thr Arg Lys Asn His Leu Ala Trp Tyr Gln Gln Lys Pro Gly Gln
            35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Ala Leu Thr
65                  70                  75                  80

Ile Ser Ser Val Gln Ala Glu Asp Leu Ala Val Tyr Phe Cys Lys Gln
                85                  90                  95

Ser Tyr Asn Leu Tyr Thr Phe Gly Ala Gly Thr Lys Leu Glu Leu Lys
            100                 105                 110

<210> SEQ ID NO 11
<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11
gatgtgcagc tggtggagtc tgggggaggc ttagtgcagc ctggagggtc cggaaactc      60 tcctgtgcag cctctggatt cactttcagt gtctttggaa tgcactgggt tcgtcaggct    120
ccagagaagg ggctggagtg ggtcgcatac attagtagtg gcagtactat catctattat    180
gcagacacag tgaagggccg attcaccatc tccagagaca atcccaagaa cacctgttc     240 ctgcaaatga ccgtctaag gtctgaggac acggccatgt attactgtgc aagaccgctc     300
tactatgatt acgacgacta tgctatggac tactggggtc aaggaacctc agtcaccgtc    360
tcctca                                                               366

<210> SEQ ID NO 12
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Asp Val Gln Leu Val Glu Ser Gly Gly Gly Leu Val Gln Pro Gly Gly
1               5                   10                  15

Ser Arg Lys Leu Ser Cys Ala Ala Ser Gly Phe Thr Phe Ser Val Phe
            20                  25                  30

Gly Met His Trp Val Arg Gln Ala Pro Glu Lys Gly Leu Glu Trp Val
        35                  40                  45

Ala Tyr Ile Ser Ser Gly Ser Thr Ile Ile Tyr Tyr Ala Asp Thr Val
    50                  55                  60

Lys Gly Arg Phe Thr Ile Ser Arg Asp Asn Pro Lys Asn Thr Leu Phe
65                  70                  75                  80

Leu Gln Met Thr Gly Leu Arg Ser Glu Asp Thr Ala Met Tyr Tyr Cys
                85                  90                  95

Ala Arg Pro Leu Tyr Tyr Asp Tyr Asp Asp Tyr Ala Met Asp Tyr Trp
            100                 105                 110

Gly Gln Gly Thr Ser Val Thr Val Ser Ser
        115                 120

<210> SEQ ID NO 13
<211> LENGTH: 336
<212> TYPE: DNA

<213> ORGANISM: Artificial Sequence
<220> FEATURE:
<223> OTHER INFORMATION: Description of Artificial Sequence: Synthetic polynucleotide

<400> SEQUENCE: 13

```
gacattgtga tgtcacagtc tccatcctcc ctggctgtgt cagcaggaga gcaggtcact      60
atgagctgca aatccagtca gagtctgttc aacagtagaa cccgaaagaa ctacttggct    120
tggtaccagc agaaaccagg gcagtctcct aaactgctga tctactgggc atccactagg    180
gaatctgggg tccctgatcg cttcacaggc agtggatctg ggacagattt cactctcacc    240
atcagcagtg tgcaggctga agacctggca gtttattact gcaaacaatc ttataatctg    300
ctcacgttcg gtgctgggac caagctggag ctgaaa                              336
```

<210> SEQ ID NO 14
<211> LENGTH: 112
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 14

```
Asp Ile Val Met Ser Gln Ser Pro Ser Ser Leu Ala Val Ser Ala Gly
  1               5                  10                  15
Glu Gln Val Thr Met Ser Cys Lys Ser Ser Gln Ser Leu Phe Asn Ser
                 20                  25                  30
Arg Thr Arg Lys Asn Tyr Leu Ala Trp Tyr Gln Gln Lys Pro Gly Gln
             35                  40                  45
Ser Pro Lys Leu Leu Ile Tyr Trp Ala Ser Thr Arg Glu Ser Gly Val
         50                  55                  60
Pro Asp Arg Phe Thr Gly Ser Gly Ser Gly Thr Asp Phe Thr Leu Thr
 65                  70                  75                  80
Ile Ser Ser Val Gln Ala Glu Asp Leu Ala Val Tyr Tyr Cys Lys Gln
                 85                  90                  95
Ser Tyr Asn Leu Leu Thr Phe Gly Ala Gly Thr Lys Leu Glu Leu Lys
                100                 105                 110
```

<210> SEQ ID NO 15
<211> LENGTH: 360
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 15

```
caggtccaac tgcagcagcc tggggctgaa ctggtgaggc ctggggcttc agtgaaactg     60
tcctgcaagg cttctggcta caccttcacc agctactgga tgaactgggt gaagttgagg    120
cctggacaag gccttgaatg gattggtatg attgatcctt cagacagtga aacttactac    180
gatcaagtat tcaaggacaa ggccacattg actgttgaca aatcctccag cacagcctac    240
atgcatctca gcagcctgac atctgaggac tctgcggtct attactgtgc aagatggatt    300
acgactgatt cctatactat ggactactgg ggtcaaggaa cctcagtcac cgtctcctca    360
```

<210> SEQ ID NO 16
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Gln Val Gln Leu Gln Gln Pro Gly Ala Glu Leu Val Arg Pro Gly Ala
1               5                   10                  15

Ser Val Lys Leu Ser Cys Lys Ala Ser Gly Tyr Thr Phe Thr Ser Tyr
            20                  25                  30

Trp Met Asn Trp Val Lys Leu Arg Pro Gly Gln Gly Leu Glu Trp Ile
        35                  40                  45

Gly Met Ile Asp Pro Ser Asp Ser Glu Thr Tyr Tyr Asp Gln Val Phe
    50                  55                  60

Lys Asp Lys Ala Thr Leu Thr Val Asp Lys Ser Ser Ser Thr Ala Tyr
65                  70                  75                  80

Met His Leu Ser Ser Leu Thr Ser Glu Asp Ser Ala Val Tyr Tyr Cys
                85                  90                  95

Ala Arg Trp Ile Thr Thr Asp Ser Tyr Thr Met Asp Tyr Trp Gly Gln
            100                 105                 110

Gly Thr Ser Val Thr Val Ser Ser
        115                 120

<210> SEQ ID NO 17
<211> LENGTH: 335
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 17
gatgttgtga tgacccaaac tccactctcc ctgcctgtca gtcttggaga tcaagcctcc      60
atctcttgca gatctagtca gagccttgta cacagtaatg aaacccctat ttacattggt     120
acctgcagaa gccaggccag tctccaaagc tcctgatcta caaagtttcc aaccgatttt     180
ctggggtccc agacaggttc agtggcagtg gatcagggac agatttcaca ctcaagatca     240
gcagagtgga ggctgaggat ctgggagttt atttctgctc tcaaagtaca catgttcctc     300
cgacgttcgg tggaggcacc aagctggaaa tcaaa                                335

<210> SEQ ID NO 18
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

```
Ser Arg Val Glu Ala Glu Asp Leu Gly Val Tyr Phe Cys Ser Gln Ser
                85                  90                  95

Thr His Val Pro Pro Thr Phe Gly Gly Gly Thr Lys Leu Glu Ile Lys
            100                 105                 110
```

<210> SEQ ID NO 19
<211> LENGTH: 359
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 19

```
caggtccaac tgcagcagcc tggggctgag ctggtgaagc ctggggcttc agtgaagatg      60
tcctgcaagg cttctggcta caccttcacc agctactggg tgcactgggt gaagcagagg     120
cctggacaag gccttgagtg atcggagtg attgatcctt ctgatagtta ctactagcta      180
aatcaaaagt tcaagggcaa ggccacatta ctgtagacac atcctccagc acagcctaca     240
tgcagctcag cagcctgaca tctgaggact ctgcggtcta ttactgtaca agacactatg     300
atttcgacag ctggtacttc gatgtctggg gcgcaggga cacggtcacc gtctcctca      359
```

<210> SEQ ID NO 20
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

```
Gln Val Gln Leu Gln Gln Pro Gly Ala Glu Leu Val Lys Pro Gly Ala
 1               5                  10                  15

Ser Val Lys Met Ser Cys Lys Ala Ser Gly Tyr Thr Phe Thr Ser Tyr
            20                  25                  30

Trp Val His Trp Val Lys Gln Arg Pro Gly Gln Gly Leu Glu Trp Ile
        35                  40                  45

Gly Val Ile Asp Pro Ser Asp Ser Tyr Thr Ser Tyr Asn Gln Lys Phe
    50                  55                  60

Lys Gly Lys Ala Thr Leu Thr Val Asp Thr Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Thr Arg His Tyr Asp Phe Asp Ser Trp Tyr Phe Asp Val Trp Gly Ala
            100                 105                 110

Gly Thr Thr Val Thr Val Ser Ser
        115                 120
```

<210> SEQ ID NO 21
<211> LENGTH: 1415
<212> TYPE: DNA
<213> ORGANISM: Artificial Sequence
<220> FEATURE:
<223> OTHER INFORMATION: Description of Artificial Sequence:  Synthetic
      polynucleotide

<400> SEQUENCE: 21

```
tggagtttgg gctgagctgg cttttcttg tcgcgatttt aaaaggtgtc cagtgcgatg       60
tgcagctggt ggagtctggg ggaggcttag tgcagcctgg agggtccggg aaactctcct     120
```

```
gtgcagcctc tggattcact ttcagtgtct tggaatgca ctgggttcgt caggctccag    180
agaaggggct ggagtgggtc gcatacatta gtagtggcag tactatcatc tattatgcag    240
acacagtgaa gggccgattc accatctcca gagacaatcc aagaacacc ctgttcctgc    300 aaatgaccgg tctaaggtct gaggacacgg ccatgtatta ctgtgcaaga ccgctctact    360
atgattacga cgactatgct atggactact ggggtcaagg aacctcagtc accgtctcct    420
cagcgtcgac caagggccca tcggtcttcc cctggcacc ctcctccaag agcacctctg    480 gggcacagc ggccctgggc tgcctggtca aggactactt ccccgaaccg gtgacggtgt    540
cgtggaactc aggcgccctg accagcggcg tgcacacctt cccggctgtc ctacagtcct    600
caggactcta ctccctcagc agcgtggtga ccgtgccctc agcagcttg ggcacccaga    660 cctacatctg caacgtgaat cacaagccca gcaacaccaa ggtggacaag aaagttgagc    720
ccaaatcttg tgacaaaact cacacatgcc caccgtgccc agcacctgaa ctcctggggg    780
gaccgtcagt cttcctcttc cccccaaaac ccaaggacac cctcatgatc tcccggaccc    840
ctgaggtcac atgcgtggtg gtggacgtga gccacgaaga ccctgaggtc aagttcaact    900
ggtacgtgga cggcgtggag gtgcataatg ccaagacaaa gccgcgggag gagcagtaca    960
acagcacgta ccgtgtggtc agcgtcctca ccgtcctgca ccaggactgg ctgaatggca    1020
aggagtacaa gtgcaaggtc tccaacaaag ccctcccagc ccccatcgag aaaaccatct    1080
ccaaagccaa agggcagccc cgagaaccac aggtgtacac cctgccccca tcccgcgagg    1140
agatgaccaa gaaccaggtc agcctgacct gcctggtcaa aggcttctat cccagcgaca    1200
tcgccgtgga gtgggagagc aatgggcagc cggagaacaa ctacaagacc acgcctcccg    1260
tgctggactc cgacggctcc ttcttcctct acagcaagct caccgtggac aagagcaggt    1320
ggcagcaggg gaacgtcttc tcatgctccg tgatgcatga ggctctgcac aaccactaca    1380
cgcagaagag cctctccctg tctccgggta aatga                               1415
```

<210> SEQ ID NO 22
<211> LENGTH: 1415
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 22

```
tcatttaccc ggagacaggg agaggctctt ctgcgtgtag tggttgtgca gagcctcatg     60
catcacggag catgagaaga cgttcccctg ctgccacctg ctcttgtcca cggtgagctt    120
gctgtagagg aagaaggagc cgtcggagtc cagcacggga ggcgtggtct tgtagttgtt    180
ctccggctgc ccattgctct cccactccac ggcgatgtcg ctgggataga agcctttgac    240
caggcaggtc aggctgacct ggttcttggt catctcctcg cgggatgggg cagggtgta    300 cacctgtggt tctcggggct gcccttggc tttggagatg gttttctcga tggggctgg    360 gagggctttg ttggagacct tgcacttgta ctccttgcca ttcagccagt cctggtgcag    420
gacggtgagg acgctgacca cacggtacgt gctgttgtac tgctcctccc gcggctttgt    480
cttggcatta tgcacctcca cgccgtccac gtaccagttg aacttgacct cagggtcttc    540
gtggctcacg tccaccacca gcatgtgac ctcagggtc cgggagatca tgagggtgtc    600
cttgggtttt ggggggaaga ggaagactga cggtccccc aggagttcag gtgctgggca    660
cggtgggcat gtgtgagttt tgtcacaaga tttgggctca acttcttgt ccaccttggt    720
```

```
gttgctgggc ttgtgattca cgttgcagat gtaggtctgg gtgcccaagc tgctggaggg      780
cacggtcacc acgctgctga gggagtagag tcctgaggac tgtaggacag ccgggaaggt      840
gtgcacgccg ctggtcaggg cgcctgagtt ccacgacacc gtcaccggtt cggggaagta      900
gtccttgacc aggcagccca gggccgctgt gcccccagag gtgctcttgg aggagggtgc      960 caggggaag accgatgggc ccttggtcga cgctgaggag acggtgactg aggttccttg      1020
accccagtag tccatagcat agtcgtcgta atcatagtag agcggtcttg cacagtaata      1080
catggccgtg tcctcagacc ttagaccggt catttgcagg aacagggtgt tcttgggatt      1140
gtctctggag atggtgaatc ggcccttcac tgtgtctgca taatagatga tagtactgcc      1200
actactaatg tatgcgaccc actccagccc cttctctgga gcctgacgaa cccagtgcat      1260
tccaaagaca ctgaaagtga atccagaggc tgcacaggag agtttccggg accctccagg      1320
ctgcactaag cctcccccag actccaccag ctgcacatcg cactggacac cttttaaaat      1380
cgcgacaaga aaaagccagc tcagcccaaa ctcca                                 1415
```

```
<210> SEQ ID NO 23
<211> LENGTH: 725
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 23
tggacatgcg cgtgcccgcc cagctgctgg gcctgctgct gctgtggttc cccggctcgc       60
gatgctacat tgtgatgtca cagtctccat cctccctggc tgtgtcagca ggagagaagg      120
tcactatgag ctgcaaatcc agtcagagtc tgctcaacag tagaacccga aagaaccact      180
tggcttggta tcagcagaaa ccagggcagt ctcctaaact gctgatctac tgggcatcca      240
ctagggaatc tggggtccct gatcgcttca caggcagtgg atctgggaca gatttcgctc      300
tcaccatcag cagtgtgcag gctgaagacc tggcagtttta tttctgcaag caatcttata      360
atctgtacac attcggtgct gggaccaagc tggagctgaa acgtacggtg gctgcaccat      420
ctgtcttcat cttcccgcca tctgatgagc agttgaaatc tggaactgcc tctgttgtgt      480
gcctgctgaa taacttctat cccagagagg ccaaagtaca gtggaaggtg gataacgccc      540
tccaatcggg taactcccag gagagtgtca cagagcagga cagcaaggac agcacctaca      600
gcctcagcag caccctgacg ctgagcaaag cagactacga gaaacacaaa gtctacgcct      660
gcgaagtcac ccatcagggc ctgagctcgc ccgtcacaaa gagcttcaac aggggagagt      720
gttga                                                                  725
```

```
<210> SEQ ID NO 24
<211> LENGTH: 725
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 24
tcaacactct ccctgttga agctctttgt gacgggcgag ctcaggccct gatgggtgac       60
ttcgcaggcg tagactttgt gtttctcgta gtctgctttg ctcagcgtca gggtgctgct      120
gaggctgtag gtgctgtcct tgctgtcctg ctctgtgaca ctctcctggg agttacccga      180
ttggagggcg ttatccacct tccactgtac tttggcctct ctgggataga agttattcag      240
```

```
caggcacaca acagaggcag ttccagattt caactgctca tcagatggcg ggaagatgaa      300
gacagatggt gcagccaccg tacgtttcag ctccagcttg gtcccagcac cgaatgtgta      360
cagattataa gattgcttgc agaaataaac tgccaggtct tcagcctgca cactgctgat      420
ggtgagagcg aaatctgtcc cagatccact gcctgtgaag cgatcaggga ccccagattc      480
cctagtggat gcccagtaga tcagcagttt aggagactgc cctggtttct gctgatacca      540
agccaagtgg ttctttcggg ttctactgtt gagcagactc tgactggatt tgcagctcat      600
agtgaccttc tctcctgctg acacagccag ggaggatgga gactgtgaca tcacaatgta      660
gcatcgcgag ccggggaacc acagcagcag caggcccagc agctgggcgg gcacgcgcat      720
gtcca                                                                  725

<210> SEQ ID NO 25
<211> LENGTH: 321
<212> TYPE: DNA
<213> ORGANISM: Artificial sequence
<220> FEATURE:
<223> OTHER INFORMATION: Synthetic polynucleotide

<400> SEQUENCE: 1
gacatccaga tggaccagtc tccatccagt ctgtctgcat cccttggaga cacaattacc       60
atcacttgcc atgccagtca gaacattaat gtttggttaa gctggtacca gcagaaacca      120
ggaaatattc ctaaactatt gatctataag gcttccaact tgcacacagg cgtcccatca      180
aggtttagtg gcagtggatc tggaacaggt ttcacattaa ccatcagcag cctgcagcct      240
gaagacattg ccacttacta ctgtcaacag ggtcaaagtt atcctctcac gttcggctcg      300
gggcgaaagt tggaaataaa a                                                321

<210> SEQ ID NO 26
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 2

Asp Ile Gln Met Asp Gln Ser Pro Ser Ser Leu Ser Ala Ser Leu Gly
 1               5                  10                  15

Asp Thr Ile Thr Ile Thr Cys His Ala Ser Gln Asn Ile Asn Val Trp
            20                  25                  30

Leu Ser Trp Tyr Gln Gln Lys Pro Gly Asn Ile Pro Lys Leu Leu Ile
        35                  40                  45

Tyr Lys Ala Ser Asn Leu His Thr Gly Val Pro Ser Arg Phe Ser Gly
    50                  55                  60

Ser Gly Ser Gly Thr Gly Phe Thr Leu Thr Ile Ser Ser Leu Gln Pro
65                  70                  75                  80

Glu Asp Ile Ala Thr Tyr Tyr Cys Gln Gln Gly Gln Ser Tyr Pro Leu
                85                  90                  95

Thr Phe Gly Ser Gly Arg Lys Leu Glu Ile Lys
            100                 105

<210> SEQ ID NO 27
<211> LENGTH: 354
<212> TYPE: DNA
<213> ORGANISM: Artificial sequence
<220> FEATURE:
<223> OTHER INFORMATION: Artificial polynucleotide
```

```
<400> SEQUENCE: 3
gaggttcagc tgcagcagtc tggggcagag cttgtgaagc caggggcctc agtcaagttg      60
tcctgcacag cttctggctt caacattaaa gacacctata tgcactgggt gaagcagagg     120
cctgaacagg gcctggagtg gattggaagg attgatcctg cgaatggtaa tactaaatat     180
gacccgaagt tccagggcaa ggccactata acaacagaca catcctccaa cacagcctac     240
ctgcagctca gcagcctgac atctgaggac actgccgtct attactgtgc tacctcctac     300
tatggtaact acgttgctta ctggggccac gggactctgg tcactgtctc tgca           354

<210> SEQ ID NO 28
<211> LENGTH: 118
<212> TYPE: PRT
<213> ORGANISM: Artificial sequence
<220> FEATURE:
<223> OTHER INFORMATION: Artificial polypeptide

<400> SEQUENCE: 4

Glu Val Gln Leu Gln Gln Ser Gly Ala Glu Leu Val Lys Pro Gly Ala
 1               5                  10                  15

Ser Val Lys Leu Ser Cys Thr Ala Ser Gly Phe Asn Ile Lys Asp Thr
                20                  25                  30

Tyr Met His Trp Val Lys Gln Arg Pro Glu Gln Gly Leu Glu Trp Ile
            35                  40                  45

Gly Arg Ile Asp Pro Ala Asn Gly Asn Thr Lys Tyr Asp Pro Lys Phe
        50                  55                  60

Gln Gly Lys Ala Thr Ile Thr Thr Asp Thr Ser Ser Asn Thr Ala Tyr
 65                 70                  75                  80

Leu Gln Leu Ser Ser Leu Thr Ser Glu Asp Thr Ala Val Tyr Tyr Cys
                85                  90                  95

Ala Thr Ser Tyr Tyr Gly Asn Tyr Val Ala Tyr Trp Gly His Gly Thr
               100                 105                 110

Leu Val Thr Val Ser Ala
           115
```

ANTI-*T. CRUZI* ANTIBODIES AND METHODS OF USE

RELATED APPLICATION INFORMATION

This application is a continuation of U.S. Ser. No. 12/342,641 filed on Dec. 23, 2008, which claims the benefit of U.S. Application No. 61/017,071 filed Dec. 27, 2007, the contents of which are herein incorporated by reference.

TECHNICAL FIELD

The present disclosure relates to methods, assays and kits for detecting or quantifying *Trypanosoma (Schizotrypanum) cruzi* antigens.

BACKGROUND

The parasite *Trypanosoma (Schizotrypanum) cruzi* causes Chagas' disease (American trypanosomiasis) and is endemic in Central and South America, as well as in Mexico. After a mild acute phase, most infected victims enter an indeterminate phase that is characterized by a lack of symptoms, low parasite count, and low titers of anti-*T. cruzi* antibodies. Approximately 10-30% of persons with chronic *T. cruzi* infections, develop cardiac or gastrointestinal dysfunction. Chemotherapy can cure a substantial number of congenitally infected infants and children, but is largely ineffective in adults who harbor chronic infections (Coura, J., and S. de Castro. 2002. A critical review on Chagas disease chemotherapy. *Mem. Inst. Oswaldo Cruz.* 97:3-24). Roughly 25,000 of the estimated 12 million people in endemic countries who are chronically infected with *T. cruzi* die of the illness each year, due to cardiac rhythm disturbances or congestive heart failure (Kirchhoff, L. V. 2006. American trypanosomiasis (Chagas' disease). In *Tropical Infectious Diseases: Principles, Pathogens and Practice*. Vol. R. Guerrant, D. Walker, and P. Weller, editors. Churchill Livingstone, New York. 1082-1094).

Chagas was named after the Brazilian physician Carlos Chagas, who first described it in 1909 (Chagas, C. 1909a. Neue Trypanosomen. *Vorläufige Mitteilung. Arch. Schiff. Tropenhyg.* 13:120-122; Redhead, S. A., et al. 2006. *Pneumocystis* and *Trypanosoma cruzi*: nomenclature and typifications. *J Eukaryot Microbiol.* 53:2-11). He discovered that the intestines of Triatomidae harbored a flagellate protozoan, a new species of the *Trypanosoma* genus, and was able to prove experimentally that the parasite could be transmitted to marmoset monkeys that were bitten by the infected bug. Chagas named the pathogenic parasite that causes the disease *Trypanosoma cruzi* (Chagas, 1909a) and later that year as *Schizotrypanum cruzi* (Chagas, C. 1909b. Nova tripanozomiase humana: Estudos sobre a morfolojia e o ciclo evolutivo do *Schizotrypanum cruzi* n. gen., n. sp., ajente etiolojico de nova entidade morbida do homem. *Mem. Inst. Oswaldo Cruz.* 1:159-218), both names honoring Oswaldo Cruz, a Brazilian physician and epidemiologist who fought epidemics of yellow fever, smallpox, and bubonic plague at the turn of the 20th century.

Charles Darwin might have suffered from this disease as a result of a bite from the "Great Black Bug of the Pampas" he received east of the Andes near Mendoza. Darwin reported the episode in his diaries of the *Voyage of the Beagle*. Darwin was young and in general good health, though six months previously he had been ill for a month near Valparaiso, but in 1837, almost a year after he returned to England, he began to suffer intermittently from a strange group of symptoms, becoming incapacitated for much of the rest of his life.

In endemic areas, *T. cruzi* is transmitted mainly by blood-sucking triatomine insects. The disease can also be spread by blood transfusion, intravenous drug use, congenital transmission, by sexual activity, organ transplant or through breast milk (Bittencourt, A. L. 1976. Congenital Chagas disease. *Am J Dis Child.* 130:97-103; Cheng, K. Y., et al. 2007 Immunoblot assay using recombinant antigens as a supplemental test to confirm the presence of antibodies to *Trypanosoma cruzi. Clin Vaccine Immunol.* 14:355-61; Grant, I. H., et al. 1989. Transfusion-associated acute Chagas disease acquired in the United States. *Ann Intern Med.* 111:849-51; Hoff, R., et al. 1978. Congenital Chagas's disease in an urban population: investigation of infected twins. *Trans R Soc Trop Med Hyg.* 72:247-50; Kirchhoff, L. V. 1989. Is *Trypanosoma cruzi* a new threat to our blood supply? *Ann Intern Med.* 111:773-5; Skolnick, A. 1989. Does influx from endemic areas mean more transfusion-associated Chagas' disease? *Jama.* 262:1433). Currently, there is no vaccine against *T. cruzi*.

Diagnosis of chronic *T. cruzi* infection reflects the complexity of the parasite's life cycle. During periods of high fever, diagnosis consists simply of identifying the parasites in blood, cerebrospinal fluid, fixed tissue or lymph nodes; however, during latency and chronic stages of infection, the bug is difficult to detect. In xenodiagnosis, the intestinal contents of insect vectors are examined for *T. cruzi* several weeks after these parasites feed on the blood of a suspected patient. However, this procedure is laborious, expensive and lacks sensitivity (Segura, E. 1987. Xenodiagnosis. In Chagas' Disease Vectors. Vol. R. R. Brenner and A. M. Stoka, editors. CRC Press, Boca Raton, Fla. 41-45).

In contrast, serologic assays for antibodies to *T. cruzi* are well suited for rapid and inexpensive diagnosis of the infection. These methods include indirect immunofluorescence, indirect hemagglutination, complement fixation and enzyme immunoassay (Cheng, K. Y., et al. 2007 Immunoblot assay using recombinant antigens as a supplemental test to confirm the presence of antibodies to *Trypanosoma cruzi. Clin Vaccine Immunol.* 14:355-61). A persistent problem with conventional assays has been the occurrence of inconclusive and false-positive results (Almeida, I. C., et al. 1997. A highly sensitive and specific chemiluminescent enzyme-linked immunosorbent assay for diagnosis of active *Trypanosoma cruzi* infection. *Transfusion.* 37:850-7; Kirchhoff et al., 2006; Leiby, D. A., et al. 2000. Serologic testing for *Trypanosoma cruzi*: comparison of radioimmunoprecipitation assay with commercially available indirect immunofluorescence assay, indirect hemagglutination assay, and enzyme-linked immunosorbent assay kits. *J Clin Microbiol.* 38:639-42).

No assay has been uniformly accepted as the gold standard serologic diagnosis of *T. cruzi* infection (Cheng et al., 2007). Assays that are designed to detect *T. cruzi* DNA have been found to be insensitive (Gomes, M. L., et al. 1999. Chagas' disease diagnosis: comparative analysis of parasitologic, molecular, and serologic methods. *Am J Trop Med Hyg.* 60:205-10). A radioimmune precipitation assay (RIPA) that produces easily interpreted results was developed nearly two decades ago and has been suggested for use as a confirmatory test in the U.S. (Kirchhoff et al., 1989). Its sensitivity and specificity, however, have not been systematically validated. Moreover, the complexity of the RIPA render its widespread use outside of research settings difficult (Leiby et al., 2000).

Immunoassays designed to detect anti-*T. cruzi* antibodies present in patient samples can provide fast and reliable serological diagnostic methods. Typically, such diagnostic kits use one or more specific antibodies to act as calibrators, positive controls and/or panel members. Often, Chagas high-titer human plasma and/or serum is screened and spiked into the negative control reagent at specific quantities. Chagas quality control reagents, such as positive controls, are human plasma or serum samples screened for the presence of antibodies against specific epitopes. However, using human serum and plasma samples has several significant disadvantages. These include: (1) increasing regulatory concerns, (2) difficulty in sourcing large volume with high titer and specificity; (3) lot variability; (4) limitations regarding characterization; and (5) cost.

Thus, there remains a need in the art for specific antibodies to act as calibrators, positive controls and/or panel members. The present disclosure optionally overcomes or obviates some of the problems of current *T. cruzi* immunoassays (namely, increasing regulatory concerns, difficulty in sourcing large volume with high titer and specificity, lot variability, limitations regarding characterization, and cost) by providing novel antibodies, cell lines producing these antibodies, and methods of making these antibodies.

SUMMARY

An object of the disclosure is to provide antibodies, including, recombinant antibodies and chimeric antibodies, that specifically bind *Trypanosoma (Schizotrypanum) cruzi* antigens and uses thereof.

In accordance with one aspect of the present disclosure, there is provided recombinant antibodies, including chimeric antibodies, which are capable of specifically binding to a diagnostically relevant region of a *T. cruzi* protein. The antibodies, including chimeric and recombinant antibodies, selected from the group consisting of an antibody specific for *T. cruzi* polypeptides comprised by FP3, Pep2, FP10 and FRA.

In one aspect of the disclosure, the antibody is an said antibody is selected from the group consisting of:

(a) an antibody that specifically binds to a diagnostically relevant region of a *T. cruzi* polypeptide, wherein the *T. cruzi* polypeptide is FRA and further wherein said antibody has at last one binding constant selected from the group consisting of: an association rate constant ($k_a$) between about $7.0 \times 10^5$ $M^{-1}s^{-1}$ to about $7.0 \times 10^6 M^{-1}s^{-1}$, an dissociation rate constant ($k_d$) between about $4.0 \times 10^{-3}$ $s^{-1}$ to about $3.0 \times 10^{-1}$ $s^{-1}$ and an equilibrium dissociation constant ($K_D$) between about $5.7 \times 10^{-10}$ M to about $4.3 \times 10^{-7}$ M;

(b) an antibody that specifically binds to a diagnostically relevant region of a *T. cruzi* polypeptide, wherein the *T. cruzi* polypeptide is Pep2 and further wherein said antibody has at least one binding constant selected from the group consisting of: an association rate constant ($k_a$) between about $1.0 \times 10^6$ $M^{-1}s^{-1}$ to about $8.0 \times 10^6 M^{-1}s^{-1}$; an dissociation rate constant ($k_d$) between about $6.0 \times 10^{-3}$ $s^{-1}$ to about $4.0 \times 10^{-2}$ $s^{-1}$ and an equilibrium dissociation constant ($K_D$) between about $7.5 \times 10^{-10}$ M to about $4.0 \times 10^{-8}$ M;

(c) an antibody that specifically binds to a diagnostically relevant region of a *T. cruzi* polypeptide, wherein the *T. cruzi* polypeptide is FP10 and further wherein said antibody has at least one binding constant selected from the group consisting of: (a) an association rate constant ($k_a$) between about $5.0 \times 10^4 M^{-1}s^{-1}$ to about $3.0 \times 10^5$ $M^{-1}s^{-1}$; (b) an dissociation rate constant ($k_d$) between about $1.0 \times 10^{-4}$ $s^{-1}$ to about $8.0 \times 10^{-4}$ $s^{-1}$; and (c) an equilibrium dissociation constant ($K_D$) between about $3.3 \times 10^{-10}$ M to about $1.6 \times 10^{-8}$ M;

(d) an antibody that specifically binds to a diagnostically relevant region of a *T. cruzi* polypeptide, wherein the *T. cruzi* polypeptide is FP3 and further wherein said antibody has at least one binding constant selected from the group consisting of: an association rate constant ($k_a$) between about $2.0 \times 10^5$ $M^{-1}s^{-1}$ to about $6.0 \times 10^6 M^{-1}s^{-1}$; an dissociation rate constant ($k_d$) between about $2.0 \times 10^{-5}$ $s^{-1}$ to about $8.0 \times 10^{-4}$ $s^{-1}$; and an equilibrium dissociation constant ($K_D$) between about $3.3 \times 10^{-12}$ M to about $4.0 \times 10^{-9}$ M; and (e) any combinations of (a)-(d).

In another aspect of the disclosure, the antibody is a chimeric antibody expressed by a cell line, wherein the cell line selected from the group consisting of PTA-8136, PTA-8138 and PTA-8140. Optionally, the antibody is expressed by a cell line selected from the group consisting of PTA-8137, PTA-8139, PTA-8141, and PTA-8142. The antibodies optionally are monoclonal antibodies, humanized antibodies, single-chain Fv antibodies, affinity maturated antibodies, single chain antibodies, single domain antibodies, Fab fragments, F(ab') fragments, disulfide-linked Fv, and anti-idiotypic antibodies, dual-variable domain immunoglobulins (DVD-Ig®) or fragments thereof.

In another aspect of the disclosure, there is provided an immunodiagnostic reagent that comprises one or more of these antibodies, including chimeric and recombinant antibodies, which are capable of specifically binding a diagnostically relevant region of a *T. cruzi* protein, wherein the antibodies are selected from the group consisting of FP3, Pep2, FP10 and FRA.

In accordance with another aspect of the disclosure, the immunodiagnostic reagent comprises an antibody selected from the group consisting of:

(a) an antibody that specifically binds to a diagnostically relevant region of a *T. cruzi* polypeptide, wherein the *T. cruzi* polypeptide is FRA and further wherein said antibody has at last one binding constant selected from the group consisting of: an association rate constant ($k_a$) between about $7.0 \times 10^5$ $M^{-1}s^{-1}$ to about $7.0 \times 10^6 M^{-1}s^{-1}$, an dissociation rate constant ($k_d$) between about $4.0 \times 10^{-3}$ $s^{-1}$ to about $3.0 \times 10^{-1}$ $s^{-1}$ and an equilibrium dissociation constant ($K_D$) between about $5.7 \times 10^{-10}$ M to about $4.3 \times 10^{-7}$ M;

(b) an antibody that specifically binds to a diagnostically relevant region of a *T. cruzi* polypeptide, wherein the *T. cruzi* polypeptide is Pep2 and further wherein said antibody has at least one binding constant selected from the group consisting of: an association rate constant ($k_a$) between about $1.0 \times 10^6$ $M^{-1}s^{-1}$ to about $8.0 \times 10^6 M^{-1}s^{-1}$; an dissociation rate constant ($k_d$) between about $6.0 \times 10^{-3}$ $s^{-1}$ to about $4.0 \times 10^{-2}$ $s^{-1}$ and an equilibrium dissociation constant ($K_D$) between about $7.5 \times 10^{-10}$ M to about $4.0 \times 10^{-8}$ M;

(c) an antibody that specifically binds to a diagnostically relevant region of a *T. cruzi* polypeptide, wherein the *T. cruzi* polypeptide is FP10 and further wherein said antibody has at least one binding constant selected from the group consisting of: (a) an association rate constant ($k_a$) between about $5.0 \times 10^4 M^{-1}s^{-1}$ to about $3.0 \times 10^5$ $M^{-1}s^{-1}$: (b) an dissociation rate constant ($k_d$) between about $1.0 \times 10^{-4}$ $s^{-1}$ to about $8.0 \times 10^{-4}$ $s^{-1}$; and (c) an equilibrium dissociation constant ($K_D$) between about $3.3 \times 10^{-10}$ M to about $1.6 \times 10^{-8}$ M;

(d) an antibody that specifically binds to a diagnostically relevant region of a *T. cruzi* polypeptide, wherein the *T. cruzi* polypeptide is FP3 and further wherein said antibody has at least one binding constant selected from the group consisting of: an association rate constant ($k_a$) between about $2.0 \times 10^5$ $M^{-1}s^{-1}$ to about $6.0 \times 10^6 M^{-1}s^{-1}$; an dissociation rate constant ($k_d$) between about $2.0 \times 10^{-5}$ $s^{-1}$ to about $8.0 \times 10^{-4}$ $s^{-1}$; and an equilibrium dissociation constant ($K_D$) between about $3.3 \times 10^{-12}$ M to about $4.0 \times 10^{-9}$ M; and (e) any combinations of (a)-(d).

In accordance with another aspect of the disclosure, the immunodiagnostic reagent is selected from the group consisting of a detection reagent, a standardization reagent, and a positive control reagent.

In accordance with another aspect of the disclosure, there is provided antibodies, including chimeric and recombinant antibodies, which are capable of specifically binding to a diagnostically relevant region of a *T. cruzi* protein, the region comprising an epitope comprised by an amino acid sequence selected from the group consisting of an amino acid sequence having at least 80%, at least 90% and at least 95% sequence identity with an amino acid sequence as set forth in SEQ ID NO.:2, SEQ ID NO.:4, SEQ ID NO.:6 and SEQ ID NO.:8. In accordance with another aspect of the disclosure, the immunodiagnostic reagent that specifically binds to a diagnostically relevant region of a *T. cruzi* protein that comprises a chimeric antibody, wherein the chimeric antibody specifically binds to an epitope comprised by an amino acid sequence selected from the group consisting of an amino acid sequence substantially identical with an amino acid sequence as set forth in SEQ ID NO.:2, SEQ ID NO.:4, SEQ ID NO.:6 and SEQ ID NO.:8. The antibodies optionally are monoclonal antibodies, humanized antibodies, single-chain Fv antibodies, affinity maturated antibodies, single chain antibodies, single domain antibodies, Fab fragments, F(ab') fragments, disulfide-linked Fv, and anti-idiotypic antibodies, or fragments thereof. In accordance with another aspect of the disclosure, there is provided an immunodiagnostic reagent that comprises these antibodies.

In accordance with another aspect of the disclosure, there is provided antibodies, including chimeric and recombinant antibodies, and immunodiagnostic reagents comprising the antibodies, wherein the antibodies comprise a $V_H$ region selected from the group consisting of SEQ ID NO.:10, SEQ ID NO.:14, SEQ ID NO.:18 and SEQ ID NO.:28.

In accordance with another aspect of the disclosure, there is provided antibodies, including chimeric and recombinant antibodies, and immunodiagnostic reagents comprising the antibodies, wherein the antibodies comprise a $V_L$ region selected from the group consisting of SEQ ID NO.:12, SEQ ID NO.:16, SEQ ID NO.:20 and SEQ ID NO.:26.

In accordance with another aspect of the disclosure, there is provided antibodies, including chimeric and recombinant antibodies, and immunodiagnostic reagents comprising the antibodies, wherein the antibodies are selected from the group consisting of an antibody that comprises a $V_H$ region substantially identical to the sequence as set forth in SEQ ID NO.:10 and a $V_L$ region comprising an amino acid sequence substantially identical to the sequence as set forth in SEQ ID NO.:12; a $V_H$ region substantially identical to the sequence as set forth in SEQ ID NO.:14 and a $V_L$ region comprising an amino acid sequence substantially identical to the sequence as set forth in SEQ ID NO.:16; a $V_H$ region substantially identical to the sequence as set forth in SEQ ID NO.:18 and a $V_L$ region comprising an amino acid sequence substantially identical to the sequence as set forth in SEQ ID NO.:20; a $V_H$ region substantially identical to the sequence as set forth in SEQ ID NO.:28 and a $V_L$ region comprising an amino acid sequence substantially identical to the sequence as set forth in SEQ ID NO.:26. The antibodies optionally are monoclonal antibodies, humanized antibodies, single-chain Fv antibodies, affinity maturated antibodies, single chain antibodies, single domain antibodies, Fab fragments, F(ab') fragments, disulfide-linked Fv, and anti-idiotypic antibodies, or fragments thereof.

In accordance with another aspect of the disclosure, there is provided a cell line capable of expressing a chimeric antibody that specifically binds to a diagnostically relevant region of a *T. cruzi* protein, wherein the cell line optionally is selected from the group consisting of PTA-8136, PTA-8138 and PTA-8140. There is also provided a cell line that is capable of expressing an antibody that specifically binds to a diagnostically relevant region of a *T. cruzi* protein, wherein the cell line optionally is selected from the group consisting of PTA-8137, PTA-8139, PTA-8141 and PTA-8142.

In accordance with another aspect of the present disclosure, there is provided a method of standardizing a *T. cruzi* detection assay comprising using as a sensitivity panel an immunodiagnostic reagent optionally comprising one or more antibodies, including chimeric and recombinant antibodies, that are capable of specifically binding a diagnostically relevant region of a *T. cruzi* protein. In such a panel, optionally the one or more antibodies are selected from the group consisting of an antibody specific for FP3, Pep2, FP10 and FRA.

In accordance with another aspect of the present disclosure, there is provided a method for detecting the presence of *T. cruzi* antigens comprising contacting a test sample, such as a sample suspected of containing *T. cruzi* antigens, with an immunodiagnostic reagent comprising one or more antibodies, including chimeric and recombinant antibodies, which are capable of specifically binding a *T. cruzi* antigen. Optionally the contacting is done under conditions that allow formation of antibody:antigen complexes. Further optionally, the method comprises detecting any antibody:antigen complexes formed. The antibodies optionally are monoclonal antibodies, humanized antibodies, single-chain Fv antibodies, affinity maturated antibodies, single chain antibodies, single domain antibodies, Fab fragments, F(ab') fragments, disulfide-linked Fv, and anti-idiotypic antibodies, or fragments thereof.

In accordance with another aspect of the present disclosure, there is provided a method for detecting the presence of *T. cruzi* antibodies comprising contacting a test sample, such as a sample suspected of containing antibodies to *T. cruzi*, with one or more antigens specific for the *T. cruzi* antibodies. Optionally this contacting is done under conditions that allow formation of antigen:antibody complexes, and further optionally the method comprises detecting the antigen:antibody complexes. Still further, the method optionally comprises using an immunodiagnostic reagent comprising one or more antibodies, including chimeric and recombinant antibodies, wherein each of the antibodies are capable of specifically binding one of the antigens used in the method, e.g., either as a positive control or standardization reagent.

In accordance with another aspect of the present disclosure, there is provided a diagnostic kit for the detection of *T. cruzi* comprising an immunodiagnostic reagent comprising one or more antibodies, including recombinant and recombinant chimeric antibodies, which are capable of specifically binding a diagnostically relevant region of a *T. cruzi* protein. In such a kit, the one or more antibodies optionally are selected from the group consisting of an antibody, including chimeric and recombinant antibodies, specific for FP3, Pep2, FP10 and FRA. The antibodies optionally are monoclonal antibodies, humanized antibodies, single-chain Fv antibodies, affinity maturated antibodies, single chain antibodies, single domain antibodies, Fab fragments, F(ab') fragments, disulfide-linked Fv, and anti-idiotypic antibodies, or fragments thereof.

In accordance with yet another aspect of the present disclosure, there is provided isolated polypeptides that comprise a portion of a chimeric antibody that specifically binds to a diagnostically relevant region of a *T. cruzi* polypeptide selected from the group consisting of *T. cruzi* polypeptides comprised by FP3, Pep2, FP10 or FRA polypeptides. The chimeric antibody optionally is selected form the group consisting of a chimeric antibody that specifically binds an epitope comprised by an amino acid sequence selected from the group consisting of an amino acid sequence substantially identical with an amino acid sequence as set forth in SEQ ID NO.:2, SEQ ID NO.:4, SEQ ID NO.:6 and SEQ ID NO.:8. The isolated polypeptides optionally comprise a $V_H$ region selected from the group consisting of an amino acid sequence substantially identical to the sequence as set forth in SEQ ID NO.:10, SEQ ID NO.:14 SEQ ID NO.:18, and SEQ ID NO.:28. The isolated polypeptides optionally comprise a $V_L$ region selected from the group consisting of an amino acid sequence substantially identical to the sequence as set forth in SEQ ID NO.:12, SEQ ID NO.:16, SEQ ID NO.:20 and SEQ ID NO.:26. Further, the isolated polypeptides comprise both a $V_H$ and $V_L$ region selected from the group consisting of a $V_H$ region of SEQ ID NO.:10 and a $V_L$ region of SEQ ID NO.:12; $V_H$ region of SEQ ID NO.:14 and a $V_L$ region of SEQ ID NO.:16; $V_H$ region of SEQ ID NO.:18 and a $V_L$ region of SEQ ID NO.:20; and $V_H$ region of SEQ ID NO.:28 and a $V_L$ region of SEQ ID NO.:26.

In accordance with another aspect of the disclosure, there is provided isolated polynucleotides that encode a portion of a chimeric antibody that specifically binds to a diagnostically relevant region of a *T. cruzi* polypeptide, the *T. cruzi* polypeptide selected from the group consisting of *T. cruzi* polypeptides comprised by FP3, Pep2, FP10 and FRA polypeptides. The chimeric antibody optionally is selected form the group consisting of a chimeric antibody that specifically binds an epitope comprised by an amino acid sequence selected from the group consisting of an amino acid sequence substantially identical with an amino acid sequence as set forth in SEQ ID NO.:2, SEQ ID NO.:4, SEQ ID NO.:6 and SEQ ID NO.:8. The isolated polynucleotides optionally comprise a region that encodes a $V_H$ region selected from the group consisting of an amino acid sequence substantially identical to the sequence as set forth in SEQ ID NO.:10, SEQ ID NO.:14, SEQ ID NO.:18 and SEQ ID NO.:28. The isolated polynucleotides comprise a region that encodes a $V_L$ region selected from the group consisting of an amino acid sequence substantially identical to the sequence as set forth in SEQ ID NO.:12, SEQ ID NO.:16, SEQ ID NO.:20 and SEQ ID NO.:26. Further, the isolated polynucleotides comprise a region that encodes both a $V_H$ and $V_L$ region selected from the group consisting of a $V_H$ region of SEQ ID NO.:10 and a $V_L$ region of SEQ ID NO.:12; $V_H$ region of SEQ ID NO.:14 and a $V_L$ region of SEQ ID NO.:16; $V_H$ region of SEQ ID NO.:18 and a $V_L$ region of SEQ ID NO.:20; and $V_H$ region of SEQ ID NO.:28 and a $V_L$ region of SEQ ID NO.:26. In other aspects, the polynucleotide is one selected from the group consisting of SEQ ID NO.:9, SEQ ID NO.:11, SEQ ID NO.:13, SEQ ID NO.:15, SEQ ID NO.:17, SEQ ID NO.:19, SEQ ID NO.:25 and SEQ ID NO.:27.

In accordance with yet another aspect of the disclosure there is provided methods of purifying an antigen comprising a *T. cruzi* amino acid sequence comprised by the amino acid sequences as set forth in SEQ ID NOs.:1, 3, 5 or 7, comprising contacting a sample suspected of containing a *T. cruzi* polypeptide with an immunodiagnostic reagent, the immunodiagnostic reagent comprising one or more antibodies, including chimeric or recombinant antibodies, that are capable of specifically binding to a *T. cruzi* protein, under conditions that allow formation of antibody:antigen complexes, isolating the formed antibody:antigen complexes and separating the antigen from the antibody. Optionally, the antibody, including chimeric and recombinant antibodies, binds to a *T. cruzi* polypeptide selected form the group consisting of FP3, Pep2, FP10, and FRA.

These and other features, aspects, objects, and embodiments of the disclosure will become more apparent in the following detailed description in which reference is made to the appended drawings that are exemplary of such features, aspects, objects and embodiments.

BRIEF DESCRIPTION OF THE DRAWINGS

FIGS. 3A-C depicts the annotated, double-stranded polynucleotide sequence for VH and VL sequences (and flanking regions) cloned into Chagas 12-392-150 Mu-Hu_pBJ. FIG. 3A-B depicts the polynucleotide sequence (SEQ ID NOs.:21-22) for the Heavy chain signal peptide located at bases 2772-2828, VH gene sequences located at bases 2829-3194, and Human Constant IgG1, z, non-a sequences located at bases 3195-4187. FIG. 3C depicts the polynucleotide sequence (SEQ ID NOs.:23-24) for the Kappa signal peptide located at bases 7460-7525, the VL gene sequences located at bases 7526-7861, and the Human Constant kappa sequences located at bases 7862-8185.

DETAILED DESCRIPTION

Figure 1:
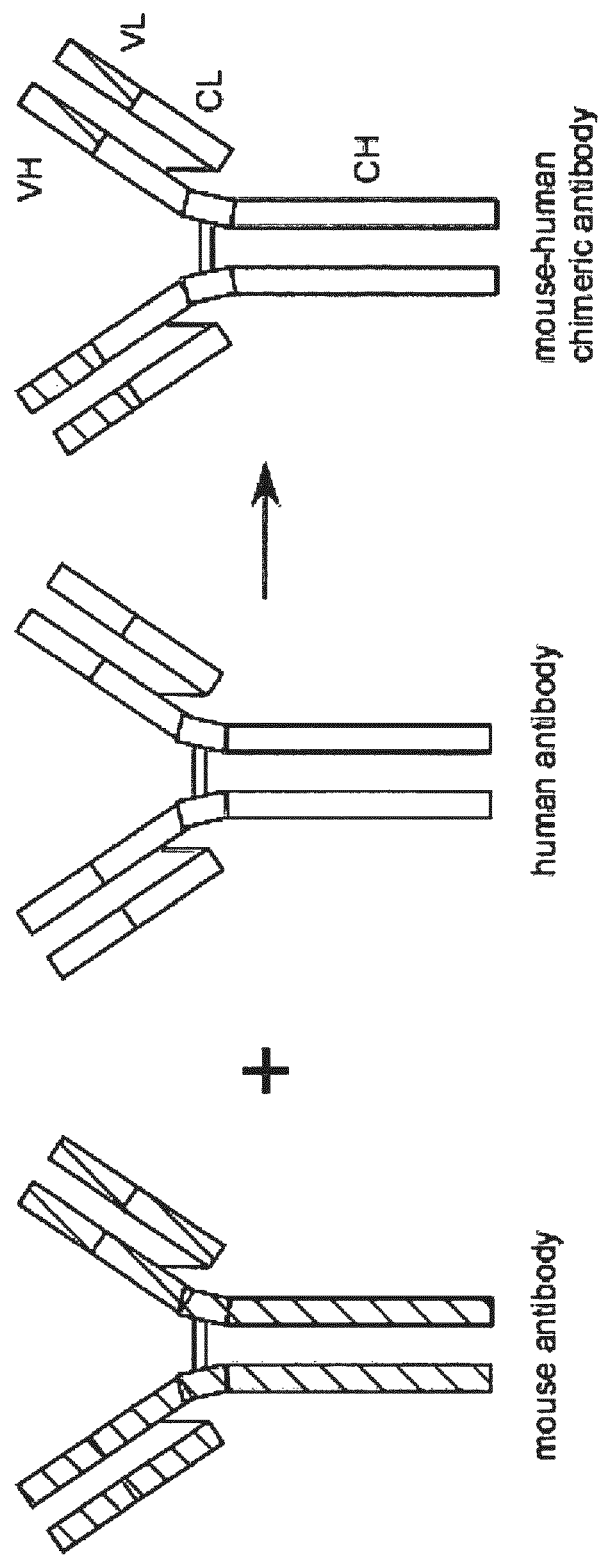
FIG. 1 presents a diagrammatic structure of the chimeric (mouse-human) anti-*T. cruzi* epitope antibodies of the disclosure.

The present disclosure provides, among other things, methods, assays and kits for detecting or quantifying *Trypanosoma* (*Schizotrypanum*) *cruzi* antigens. In accordance with one embodiment of the present disclosure, recombinant antibodies of the disclosure, including chimeric antibodies, specifically bind to diagnostically relevant regions of *T. cruzi* proteins and are thus suitable for use, for example, as diagnostic reagents for the detection of *T. cruzi*, and/or as standardization reagents or positive control reagents in assays for the detection of *T. cruzi*.

The present disclosure also thus provides for an immunodiagnostic reagent comprising one or more recombinant antibodies, including chimeric antibodies, wherein each antibody is capable of specifically binding a diagnostically relevant region of a *T. cruzi* protein. The recombinant antibodies can be, for example, chimeric antibodies, humanized antibodies, antibody fragments, and the like. In another embodiment, the immunodiagnostic reagent comprises two or more recombinant antibodies, including chimeric antibodies. Optionally the antibodies used in the immunodiagnostic reagent are each specific for a different *T. cruzi* antigenic protein, such that the immunodiagnostic reagent is capable of detecting a plurality of *T. cruzi* antigens. Optionally, the immunodiagnostic reagent comprises at least one or more, or at least two or more, recombinant antibodies specific for *T. cruzi* antigens selected from the group consisting of a recombinant antibody specific for Chagas FP3 antigen, a recombinant antibody specific for Chagas FP6 antigen, a recombinant antibody specific for Chagas FP10 antigen, and a recombinant antibody specific for Chagas FRA antigen. In yet another embodiment, the antibody or antibodies of the immunodiagnostic reagent are novel monoclonal antibodies produced by hybridoma cell lines and are specific for *T. cruzi* antigens selected from the group consisting of a monoclonal antibody specific for Chagas FP3 antigen, a monoclonal antibody specific for Chagas FP6 antigen, a monoclonal antibody specific for Chagas FP10 antigen, and a monoclonal antibody specific for Chagas FRA antigen.

In one embodiment, the present disclosure provides for the use of the immunodiagnostic reagent as a standardization reagent in a *T. cruzi* detection assay, for instance, in place of human sera. In this context, the immunodiagnostic reagent optionally can be used, for example, to evaluate and standardize the performance of current and future *T. cruzi* detection assays.

These and additional embodiments, features, aspects, illustrations, and examples of the disclosure are further described in the sections which follow. Unless defined otherwise herein, all technical and scientific terms used herein have the same meaning as commonly understood by one of ordinary skill in the art to which this disclosure belongs.

A. DEFINITIONS

As used herein, the singular forms "a," "an" and "the" include plural referents unless the context clearly dictates otherwise. For the recitation of numeric ranges herein, each intervening number there between with the same degree of precision is explicitly contemplated. For example, for the range 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9 and 7.0 are explicitly contemplated.

a) About

As used herein, the term "about" refers to approximately a +/−10% variation from the stated value. It is to be understood that such a variation is always included in any given value provided herein, whether or not it is specifically referred to.

b) Antibody

The term "antibody" (Ab) as used herein comprises single Abs directed against a TCA (an anti-TCA Ab), anti-TCA Ab compositions with poly-epitope specificity, single chain anti-TCA Abs, and fragments of anti-TCA Abs. A "monoclonal antibody" (mAb) is obtained from a population of substantially homogeneous Abs, i.e., the individual Abs comprising the population are identical except for possible naturally-occurring mutations that can be present in minor amounts. Exemplary Abs include polyclonal (pAb), monoclonal (mAb), humanized, bi-specific (bsAb), heteroconjugate Abs and dual-variable domain immunoglobulins (DVD-Ig®) and derivatives of dual-variable domain immunoglobulins (such as triple variable domains) (Dual-variable domain immunoglobulins and methods for making them are described in Wu, C., et al., *Nature Biotechnology,* 25(11):1290-1297 (2007) and WO2001/058956; the contents of each of which are herein incorporated by reference).

c) Antibody Fragment

The term "antibody fragment" or "antibody fragments," as used herein, refers to a portion of an intact antibody comprising the antigen binding site or variable region of the intact antibody, wherein the portion is free of the constant heavy chain domains (i.e., $C_H2$, $C_H3$, and $C_H4$, depending on antibody isotype) of the Fc region of the intact antibody. Examples of antibody fragments include, but are not limited to, Fab fragments, Fab' fragments, Fab'-SH fragments, $F(ab')_2$ fragments, Fv fragments, diabodies, single-chain Fv (scFv) molecules, single chain polypeptides containing only one light chain variable domain, single chain polypeptides containing the three CDRs of the light chain variable domain, single chain polypeptides containing only one heavy chain variable region, and single chain polypeptides containing the three CDRs of the heavy chain variable region.

d) Bifunctional Antibody

The term "bifunctional antibody," as used herein, refers to an antibody that comprises a first arm having a specificity for one antigenic site and a second arm having a specificity for a different antigenic site, i.e., the bifunctional antibodies have a dual specificity.

e) Biological Sample

The term "biological sample" includes tissues, cells and biological fluids isolated from a subject, as well as tissues, cells and fluids present within a subject. Biological samples from a subject contain polypeptide molecules. Examples of biological samples include whole blood, serum, plasma, interstitial fluid, saliva, ocular lens fluid, cerebral spinal fluid, sweat, urine, milk, ascites fluid, mucous, nasal fluid, sputum, synovial fluid, peritoneal fluid, vaginal fluid, menses, amniotic fluid and semen. Detection methods can be used to detect a TCA in a biological sample in vitro as well as in vivo. In vitro techniques for detection of a TCA include enzyme-linked immunosorbent assays (ELISAs), Western blots, immunoprecipitations and immunofluorescence. Furthermore, in vivo techniques for detecting a TCA include introducing into a subject a labeled anti-TCA antibody. For example, the antibody can be labeled with a radioactive marker whose presence and location in a subject can be detected by standard imaging techniques.

f) Binding Constants

The term "association rate constant", "$k_{on}$" or "$k_a$" as used interchangeably herein, refers to the value indicating the binding rate of an antibody to its target antigen or the rate of complex formation between an antibody and antigen as shown by the equation below:

Antibody("Ab")+Antigen("Ag")→Ab–Ag.

The term "dissociation rate constant", "$k_{off}$" or "$k_d$" as used interchangeably herein, refers to the value indicating the dissociation rate of an antibody from its target antigen or separation of Ab–Ag complex over time into free antibody and antigen as shown by the equation below:

Ab+Ag←Ab–Ag.

Methods for determining association and dissociation rate constants are well known in the art. Using fluorescence-based techniques offers high sensitivity and the ability to examine samples in physiological buffers at equilibrium. Other experimental approaches and instruments such as a BIAcore® (biomolecular interaction analysis) assay can be used (e.g., instrument available from BIAcore International AB, a GE Healthcare company, Uppsala, Sweden). Additionally, a KinExA® (Kinetic Exclusion Assay) assay, available from Sapidyne Instruments (Boise, Id.) can also be used.

The term "equilibrium dissociation constant" or "$K_D$" as used interchangeably, herein, refers to the value obtained by dividing the dissociation rate ($k_{off}$) by the association rate ($k_{on}$). The association rate, the dissociation rate and the equilibrium dissociation constant are used to represent the binding affinity of an antibody to an antigen.

g) Chimeric Antibody

The term "chimeric antibody" (or "cAb") as used herein, refers to a polypeptide comprising all or a part of the heavy and light chain variable regions of an antibody from one host species linked to at least part of the antibody constant regions from another host species.

h) Corresponding to or Corresponds to

The terms "corresponding to" or "corresponds to" indicate that a nucleic acid sequence is identical to all or a portion of a reference nucleic acid sequence. The term "complementary to" is used herein to indicate that the nucleic acid sequence is identical to all or a portion of the complementary strand of a reference nucleic acid sequence. For illustration, the nucleic acid sequence "TATAC" corresponds to a reference sequence "TATAC" and is complementary to a reference sequence "GTATA."

Unless otherwise specified herein, all nucleic acid sequences are written in a 5' to 3' direction, and all amino acid sequences are written in an amino- to carboxy-terminus direction.

i) Derivatized Antibody

The term "derivatized antibody" as used herein refers to an antibody or antibody portion that is derivatized or linked to another functional molecule. For example, an antibody or antibody fragment can be functionally linked, by chemical coupling, genetic fusion, or non-covalent association, etc., to one or more molecules, such as another antibody, a detectable agent, a cytotoxic agent, a pharmaceutical agent, and a polypeptide that can mediate association of the antibody or antibody portion with another molecule, such as a streptavidin core region or a polyhistidine tag. One type of derivatized antibody is produced by cross-linking two or more antibodies. Suitable cross-linkers include those that are hetero-bifunctional (e.g., m-maleimidobenzoyl-N-hydroxysuccinimide ester) or homo-bifunctional (e.g., disuccinimidyl suberate). Such linkers are available from Pierce Chemical Company (Rockford, Ill.).

j) Detectable Label

The term, "detectable labels", as used herein, include molecules or moieties that can be detected directly or indirectly. Furthermore, these agents can be derivatized with antibodies and include fluorescent compounds. Classes of labels include fluorescent, luminescent, bioluminescent, and radioactive materials, enzymes and prosthetic groups. Useful labels include horseradish peroxidase, alkaline phosphatase, β-galactosidase, acetylcholinesterase, streptavidin/biotin, avidin/biotin, umbelliferone, fluorescein, fluorescein isothiocyanate, rhodamine, dichlorotriazinylamine fluorescein, dansyl chloride, phycoerythrin, luminol, luciferase, luciferin, aequorin, and $^{125}I$, $^{131}I$, $^{35}S$ or $^3H$.

k) Diagnostically Relevant

The term "diagnostically relevant" as used herein with reference to a region of a *T. cruzi* protein refers to a region of the protein the detection of which, either alone or in combination with other diagnostically relevant regions of Chagas, allows detection of *T. cruzi*. Examples of diagnostically relevant regions include immunodominant regions known in the art and regions such as those described herein.

l) Epitope, Epitopes or Epitopes of Interest

As used herein, the term "epitope", "epitopes" or "epitopes of interest" refer to a site(s) on any molecule that is recognized and is capable of binding to a complementary site(s) on its specific binding partner. The molecule and specific binding partner are part of a specific binding pair. For example, an epitope can be a polypeptide, protein, hapten, carbohydrate antigen (such as, but not limited to, glycolipids, glycoproteins or lipopolysaccharides) or polysaccharide and its specific binding partner, can be, but is not limited to, an antibody. Typically an epitope is contained within a larger antigenic fragment (i.e., region or fragment capable of binding an antibody) and refers to the precise residues known to contact the specific binding partner. It is possible for an antigenic fragment to contain more than one epitope.

m) Humanized Antibody

The term "humanized antibody," as used herein, refers to a polypeptide comprising a modified variable region of a human antibody wherein a portion of the variable region has been substituted by the corresponding sequence from a non-human species and wherein the modified variable region is linked to at least part of the constant region of a human antibody. In one embodiment, the portion of the variable region is all or a part of the complementarity determining regions (CDRs). The term also includes hybrid antibodies produced by splicing a variable region or one or more CDRs of a non-human antibody with a heterologous protein(s), regardless of species of origin, type of protein, immunoglobulin class or subclass designation, so long as the hybrid antibodies exhibit the desired biological activity (i.e., the ability to specifically bind a *T. cruzi* antigenic protein).

n) Isolated or Purified

The term "isolated" or "purified", when referring to a molecule, refers to a molecule that has been identified and separated and/or recovered from a component of its natural environment. Contaminant components of its natural environment are materials that interfere with diagnostic or therapeutic use. The term "isolated" or "purified" polypeptide or biologically active fragment (such as an Fab fragment) as used herein refers to a polypeptide or biologically active fragment that is separated and/or recovered from a component of its environment. Contaminant components include materials that would typically interfere with diagnostic uses for the polypeptide, and can include enzymes, hormones, and other polypeptideaceous or non-polypeptideaceous materials. To be substantially isolated, preparations having less than about 30% by dry weight of contaminants (i.e., from about 0.01% to about 30%), usually less than about 20% (i.e., from about 0.01% to about 20%), less than about 10% (i.e., from about 0.01% to about 10%), and more often, less than about 5% (i.e., from about 0.01% to about 5%) contaminants. An isolated, recombinantly-produced TCA, $V_L$ or $V_H$ or biologically active portion is desirably substantially free of culture medium, i.e., culture medium represents less than about 20%, about 10%, or about 5% of the volume of the TCA, $V_L$ or $V_H$ preparation. Therefore, an "isolated antibody" as used herein refers to an antibody that is substantially free of other antibodies having different antigenic specificities. An isolated antibody that specifically binds a *T. cruzi* epitope can, however, have cross-reactivity to other *T. cruzi* antigens, such as, for example, an antibody that bind the Pep2 epitope, found on the Chagas polypeptides Tcf and FP6.

o) Quality Control Reagents

As described herein, immunoassays incorporate "quality control reagents" that include but are not limited to, e.g., calibrators, controls, and sensitivity panels. A "calibrator" or "standard" typically is used (e.g., one or more, or a plurality) in order to establish calibration (standard) curves for interpolation of antibody concentration. Optionally, a single calibrator can be used near the positive/negative cutoff. Multiple calibrators (i.e., more than one calibrator or a varying amount of calibrator(s)) can be used in conjunction so as to comprise a "sensitivity panel. A "positive control" is used to establish assay performance characteristics and is a useful indicator of the integrity of the reagents (e.g., antigens).

p) Recombinant Antibody or Recombinant Antibodies

The term "recombinant antibody" or "recombinant antibodies," as used herein, refers to an antibody prepared by one or more steps including cloning nucleic acid sequences encoding all or a part of one or more monoclonal antibodies into an appropriate expression vector by recombinant techniques and subsequently expressing the antibody in an appropriate host cell. The term thus includes, but is not limited to, recombinantly-produced antibodies that are monoclonal antibodies, antibody fragments including fragments of monoclonal antibodies, chimeric antibodies, humanized antibodies (fully or partially humanized), multispecific or multivalent structures formed from antibody fragments (including tetravalent IgG-like molecules termed dual-variable-domain immunoglobulin, DVD-Ig®), and bifunctional antibodies.

q) Specific or Specificity

As used herein, "specific" or "specificity" in the context of an interaction between members of a specific binding pair (e.g., an antigen and antibody) refers to the selective reactivity of the interaction. The phrase "specifically binds to" and analogous terms thereof refer to the ability of antibodies to specifically bind to a *T. cruzi* protein and not specifically bind to other entities. Antibodies or antibody fragments that specifically bind to a *T. cruzi* protein can be identified, for example, by diagnostic immunoassays (e.g., radioimmunoassays ("RIA") and enzyme-linked immunosorbent assays ("ELISAs")) (See, for example, Paul, ed., *Fundamental Immunology*, 2nd ed., Raven Press, New York, pages 332-336 (1989)), BIAcore® (biomolecular interaction analysis, instrument available from BIAcore International AB, Uppsala, Sweden), KinExA® (Kinetic Exclusion Assay, available from Sapidyne Instruments (Boise, Id.)) or other techniques known to those of skill in the art.

r) Substantially Identical

The term "substantially identical," as used herein in relation to a nucleic acid or amino acid sequence indicates that, when optimally aligned, for example using the methods described below, the nucleic acid or amino acid sequence shares at least about 70% (e.g., from about 70% to about 100%), at least about 75% (e.g., from about 75% to about 100%), at least about 80% (e.g., from about 80% to about 100%), at least about 85% (e.g., from about 85% to about 100%), at least about 90% (e.g., from about 90% to about 100%), at least about 95% (e.g., from about 95% to about 100%), at least about 96% (e.g., from about 96% to about 100%), at least about 97% (e.g., from about 97% to about 100%), at least about 98% (e.g., from about 98% to about 100%), or at least about 99% (e.g., from about 99% to about 100%) sequence identity with a defined second nucleic acid or amino acid sequence (or "reference sequence"). "Substantial identity" can be used to refer to various types and lengths of sequence, such as full-length sequence, epitopes or immunogenic peptides, functional domains, coding and/or regulatory sequences, exons, introns, promoters, and genomic sequences. Percent identity between two amino acid or nucleic acid sequences can be determined in various ways that are within the skill of a worker in the art, for example, using publicly available computer software such as Smith Waterman Alignment (Smith, T. F. and M. S. Waterman (1981) *J Mol Biol* 147:195-7); "BestFit" (Smith and Waterman, *Advances in Applied Mathematics*, 482-489 (1981)) as incorporated into GeneMatcher Plus™ Schwarz and Dayhof (1979) *Atlas of Protein Sequence and Structure, Dayhof,* M. O., Ed pp 353-358; BLAST program (Basic Local Alignment Search Tool (Altschul, S. F., W. Gish, et al. (1990) *J Mol Biol* 215: 403-10), and variations thereof including BLAST-2, BLAST-P, BLAST-N, BLAST-X, WU-BLAST-2, ALIGN, ALIGN-2, CLUSTAL, and Megalign (DNASTAR) software. In addition, those skilled in the art can determine appropriate parameters for measuring alignment, including algorithms needed to achieve maximal alignment over the length of the sequences being compared. In general, for amino acid sequences, the length of comparison sequences is at least about 10 amino acids. One skilled in the art understands that the actual length depends on the overall length of the sequences being compared and can be at least about 20, at least about 30, at least about 40, at least about 50, at least about 60, at least about 70, at least about 80, at least about 90, at least about 100, at least about 110, at least about 120, at least about 130, at least about 140, at least about 150, at least about 200, at least about 250, at least about 300, or at least about 350 amino acids, or it can be the full-length of the amino acid sequence. For nucleic acids, the length of comparison sequences is generally at least about 25 nucleotides, but can be at least about 50, at least about 100, at least about 125, at least about 150, at least about 200, at least about 250, at least about 300, at least about 350, at least about 400, at least about 450, at least about 500, at least about 550, at least about 600, at least about 650, at least about 700, at least about 800, at least about 900, or at least about 1000 nucleotides, or it can be the full-length of the nucleic acid sequence.

s) Surface Plasmon Resonance

The term "surface plasmon resonance" as used herein refers to an optical phenomenon that allows for the analysis of real-time biospecific interactions by detecting alterations in protein concentrations within a biosensor matrix, for example using the BIACORE® system (Biacore (GE Healthcare)) (Johnsson, B., et al. 1991. Immobilization of proteins to a carboxymethyldextran-modified gold surface for biospecific interaction analysis in surface plasmon resonance sensors.

*Anal Biochem.* 198:268-77; Johnsson, B., et al. 1995. Comparison of methods for immobilization to carboxymethyl dextran sensor surfaces by analysis of the specific activity of monoclonal antibodies. *J Mol Recognit.* 8:125-31; Jonsson, U., et al. 1993. Introducing a biosensor based technology for real-time biospecific interaction analysis. *Ann Biol Clin (Paris).* 51:19-26).

t) TCA

The abbreviation "TCA," as used herein, means "*T. cruzi* antigen." FP3, Pep2, TcF, FP6, and FP10 refer to TCAs and are further defined below. Other abbreviations are defined as they are introduced.

The terminology used herein is for the purpose of describing particular embodiments only and is not otherwise intended to be limiting.

B. ANTI-*T. CRUZI* ANTIBODIES AND CELL LINES PRODUCING SAME

The present disclosure provides, among other things, novel antibodies, cell lines producing these antibodies, and methods of making these antibodies. These antibodies bind various *T. cruzi* antigens (TCAs) and include those contained in the FP3, Pep2 (TcF, FP6) and FP10 polypeptides, and can be used as mAbs, such as mouse mAbs, dual-variable domain immunoglobulins (DVD-Ig®) or as chimeric antibodies, such as mouse-human (Mu-Hu) chimeras. These antibodies are useful as positive controls in immunoassays. Furthermore, the antibodies can be used to purify *T. cruzi* polypeptides that harbor the TCAs. Examples of antibodies and cell lines of the present disclosure are presented below in Table 1.

Further examples of antibodies of the present disclosure are antibodies that:

(a) that specifically binds to a diagnostically relevant region of a *T. cruzi* polypeptide, wherein the *T. cruzi* polypeptide is FRA and further wherein said antibody has at least one binding constant selected from the group consisting of: an association rate constant ($k_a$) between about $7.0 \times 10^5$ $M^{-1}s^{-1}$ to about $7.0 \times 10^6$ $M^{-1}s^{-1}$, an dissociation rate constant ($k_d$) between about $4.0 \times 10^{-3}$ $s^{-1}$ to about $3.0 \times 10^{-1}$ $s^{-1}$ and an equilibrium dissociation constant ($K_D$) between about $5.7 \times 10^{-10}$ M to about $4.3 \times 10^{-7}$ M;

(b) that specifically binds to a diagnostically relevant region of a *T. cruzi* polypeptide, wherein the *T. cruzi* polypeptide is Pep2 and further wherein said antibody has at least one binding constant selected from the group consisting of: an association rate constant ($k_a$) between about $1.0 \times 10^6$ $M^{-1}s^{-1}$ to about $8.0 \times 10^6$ $M^{-1}s^{-1}$; an dissociation rate constant ($k_d$) between about $6.0 \times 10^{-3}$ $s^{-1}$ to about $4.0 \times 10^{-2}$ $s^{-1}$ and an equilibrium dissociation constant ($K_D$) between about $7.5 \times 10^{-10}$ M to about $4.0 \times 10^{-8}$ M;

(c) that specifically binds to a diagnostically relevant region of a *T. cruzi* polypeptide, wherein the *T. cruzi* polypeptide is FP10 and further wherein said antibody has at least one binding constant selected from the group consisting of: (a) an association rate constant ($k_a$) between about $5.0 \times 10^4$ $M^{-1}s^{-1}$ to about $3.0 \times 10^5$ $M^{-1}s^{-1}$: (b) an dissociation rate constant ($k_d$) between about $1.0 \times 10^{-4}$ $s^{-1}$ to about $8.0 \times 10^{-4}$ $s^{-1}$; and (c) an equilibrium dissociation constant ($K_D$) between about $3.3 \times 10^{-10}$ M to about $1.6 \times 10^{-8}$ M;

(d) that specifically binds to a diagnostically relevant region of a *T. cruzi* polypeptide, wherein the *T. cruzi* polypeptide is FP3 and further wherein said antibody has at least one binding constant selected from the group consisting of: an association rate constant ($k_a$) between about $2.0 \times 10^5$ $M^{-1}s^{-1}$ to about $6.0 \times 10^6$ $M^{-1}s^{-1}$; an dissociation rate constant ($k_d$) between about $2.0 \times 10^{-5}$ $s^{-1}$ to about $8.0 \times 10^{-4}$ $s^{-1}$; and an equilibrium dissociation constant ($K_D$) between about $3.3 \times 10^{-12}$ M to about $4.0 \times 10^{-9}$ M; and (e) any combinations of (a)-(d).

To make the anti-*T. cruzi* antibodies and cell lines producing these antibodies as further described herein, generally a two-step process was followed: (1) hybridoma cell lines were developed that produced monoclonal antibodies that specifically bound to the antigens of interest—the *T. cruzi* epitopes (TCAs); and (2) chimeric antibodies were engineered using recombinant technologies, and then mammalian expression cell lines were used to produce the engineered antibodies. In this second part, after identifying hybridoma cell lines that secreted the desired mAbs, mRNA was isolated from these cells and the antibody gene sequences were identified. The variable light ($V_L$) and variable heavy ($V_H$) polynucleotide sequences were then cloned into pBOS vectors (supplying the human antibody sequences) that were then co-transfected in a transient expression system to confirm that the resulting chimeric antibodies were functional. Upon confirmation, the $V_L$ sequences were sub-cloned into the pJV plasmid, and the $V_H$ sequences into the pBV plasmid; these vectors where then used to construct a stable pBJ expression vector. CHO cells were then transfected with pBJ, transfectants selected, and the secreted antibodies tested again, allowing for industrial

TABLE 1

*T. cruzi* Antigens and antibody-producing cell lines summary[1]

| Antigen Name | Hybridoma cell line | | | CHO cell line | | |
|---|---|---|---|---|---|---|
| | Cell Line Name | Laboratory Name | ATCC Deposit* [Deposit Date] | Cell Line Name | Laboratory Name | ATCC Deposit* [Deposit Date] |
| FP3 | HBFP3 | Chagas FP3 12-392-150-110 | PTA-8139 [Jan. 24, 2007] | CHOFP3 | Chagas FP3 12-392-150CHO2580-104 | PTA-8136 [Jan. 24, 2007] |
| Pep2 (TcF, FP6) | HBPep2 | Chagas 9-638-132-115 | PTA-8137 [Jan. 24, 2007] | CHOPep2 | Chagas Pep2 9-638-1928 | PTA-8138 [Jan. 24, 2007] |
| FP10 | HBF10 | Chagas 10-745-140 | PTA-8141 [Jan. 24, 2007] | CHOFP10 | Chagas FP10 10-745-3796 | PTA-8140 [Jan. 24, 2007] |

[1]Another hybridoma cell line, laboratory name Chagas 8-367-171 and producing a mAb that binds recombinant FRA antigen, is deposited as PTA-8142 (also deposited on Jan. 24, 2007).
*All cell line deposits were made under the Budapest Treaty on the International Recognition of the Deposit of Microorganisms for the Purposes of Patent Procedure (Budapest Treaty) of Apr. 28, 1977 and amended on Sep. 26, 1980. American Type Culture Collection (ATCC); P.O. Box 1549; Manassas, VA 20108; USA.

scale production. Thus, the mouse $V_H$ and $V_L$ regions were combined with human constant chain (CH) and constant light chain (CL) regions to create exemplars of the chimeric antibodies of the disclosure. Therefore, the chimeric antibodies retain the mouse mAb functional specificity and affinity for the TCAs, but react in antibody assays that are designed to detect human immunoglobulin (Ig). In one embodiment, the disclosure is directed to monoclonal antibodies (mAbs) that specifically bind the TCAs FP3, Pep2 (FP6/Tcf), FP10 and FRA. Mice are individually immunized with the FP3, Pep2, FP10 or FRA recombinant antigens, antibody-producing mice are identified and euthanized, spleen cells are harvested and fused with myeloma cells, and mAb producing hybridoma cell lines are isolated.

C. IMMUNODIAGNOSTIC REAGENT

The immunodiagnostic reagent of the present disclosure comprises one or more antibodies described herein (See, for example, Sections B and E herein). For example the antibodies comprising the immunodiagnostic reagent can include recombinant antibodies, which also herein include recombinant chimeric antibodies, that specifically bind to a diagnostically relevant region of a T. cruzi protein. Therefore, in one embodiment, the immunodiagnostic reagent provided by the present disclosure comprises a single antibody capable of specifically binding a diagnostically relevant region of a T. cruzi protein. In other embodiments, the immunodiagnostic reagent provided by the present disclosure comprises a single chimeric antibody capable of specifically binding a diagnostically relevant region of a T. cruzi protein. In other embodiments, the immunodiagnostic reagent comprises a plurality of antibodies, which can include one or more recombinant antibodies, such as a recombinant chimeric antibody, each capable of specifically binding a diagnostically relevant region of a T. cruzi protein (e.g., either the same region, or a different region). One or more of the plurality of chimeric antibodies can be capable of specifically binding a diagnostically relevant region of the same T. cruzi protein. Alternatively, each of the plurality of chimeric antibodies can specifically bind a diagnostically relevant region of a different T. cruzi protein.

In one embodiment, of the present disclosure, the immunodiagnostic reagent is capable of detecting a plurality of T. cruzi antigens and optionally comprises two or more recombinant antibodies, each capable of specifically binding a different T. cruzi antigenic protein. In a further embodiment, the immunodiagnostic reagent optionally comprises three or more recombinant antibodies, each capable of specifically binding a different T. cruzi antigenic protein. In another embodiment, the immunodiagnostic reagent optionally comprises four or more recombinant antibodies, each capable of specifically binding a different T. cruzi antigenic protein.

The recombinant antibodies comprised by the immunodiagnostic reagent can optionally be modified, for example, for detection purposes, for immobilization onto a solid support, to improve stability and/or to improve pharmacokinetic properties, or by other means such as is known in the art.

D. T. CRUZI ANTIGENS

T. cruzi is a complex organism, with a complex life cycle. However, important antigens have been identified that are useful for the diagnostic detection of the parasite.

The FP3 antigen (Kirchhoff, L. V., and K. Otsu. U.S. Patent Application Publication No. 2004/0132077. 2004) is a recombinant protein the corresponds essentially to the combination of T. cruzi Ag15 (Otsu, K., et al. 1993. Interruption of a *Trypanosoma cruzi* gene encoding a protein containing 14-amino acid repeats by targeted insertion of the neomycin phosphotransferase gene. *Mol Biochem Parasitol.* 57:317-30) and T. cruzi Protein C, the latter being a flagellar calcium binding protein (Gonzalez, A., et al. 1985. Apparent generation of a segmented mRNA from two separate tandem gene families in *Trypanosoma cruzi*. *Nucleic Acids Res.* 13:5789-804). The polynucleotide sequence (SEQ ID NO.:1) and the polypeptide sequence (SEQ ID NO.:2) are shown below in Tables 2 and 3, respectively. The amino acid sequences specific to T. cruzi 14-amino acid repeats are underlined in Table 3, those amino acids corresponding to T. cruzi Protein A are in bold in Table 3, those amino acids corresponding to Protein B are in italics in Table 3 and those amino acids corresponding to Protein C are twice underscored in Table 3.

TABLE 2

| FP3 polynucleotide sequence (SEQ ID NO.: 1) |
|---|
| ATGGCCCAGC TCCAACAGGC AGAAAATAAT ATCACTAATT |
| CCAAAAAAGA AATGACAAAG CTACGAGAAA AAGTGAAAAA |
| GGCCGAGAAA GAAAAATTGG ACGCCATTAA CCGGGCAACC |
| AAGCTGGAAG AGGAACGAAA CCAAGCGTAC AAAGCAGCAC |
| ACAAGGCAGA GGAGGAAAAG GCTAAAACAT TTCAACGCCT |
| TATAACATTT GAGTCGGAAA ATATTAACTT AAAGAAAAGG |
| CCAAATGACG CAGTTTCAAA TCGGGATAAG AAAAAAAATT |
| CTGAAACCGC AAAAACTGAC GAAGTAGAGA AACAGAGGGC |
| GGCTGAGGCT GCCAAGGCCG TGGAGACGGA GAAGCAGAGG |
| GCAGCTGAGG CCACGAAGGT TGCCGAAGCG GAGAAGCGGA |
| AGGCAGCTGA GGCCGCCAAG GCCGTGGAGA CGGAGAAGCA |
| GAGGGCAGCT GAAGCCACGA AGGTTGCCGA AGCGGAGAAG |
| CAGAAGGCAG CTGAGGCCGC CAAGGCCGTG GAGACGGAGA |
| AGCAGAGGGC AGCTGAAGCC ACGAAGGTTG CCGAAGCGGA |
| GAAGCAGAGG GCAGCTGAAG CCATGAAGGT TGCCGAAGCG |
| GAGAAGCAGA AGGCAGCTGA GGCCGCCAAG GCCGTGGAGA |
| CGGAGAAGCA GAGGGCAGCT GAAGCCACGA AGGTTGCCGA |
| AGCGGAGAAG CAGAAGGCAG CTGAGGCCGC CAAGGCCGTG |
| GAGACGGAGA AGCAGAGGGC AGCTGAAGCC ACGAAGGTTG |
| CCGAAGCGGA GAAGCAGAAG GCAGCTGAGG CCGCCAAGGC |
| CGTGGAGACG GAGAAGCAGA GGGCAGCTGA AGCCACGAAG |
| GTTGCCGAAG CGGAGAAGGA TATCGATCCC ATGGGTGCTT |
| GTGGGTCGAA GGACTCGACG AGCGACAAGG GGTTGGCGAG |
| CGATAAGGAC GGCAAGAACG CCAAGGACCG CAAGGAAGCG |
| TGGGAGCGCA TTCGCCAGGC GATTCCTCGT GAGAAGACCG |
| CCGAGGCAAA ACAGCGCCGC ATCGAGCTCT TCAAGAAGTT |
| CGACAAGAAC GAGACCGGGA AGCTGTGCTA CGATGAGGTG |
| CACAGCGGCT GCCTCGAGGT GCTGAAGTTG GACGAGTTCA |

TABLE 2-continued

FP3 polynucleotide sequence (SEQ ID NO.: 1)

```
CGCCGCGAGT GCGCGACATC ACGAAGCGTG CATTCGACAA
GGCGAGGGCC CTGGGCAGCA AGCTGGAGAA CAAGGGCTCC
GAGGACTTTG TTGAATTTCT GGAGTTCCGT CTGATGCTGT
GCTACATCTA CGACTTCTTC GAGCTGACGG TGATGTTCGA
CGAGATTGAC GCCTCCGGCA ACATGCTGGT TGACGAGGAG
GAGTTCAAGC GCGCCGTGCC CAGGCTTGAG GCGTGGGGCG
CCAAGGTCGA GGATCCCGCG GCGCTGTTCA AGGAGCTCGA
TAAGAACGGC ACTGGGTCCG TGACGTTCGA CGAGTTTGCT
GCGTGGGCTT CTGCAGTCAA ACTGGACGCC GACGGCGACC
CGGACAACGT GCCGGAGAGC CCGAGACCGA TGGGAATC
```

TABLE 3

FP3 polypeptide sequence (SEQ ID NO.: 2)

MAQLQQAENN ITNSKKEMTK LREKVKKAEK EKLDAINRAT

KLEEERNQAY KAAHKAEEEK AKTFQRLITF ESENINLKKR

PNDAVSNRDK KKNSETAKTD EV

*EKQRAAEAAKAVET*

*EKRAAEATKVAEA*

*EKRKAAEAAKAVET*

*EKQRAAEATKVAEA*

*EKQKAAEAAKAVET*

*EKQRAAEATKVAEA*

*EKQRAAEAMKVAEA*

*EKQKAAEAAKAVET*

*EKQRAAEATKVAEA*

*EKQKAAEAAKAVET*

*EKQRAAEATKVAEA*

*EKQKAAEAAKAVET*

*EKQRAAEATKVAEA*

EKDIDP MGACGSKDST SDKGLASDKD GKNAKDRKEA WERIRQAIPR

EKTAEAKQRR IELFKKFDKN ETGKLCYDEV HSGCLEVLKL

DEFTPRVRDI TKRAFDKARA LGSKLENKGS EDFVEFLEFR

LMLCYIYDFF ELTVMFDEID ASGNMLVDEE EFKRAVPRLE

AWGAKVEDPA ALFKELDKNG TGSVTFDEFA AWASAVKLDA

DGDPDNVPES PRPMGI

The Pep2 antigen (Kirchhoff and Otsu, 2004) is a recombinant protein of repeated sequences of *T. cruzi*. FP6 and Tcf, *T. cruzi* polypeptides, both have the Pep2 antigen. The polynucleotide sequence (SEQ ID NO.:3) and polypeptide sequence (SEQ ID NO.:4) is shown in Tables 4 and 5, respectively.

TABLE 4

Pep2 polynucleotide sequence (SEQ ID NO.: 3)

```
GGTGACAAAC CATCACCATT TGGACAGGCC GCAGCAGGTG
ACAAACCATC ACCATTTGGA CAGGCC
```

TABLE 5

Pep2 polypeptide sequence (SEQ ID NO.: 4)

GDKPSPFGQA AAGDKPSPFG QA

The FP10 antigen (Kirchhoff and Otsu, 2004) is another recombinant protein of repeated sequences of *T. cruzi*. Its polynucleotide (SEQ ID NO.:5) and polypeptide (SEQ ID NO.:6) sequences are shown below in Tables 6 and 7, respectively. The amino acid sequence of the I-domain is underlined in Table 7, the amino acid sequence of the J-domain is in italics in Table 7, the amino acid sequence of the K-domain is in bold in Table 7 and the amino acid sequence of the L-domain are twice underscored in Table 7.

TABLE 6

FP10 polynucleotide sequence (SEQ ID NO.: 5)

```
GATCCAACGT ATCGTTTTGC AAACCACGCG TTCACGCTGG
TGGCGTCGGT GACGATTCAC GAGGTTCCGA GCGTCGCGAG
TCCTTTGCTG GGTGCGAGCC TGGACTCTTC TGGTGGCAAA
AAACTCCTGG GGCTCTCGTA CGACGAGAAG CACCAGTGGC
AGCCAATATA CGGATCAACG CCGGTGACGC CGACCGGATC
GTGGGAGATG GGTAAGAGGT ACCACGTGGT TCTTACGATG
GCGAATAAAA TTGGCTCCGT GTACATTGAT GGAGAACCTC
TGGAGGGTTC AGGGCAGACC GTTGTGCCAG ACGAGAGGAC
GCCTGACATC TCCCACTTCT ACGTTGGCGG GTATGGAAGG
AGTGATATGC CAACCATAAG CCACGTGACG GTGAATAATG
TTCTTCTTTA CAACCGTCAG CTGAATGCCG AGGAGATCAG
GACCTTGTTC TTGAGCCAGG ACCTGATTGG CACGGAAGCA
CACATGGGCA GCAGCAGCGG CAGCAGTGCC CACGGTACGC
CCTCGATTCC CGTTGACAGC AGTGCCCACG GTACACCCTC
GACTCCCGTT GACAGCAGTG CCCACGGTAC GCCCTCGACT
CCCGTTGACA GCAGTGCCCA CGGTACACCC TCGACTCCCG
TTGACAGCAG TGCCCACGGT ACACCCTCGA CTCCCGTTGA
CAGCAGTGCC CACGGTAAGC CCTCGACTCC CGCTGACAGC
AGTGCCCACA GTACGCCCTC GACTCCCGCT GACAGCAGTG
CCCACAGTAC GCCCTCAATT CCCGCTGACA GCAGTGCCCA
CAGTACGCCC TCAGCTCCCG CTGACAACGG CGCCAATGGT
ACGGTTTTGA TTTTGTCGAC TCATGACGCG TACAGGCCCG
TTGATCCCTC GGCGTACAAG CGCGCCTTGC CGCAGGAAGA
GCAAGAGGAT GTGGGGCCGC GCCACGTTGA TCCGACCAC
```

TABLE 6-continued

FP10 polynucleotide sequence (SEQ ID NO.: 5)

TTCCGCTCGA CCTCGACGAC TCATGACGCG TACAGGCCCG

TTGATCCCTC GGCGTACAAG CGCGCCTTGC CGCAGGAAGA

GCAAGAGGAT GTGGGCCGC GCCACGTTGA TCCCGACCAC

TTCCGCTCGA CGACTCATGA CGCGTACAGG CCCGTTGATC

CCTCGGCGTA CAAGCGCGCC TTGCCGCAGG AAGAGCAAGA

GGATGTGGGG CCGCGCCACG TTGATCCCGA CCACTTCCGC

TCGACCTCGA CGACTCATGA CGCGTACAGG CCCGTTGATC

CCTCGGCGTA CAAGCGCGCC TTGCCGCAGG AAGAGCAAGA

GGATGTGGGG CCGCGCCACG TTGATCCCGA CCACTTCCGC

TCGACCTCGA CGACTCATGA CGCGTACAGG CCCGTTGATC

CCTCGGCGTA CAAGCGCGCC TTGCCGCAGG AAGAGCAAGA

GGATGTGGGG CCGCGCCACG TTGATCCCGA CCACTTCCGC

TCGACGACTC ATGACGCGTA CAGGCCCGTT GATCCCTCGG

CGTACAAGCG CGCCTTGCCG CAGGAAGAGC AAGAGGATGT

GGGGCCGCGC CACGTTGATC CGACCACTT CCGCTCG

TABLE 7

FP10 polypeptide sequence (SEQ ID NO.: 6)

DPTYRFANHA FTLVASVTIH EVPSVASPLL GASLDSSGGK

KLLGLSYDEK HQWQPIYGST PVTPTGSWEM GKRYHVVLTM

ANKIGSVYID GEPLEGSGQT VVPDERTPDI SHFYVGGYGR

SDMPTISHVT VNNVLLYNRQ LNAEEIRTLF LSQDLIGTEA

HMGSSSG

SSAHGTPSIPVD

SSAHGTPSTPVD

SSAHGTPSTPVD

SSAHGTPSTPVD

SSAHGTPSTPVD

SSAHGKPSTPAD

SSAHSTPSTPAD

SSAHSTPSIPAD

SSAHSTPSAPAD

NGANGTV LILSTHDAYR PVDPSAYKRA LPQEEQEDVG

PRHVDPDHFR STSTTHDAYR PVDPSAYKRA LPQEEQEDVG

PRHVDPDHFR STTHDAYRPV DPSAYKRALP QEEQEDVGPR

HVDPDHFRST STTHDAYRPV DPSAYKRALP QEEQEDVGPR

HVDPDHFRST STTHDAYRPV DPSAYKRALP QEEQEDVGPR

HVDPDHFRST THDAYRPVDP SAYKRALPQE EQEDVGPRHV

DPDHFRS

The FRA antigen is a flagellar repetitive protein sequence (Lafaille, J. J., etc. 1989. Structure and expression of two *Trypanosoma cruzi* genes encoding antigenic proteins bearing repetitive epitopes. *Mol Biochem Parasitol.* 35:127-36), GenBank Accession J04015, is shown below in Table 8 (polynucleotide sequence, SEQ ID NO.:7) and 9 (polypeptide sequence; SEQ ID NO.:8).

TABLE 8

FRA polynucleotide sequence (SEQ ID NO.: 7)

ATGGAGTCAG GAGCGTCAGA TCAGCTGCTC GAGAAGGACC

CGCGTCAGGA ACGCGAAGGA GATTGCTGCG CTTGAGGAGA

GTCATGAATG CCCGCGTCAT CAGGAGCTGG CGCGCGAGAA

GAAGCTTGCC GACCGCGCGT TCCTTGACTC AGAAGCCGGA

GCGCGTGCCG CTGGCTGACG TGCCGCTCGA CGACGATCAG

CGACTTTGTT GCG

TABLE 9

FRA polypeptide sequence (SEQ ID NO.: 8)

MEQERRQLLE KDPRRNAKEI AALEESMNAR AQELAREKKL

ADRAFLDQKP ERVPLADVPL DDDSDFVA

The TCAs of SEQ ID NOs.:2, 4, 6 and 8 can be either synthesized in vitro or expressed recombinantly from the polynucleotide sequences, such as those substantially similar to SEQ ID NOs.:1, 3, 5 and 7. Because of redundancy in the genetic code and the ability for the polypeptides of SEQ ID NOs.:2, 4, 6 and 8 to tolerate substitutions, the sequences need not be identical to practice the disclosure. Polynucleotide and polypeptide sequence identities can range from about 70% to about 100% (especially from about from about 90% to about 97%), such as about 70%, about 75%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% and of course, about 100%.

The TCAs can be readily synthesized in vitro using polypeptide chemistry. For example, polypeptide synthesis can be carried out in a stepwise manner on a solid phase support using an automated polypeptide synthesizer, such as a Rainin Symphony Peptide Synthesizer, Advanced Chemtech Peptide Synthesizer, Argonaut Parallel Synthesis System, or an Applied Biosystems Peptide Synthesizer. The peptide synthesizer instrument combines the Fmoc chemistry with HOBt/HBTU/DIEA activation to perform solid-phase peptide synthesis.

Synthesis starts with the C-terminal amino acid, wherein the carboxyl terminus is covalently linked to an insoluble polymer support resin. Useful resins can load 0.1 mmol to 0.7 mmol of C-terminal amino acid per gram of resin; display resistance to the various solvents and chemicals used during a typical synthetic cycle, such as dichloromethane (DCM), N,N-dimethylformamide (DMF), N-methylpyrrolidone (NMP), N,N-dimethylamine (DMA), 1-Hydroxybenzotriazole (HOBt), 2-(1-H-Benzotriazol-1-yl)-1,1,3,3-tetramethyluronium hexafluorophosphate (HBTU), N,N-di-isopropylethylamine (DIEA), methanol (MeOH), or water; and be amenable to continuous flow or batch synthesis applications.

Examples of useful resins include p-Benzyloxybenzyl Alcohol resin (HMP resin), PEG co-Merrifield resin, NovaSyn TGA® resin (Novabiochem), 4-sulfamylbutyryl AM resin, and CLEAR amide resin. Amino acid-coupled resins are commercially available from a number of different sources, although such coupled resins can also be prepared in the lab.

The N-terminus of the resin-coupled amino acid (or polypeptide) is chemically-protected by a 9-fluorenylmethyloxycarbonyl (Fmoc) group that is removed prior to the addition of the next N-terminal amino acid reactant. The Fmoc group is a base labile protecting group that is easily removed by concentrated solutions of amines, such as 20-55% piperidine, in a suitable solvent, such as NMP or DMF. Other useful amines for Fmoc deprotection include tris(2-aminoethyl) amine, 4-(aminomethyl)piperidine, tetrabutylammonium fluoride, and 1,8-diazabicyclo[5.4.0]undec-7-ene (DBU). Complete removal of the Fmoc group from the N-terminus is important so that all resin-coupled polypeptide chains effectively participate in each coupling cycle; otherwise, polypeptide chains of heterogeneous length and sequence will result. Following base-catalyzed removal of the Fmoc group, the resin is extensively washed with a suitable buffer to remove the base catalyst.

The side chains of many amino acids contain chemically reactive groups, such as amines, alcohols, or thiols. These side chains must be additionally protected to prevent undesired side-reactions during the coupling step. Side chain protecting groups that are base-stable, more preferably, both base-stabile and acid-labile are most useful. Table 10 provides an exemplary set of side chain protection groups for this category of amino acids.

TABLE 10

| Side chain protection reagents | |
|---|---|
| Side chain protection | Amino acid |
| t-butyl ether | Ser, Thr, Tyr; |
| t-butyl ester | Glu and Asp |
| Trityl | Cys, His, Asn, and Gln |
| 2,2,5,7,8-pentamethylchromane-6-sulfonyl | Arg |
| butoxycarbonyl (tBoc) | Lys |

The carboxylate group of the incoming Fmoc-protected amino acid is activated in order to achieve efficient chemical coupling to the N-terminus of the resin-bound polypeptide. Activation is typically accomplished by reacting an Fmoc-protected amino acid with a suitable reagent to yield a reactive ester. Examples of activated esters include the pentafluorophenyl (OPfp) ester and the 3-hydroxy-2,3-dihydro-4-oxo-benzo-triazone (ODhbt) ester, OBt ester, and the OAt ester derived from 1-hydroxy-7-azabenzotriazole (HOAt). The coupling reactions can be done in situ using activating reagents, such as DCC, BOP, BOP-Cl, TBTU, HBTU or O-(7-azabenzotriazol-1-yl)-1,1,3,3, tetramethyluronium hexafluorophosphate (HATU). Exemplary coupling reactions included a mixture of HOBt and HBTU, or a mixture of HOBt, HBTU, and DIEA. For N-methyl amino acids, coupling conditions can use bromo-tris-pyrrolidino-phosphonium hexafluorophosphate (PyBroP) as the only coupling reagent, and the coupling reaction is performed manually in DCM with DIEA present under $N_2$. The Fmoc-protected amino acid is present in molar excess to the polypeptide coupled to the resin. For coupling reactions that proceed with a slow rate, the coupling reactions are repeated one or more times (double or multiple coupling) to ensure that all resin-bound polypeptide has undergone a successful addition reaction with the activated Fmoc-amino acid. For incomplete coupling reactions, any unreacted N-terminal residues are capped using a suitable capping reagent.

Following the coupling reaction, the resin support is washed to remove the unreacted Fmoc-amino acids and coupling reagents. The resin is then subjected to a new cycle of base-catalyzed removal of the N-terminal Fmoc group to prepare the polypeptide for another amino acid addition. After the desired polypeptide has been synthesized, the resin is subjected to base-catalyzed removal of the remaining Fmoc protection group. The polypeptide-coupled resin is washed to remove the base and subsequently treated with acid to remove any amino acid side chain protecting groups and to release the polypeptide chain from the resin support. Useful acids are strong acids, such as trifluoroacetic acid (TFA) in the presence of suitable scavengers, such as reagent K [TFA:thioanisole:ethanedithiol:phenol:water (82.5:5:2.5:5:5)].

The polypeptide is subsequently separated from the resin by filtration and optionally washed repeatedly with a suitable solvent, such as DCM/DMF. The polypeptide can be optionally desalted through ultrafiltration using a membrane with a suitable MW cutoff. The polypeptide can be precipitated from solution using a suitable solvent, such as cold methyl t-butyl ether or t-butylethylether, and the precipitate optionally washed with a suitable solvent, such as cold ether and dried. The polypeptide can be further purified using a suitable chromatographic means, such as hydrophobic chromatography using a C18 resin and an appropriate chromatographic buffer system, such as TFA/water/acetonitrile. The purity of the peptide optionally can be analyzed by mass spectrometry, such as MALDI-MS, analytical HPLC, amino acid analysis or sequencing.

Alternatively, the TCAs of SEQ ID NOs.:2, 4, 6, and 8 can be expressed recombinantly using the polynucleotide sequences of SEQ ID NOs.:1, 3, 5 and 7 using, for example, expression vectors. In expression vectors, the introduced DNA is operably-linked to elements, such as promoters, that signal to the host cell to transcribe the inserted DNA. Some promoters are exceptionally useful, such as inducible promoters that control gene transcription in response to specific factors. Examples of inducible promoters include those that are tissue-specific, which relegate expression to certain cell types, steroid-responsive (e.g., glucocorticoids (Kaufman, R. J. 1990. Vectors used for expression in mammalian cells. *Methods Enzymol.* 185:487-511) and tetracycline, or heat-shock reactive. Some bacterial repression systems, such as the lac operon, can be exploited in mammalian cells and transgenic animals (Fieck, A., et al. 1992. Modifications of the *E. coli* lac repressor for expression in eukaryotic cells: effects of nuclear signal sequences on protein activity and nuclear accumulation. *Nucleic Acids Res.* 20:1785-91; Wyborski, D. L., L. C. DuCoeur, and J. M. Short. 1996). Parameters affecting the use of the lac repressor system in eukaryotic cells and transgenic animals. *Environ Mol Mutagen.* 28:447-58; Wyborski, D. L., and J. M. Short. 1991. Analysis of inducers of the *E. coli* lac repressor system in mammalian cells and whole animals. *Nucleic Acids Res.* 19:4647-53). Recombinant nucleic acid technologies, transfection into cells and cellular and in vitro expression are discussed further below.

E. RECOMBINANT ANTIBODIES

The recombinant antibodies of the present disclosure comprise antigen-binding regions derived from the $V_H$ and/or $V_L$ domains of a native antibody capable of specifically binding to a *T. cruzi* antigenic protein. The recombinant antibody can be, for example, a recombinantly-produced monoclonal antibody, a fragment of a monoclonal antibody, a chimeric antibody, a humanized antibody, a multispecific, dual-variable domain immunoglobulins (DVD-Ig®) or multivalent structure formed from an antibody fragment, or a bifunctional antibody.

In one embodiment, optionally, the recombinant antibody is an antibody that:

(a) that specifically binds to a diagnostically relevant region of a *T. cruzi* polypeptide, wherein the *T. cruzi* polypeptide is FRA and further wherein said antibody has at last one binding constant selected from the group consisting of: an association rate constant ($k_a$) between about $7.0 \times 10^5$ $M^{-1}s^{-1}$ to about $7.0 \times 10^6$ $M^{-1}s^{-1}$, an dissociation rate constant ($k_d$) between about $4.0 \times 10^{-3}$ $s^{-1}$ to about $3.0 \times 10^{-1}$ $s^{-1}$ and an equilibrium dissociation constant ($K_D$) between about $5.7 \times 10^{-10}$ M to about $4.3 \times 10^{-7}$ M;

(b) that specifically binds to a diagnostically relevant region of a *T. cruzi* polypeptide, wherein the *T. cruzi* polypeptide is Pep2 and further wherein said antibody has at least one binding constant selected from the group consisting of: an association rate constant ($k_a$) between about $1.0 \times 10^6$ $M^{-1}s^{-1}$ to about $8.0 \times 10^6$ $M^{-1}s^{-1}$; an dissociation rate constant ($k_d$) between about $6.0 \times 10^{-3}$ $s^{-1}$ to about $4.0 \times 10^{-2}$ $s^{-1}$ and an equilibrium dissociation constant ($K_D$) between about $7.5 \times 10^{-10}$ M to about $4.0 \times 10^{-8}$ M;

(c) that specifically binds to a diagnostically relevant region of a *T. cruzi* polypeptide, wherein the *T. cruzi* polypeptide is FP10 and further wherein said antibody has at least one binding constant selected from the group consisting of: (a) an association rate constant ($k_a$) between about $5.0 \times 10^4$ $M^{-1}s^{-1}$ to about $3.0 \times 10^5$ $M^{-1}s^{-1}$; (b) an dissociation rate constant ($k_d$) between about $1.0 \times 10^{-4}$ $s^{-1}$ to about $8.0 \times 10^{-4}$ $s^{-1}$; and (c) an equilibrium dissociation constant ($K_D$) between about $3.3 \times 10^{-10}$ M to about $1.6 \times 10^{-8}$ M;

(d) that specifically binds to a diagnostically relevant region of a *T. cruzi* polypeptide, wherein the *T. cruzi* polypeptide is FP3 and further wherein said antibody has at least one binding constant selected from the group consisting of: an association rate constant ($k_a$) between about $2.0 \times 10^5$ $M^{-1}s^{-1}$ to about $6.0 \times 10^6$ $M^{-1}s^{-1}$; an dissociation rate constant ($k_d$) between about $2.0 \times 10^{-5}$ $s^{-1}$ to about $8.0 \times 10^{-4}$ $s^{-1}$; and an equilibrium dissociation constant ($K_D$) between about $3.3 \times 10^{-12}$ M to about $4.0 \times 10^{-9}$ M; and (e) any combinations of (a)-(d). In another embodiment, optionally, the recombinant antibody is a chimeric antibody that retains the mouse monoclonal antibody specificity and affinity and reacts in an immunoassay format that measures human immunoglobulin. Optionally, the mouse-human chimeric antibody is directed against the FP3, FP6, FP10 or FRA antigen. Optionally, such a chimeric antibody reacts in an existing immunoassay format including, but not limited to, Abbott Laboratories' AxSYM®, ARCHITECT® and PRISM® platforms.

The antigen-binding region comprised by the recombinant antibody can include the entire $V_H$ and/or $V_L$ sequence from the native antibody, or it can comprise one or more portions thereof, such as the CDRs, together with sequences derived from one or more other antibodies. In one embodiment, the recombinant antibody comprises the full-length $V_H$ and $V_L$ sequences of the native antibody.

The native antibody from which the antigen-binding regions are derived is generally a vertebrate antibody. For example, the native antibody can be a rodent (e.g., mouse, hamster, rat) antibody, a chicken antibody, a rabbit antibody, a canine antibody, a feline antibody, a bovine antibody, an equine antibody, a porcine antibody, an ape (e.g., chimpanzee) antibody, or a human antibody. The source of the antibody is based primarily on convenience. In one embodiment, the native antibody is a non-human antibody.

The recombinant antibody also can include one or more constant regions, for example, the $C_L$, $C_H1$ hinge, $C_H2$, $C_H3$, and/or $C_H4$ regions, derived from the same native antibody or from a different antibody. The constant region(s) can be derived from an antibody from one of a number of vertebrate species, including but not limited to, those listed above. In one embodiment, of the present disclosure, the recombinant antibody comprises at least one constant region. In another embodiment, the recombinant antibody comprises one or more constant regions that are derived from a human antibody. In a specific embodiment of the present disclosure, the recombinant antibody comprises the variable region of a non-human antibody linked to the constant region of a human antibody.

The constant region(s) comprised the recombinant antibody can be derived from one or more immunoglobulin classes or isotypes, for example for constant regions derived from human immunoglobulins, the constant region can be derived from one or more of an IgM, IgD, IgG1, IgG2, IgG3, IgG4, IgA1, IgA2 or IgE constant region. When the constant region comprises a region derived from an IgG light chain, this can be derived from a kappa chain or a lambda chain. The recombinant antibody can comprise sequences from more than one class or isotype. Selection of particular constant domains to optimize the desired function of the recombinant antibody is within the ordinary skill in the art. In one embodiment, of the present disclosure, the recombinant antibody comprises one or more constant domains derived from an IgG. In another embodiment, the recombinant antibody comprises regions from both the heavy and light chains of an IgG constant domain.

In one embodiment, of the present disclosure, the antigen-binding regions are derived from a native antibody that specifically binds to an epitope within a diagnostically relevant region of a *T. cruzi* antigenic protein.

In a specific embodiment of the present disclosure, the antigen-binding regions of the recombinant antibody comprise an amino acid sequence substantially identical to all or a portion of the $V_H$ or $V_L$ sequence as set forth in any one of SEQ ID NOs.:10, 12, 14, 16, 18, 20, 26 or 28 (See, Table 12 below; See, Table 11 below for a summary of SEQ ID NO identifiers and the corresponding sequence descriptions). In another embodiment, the antigen-binding regions of the recombinant antibody comprise the complementarity determining regions (CDRs; i.e., CDR1, CDR2 and CDR3) of a $V_H$ or $V_L$ sequence.

TABLE 11

Summary of SEQ ID NOs.: for $V_L$ and $V_H$ chains

| Antigen | Cell line | $V_L$ Polynucleotide | $V_L$ Polypeptide | $V_H$ Polynucleotide | $V_H$ Polypeptide |
|---|---|---|---|---|---|
| FP3 | HBFP3 | 9 | 10 | 11 | 12 |
| FP6 (TcF/Pep2) | HBPep2 | 13 | 14 | 15 | 16 |
| FP10 | HBFP10 | 17 | 18 | 19 | 20 |
| FRA | 8-367-171 | 25 | 26 | 27 | 28 |

TABLE 12

Exemplary V_H and V_L Polypeptide Sequences

| SEQ ID NO.: | Sequence | V_H or V_L | TCA |
|---|---|---|---|
| 10 | YIVMSQSPSS LAVSAGEKVT MSCKSSQSLL NSRTRKNHLA WYQQKPGQSP KLLIYWASTR ESGVPDRFTG SGSGTDFALT ISSVQAEDLA VYFCKQSYNL YTFGAGTKLE LK | V_L | FP3 |
| 12 | DVQLVESGGG LVQPGGSRKL SCAASGFTFS VFGMHWVRQA PEKGLEWVAY ISSGSTIIYY ADTVKGRFTI SRDNPKNTLF LQMTGLRSED TAMYYCARPL YYDYDDYAMD YWGQGTSVTV SS | V_H | FP3 |
| 14 | DIVMSQSPSS LAVSAGEQVT MSCKSSQSLF NSRTRKNYLA WYQQKPGQSP KLLIYWASTR ESGVPDRFTG SGSGTDFTLT ISSVQAEDLA VYYCKQSYNL LTFGAGTKLE LK | V_L | FP6 |
| 16 | QVQLQQPGAE LVRPGASVKL SCKASGYTFT SYWMNWVKLR PGQGLEWIGM IDPSDSETYY DQVFKDKATL TVDKSSSTAY MHLSSLTSED SAVYYCARWI TTDSYTMDYW GQGTSVTVSS | V_H | FP6 |
| 18 | DVVMTQTPLS LPVSLGDQAS ISCRSSQSLV HSNGNTYLHW YLQKPGQSPK LLIYKVSNRF SGVPDRFSGS GSGTDFTLKI SRVEAEDLGV YFCSQSTHVP PTFGGGTKLE IK | V_L | FP10 |
| 20 | QVQLQQPGAE LVKPGASVKM SCKASGYTFT SYWVHWVKQR PGQGLEWIGV IDPSDSYTSY NQKFKGKATL TVDTSSSTAY MQLSSLTSED SAVYYCTRHY DFDSWYFDVW GAGTTVTVSS | V_H | FP10 |
| 26 | DIQMDQSPSS LSASLGDTIT ITCHASQNIN VWLSWYQQKP GNIPKLLIYK ASNLHTGVPS RFSGSGSGTG FTLTISSLQP EDIATYYCQQ GQSYPLTFGS GRKLEIK | V_L | FRA |
| 28 | EVQLQQSGAE LVKPGASVKL SCTASGFNIK DTYMHWVKQR PEQGLEWIGR IDPANGNTKY DPKFQGKATI TTDTSSNTAY LQLSSLTSED TAVYYCATSY YGNYVAYWGH GTLVTVSA | V_H | FRA |

In one embodiment, of the present disclosure, the antigen-binding regions of the recombinant antibody comprise an amino acid sequence substantially identical to all or a portion of the amino acid sequence encoded by any one of SEQ ID NOs.:9, 11, 13, 15, 17, 19, 25 or 27 (See, Table 13, below). In another embodiment, the antigen-binding regions of the recombinant antibody comprise a nucleic acid sequence encoding the complementarity determining regions (CDRs; i.e., CDR1, CDR2 and CDR3) of a V_H or V_L sequence. In a specific embodiment, the antigen-binding regions of the recombinant antibody comprise CDRs having an amino acid sequence substantially identical to the amino acid sequences encoded by one or more of SEQ ID NOs.:9 and 11; one or more of SEQ ID NOs.:13 and 15; or one or more of SEQ ID NOs.:17 and 19; or one or more of SEQ ID NOs.:25 or 27 (See, Table 13, below).

In another specific embodiment of the present disclosure, the antigen-binding regions of the recombinant antibody comprise an amino acid sequence encoded by a nucleic acid sequence substantially identical to all or a portion of the sequence as set forth in any one of SEQ ID NOs.:9, 11, 13, 15, 17, 19, 25 or 27.

TABLE 13

Exemplary Nucleic Acid Sequences Encoding V_H and V_L Sequences

| SEQ ID NO.: | Sequence | V_H or V_L | TCA |
|---|---|---|---|
| 9 | TACATTGTGA TGTCACAGTC TCCATCCTCC CTGGCTGTGT CAGCAGGAGA GAAGGTCACT ATGAGCTGCA AATCCAGTCA GAGTCTGCTC AACAGTAGAA CCCGAAAGAA CCACTTGGCT TGGTATCAGC AGAAACCAGG GCAGTCTCCT AAACTGCTGA TCTACTGGGC ATCCACTAGG GAATCTGGGG TCCCTGATCG CTTCACAGGC AGTGGATCTG GGACAGATTT CGCTCTCACC ATCAGCAGTG TGCAGGCTGA AGACCTGGCA GTTTATTTCT GCAAGCAATC TTATAATCTG TACACATTCG GTGCTGGGAC CAAGCTGGAG CTGAAA | V_L | FP3 |
| 11 | GATGTGCAGC TGGTGGAGTC TGGGGGAGGC TTAGTGCAGC CTGGAGGGTC CCGGAAACTC TCCTGTGCAG CCTCTGGATT CACTTTCAGT GTCTTTGGAA TGCACTGGGT TCGTCAGGCT CCAGAGAAGG GGCTGGAGTG GGTCGCATAC ATTAGTAGTG GCAGTACTAT CATCTATTAT GCAGACACAG TGAAGGGCCG ATTCACCATC TCCAGAGACA ATCCCAAGAA CACCCTGTTC CTGCAAATGA CCGGTCTAAG GTCTGAGGAC ACGGCCATGT | V_H | FP3 |

TABLE 13-continued

Exemplary Nucleic Acid Sequences Encoding V_H and V_L Sequences

| SEQ ID NO.: | Sequence | $V_H$ or $V_L$ | TCA |
|---|---|---|---|
|  | ATTACTGTGC AAGACCGCTC TACTATGATT ACGACGACTA TGCTATGGAC TACTGGGGTC AAGGAACCTC AGTCACCGTC TCCTCA | | |
| 13 | GACATTGTGA TGTCACAGTC TCCATCCTCC CTGGCTGTGT CAGCAGGAGA GCAGGTCACT ATGAGCTGCA AATCCAGTCA GAGTCTGTTC AACAGTAGAA CCCGAAAGAA CTACTTGGCT TGGTACCAGC AGAAACCAGG GCAGTCTCCT AAACTGCTGA TCTACTGGGC ATCCACTAGG GAATCTGGGG TCCCTGATCG CTTCACAGGC AGTGGATCTG GGACAGATTT CACTCTCACC ATCAGCAGTG TGCAGGCTGA AGACCTGGCA GTTTATTACT GCAAACAATC TTATAATCTG CTCACGTTCG GTGCTGGGAC CAAGCTGGAG CTGAAA | $V_L$ | FP6 |
| 15 | CAGGTCCAAC TGCAGCAGCC TGGGGCTGAA CTGGTGAGGC CTGGGGCTTC AGTGAAACTG TCCTGCAAGG CTTCTGGCTA CACCTTCACC AGCTACTGGA TGAACTGGGT GAAGTTGAGG CCTGGACAAG GCCTTGAATG GATTGGTATG ATTGATCCTT CAGACAGTGA AACTTACTAC GATCAAGTAT TCAAGGACAA GGCCACATTG ACTGTTGACA AATCCTCCAG CACAGCCTAC ATGCATCTCA GCAGCCTGAC ATCTGAGGAC TCTGCGGTCT ATTACTGTGC AAGATGGATT ACGACTGATT CCTATACTAT GGACTACTGG GGTCAAGGAA CCTCAGTCAC CGTCTCCTCA | $V_H$ | FP6 |
| 17 | GATGTTGTGA TGACCCAAAC TCCACTCTCC CTGCCTGTCA GTCTTGGAGA TCAAGCCTCC ATCTCTTGCA GATCTAGTCA GAGCCTTGTA CACAGTAATG GAAACCCTAT TTACATTGGT ACCTGCAGAA GCCAGGCCAG TCTCCAAAGC TCCTGATCTA CAAAGTTTCC AACCGATTTT CTGGGGTCCC AGACAGGTTC AGTGGCAGTG GATCAGGGAC AGATTTCACA CTCAAGATCA GCAGAGTGGA GGCTGAGGAT CTGGGAGTTT ATTTCTGCTC TCAAAGTACA CATGTTCCTC CGACGTTCGG TGGAGGCACC AAGCTGGAAA TCAAA | $V_L$ | FP10 |
| 19 | CAGGTCCAAC TGCAGCAGCC TGGGGCTGAG CTGGTGAAGC CTGGGGCTTC AGTGAAGATG TCCTGCAAGG CTTCTGGCTA CACCTTCACC AGCTACTGGG TGCACTGGGT GAAGCAGAGG CCTGGACAAG GCCTTGAGTG GATCGGAGTG ATTGATCCTT CTGATAGTTA TACTAGCTAC AATCAAAAGT TCAAGGGCAA GGCCACATTA CTGTAGACAC ATCCTCCAGC ACAGCCTACA TGCAGCTCAG CAGCCTGACA TCTGAGGACT CTGCGGTCTA TTACTGTACA AGACACTATG ATTTCGACAG CTGGTACTTC GATGTCTGGG GCGCAGGGAC CACGGTCACC GTCTCCTCA | $V_H$ | FP10 |
| 25 | gacatccaga tggaccagtc tccatccagt ctgtctgcat cccttggaga cacaattacc atcacttgcc atgccagtca gaacattaat gtttggttaa gctggtacca gcagaaacca ggaaatattc ctaaactatt gatctataag gcttccaact tgcacacagg cgtcccatca aggtttagtg gcagtggatc tggaacaggt ttcacattaa ccatcagcag cctgcagcct gaagacattg ccacttacta ctgtcaacag ggtcaaagtt atcctctcac gttcggctcg gggcgaaagt tggaaataaa a | $V_L$ | FRA |
| 27 | gaggttcagc tgcagcagtc tggggcagag cttgtgaagc caggggcctc agtcaagttg tcctgcacag cttctggctt caacattaaa gacacctata tgcactgggt gaagcagagg cctgaacagg gcctggagtg gattggaagg attgatcctg cgaatggtaa tactaaatat gacccgaagt tccagggcaa ggccactata acaacagaca catcctccaa cacagcctac ctgcagctca gcagcctgac atctgaggac actgccgtct attactgtgc tacctcctac tatggtaact acgttgctta ctggggccac gggactctgg tcactgtctc tgca | $V_H$ | FRA |

The amino acid sequence of recombinant antibody need not correspond precisely to the parental sequences, i.e., it can be a "variant sequence." For example, depending in the domains comprised by the recombinant antibody, one or more of the $V_L$, $V_H$, $C_L$, $C_H1$, hinge, $C_H2$, $C_H3$, and $C_H4$, as applicable, can be mutagenized by substitution, insertion or deletion of one or more amino acid residues so that the residue at that site does not correspond to either the parental (or reference) sequence. One skilled in the art will appreciate, however, that such mutations will not be extensive and will not significantly affect binding of the recombinant antibody to its target TCA. In accordance with the present disclosure, when a recombinant antibody comprises a variant sequence, the variant sequence is at least about 70% (e.g., from about 70% to about 100%) identical to the reference sequence. In one embodiment, the variant sequence is at least about 75% (e.g., from about 75% to about 100%) identical to the reference sequence. In other embodiments, the variant sequence is at least about 80% (e.g., from about 80% to about 100%), at least about 85% (e.g., from about 85% to about 100%), or at least about 90% (e.g., from about 90% to about 100%) identical to the reference sequence. In a specific embodiment, the reference sequence corresponds to a sequence as set forth in any one of SEQ ID NOs.:10, 12, 14, 16, 18, 20, 26 or 28.

Generally, when the recombinant antibody comprises a variant sequence that contains one or more amino acid substitutions, they are "conservative" substitutions. A conservative substitution involves the replacement of one amino acid residue by another residue having similar side chain properties. As is known in the art, the twenty naturally occurring amino acids can be grouped according to the physicochemical properties of their side chains. Suitable groupings include alanine, valine, leucine, isoleucine, proline, methionine, phenylalanine and tryptophan (hydrophobic side chains); glycine, serine, threonine, cysteine, tyrosine, asparagine, and glutamine (polar, uncharged side chains); aspartic acid and glutamic acid (acidic side chains) and lysine, arginine and histidine (basic side chains). Another grouping of amino acids is phenylalanine, tryptophan, and tyrosine (aromatic side chains). A conservative substitution involves the substitution of an amino acid with another amino acid from the same group.

Thus, the present disclosure in other embodiments further provides isolated polypeptides corresponding to novel recombinant antibody sequences disclosed herein. Optionally the isolated polypeptide comprises a portion of a recombinant (e.g., chimeric) antibody that specifically binds to a diagnostically relevant region of a TCA selected from the group consisting of FP3, FP6, and FP10. In one embodiment, the polypeptide comprises a $V_H$ region selected from the group consisting of a $V_H$ region comprising an amino acid sequence substantially identical to the sequence as set forth in any one or more of SEQ ID NOs.:12, 16, 20 or 28. In still another embodiment, the polypeptide comprises a $V_H$ region comprising complementarity determining region sequences. In another embodiment, the polypeptide comprises a $V_L$ region comprising an amino acid sequence that is substantially identical to the sequence as set forth in any one or more of SEQ ID NOS.:10, 14, 18 or 26. In still another embodiment, the polypeptide comprises a $V_L$ region comprising complementarity determining region sequences.

In still another embodiment, the polypeptide comprises a $V_H$ region selected from the group consisting of a $V_H$ region comprising an amino acid sequence substantially identical to the sequence encoded by any one or more of SEQ ID NOs.: 11, 15, 19 or 27. In another embodiment, the polypeptide comprises a $V_L$ region selected from the group consisting of a $V_L$ region comprising an amino acid sequence substantially identical to the sequence encoded by any one or more of SEQ ID NOs.:9, 13, 17 or 25.

Likewise, the nucleic acid sequence encoding the variable region(s) need not correspond precisely to the parental reference sequence but can vary by virtue of the degeneracy of the genetic code and/or such that it encodes a variant amino acid sequence as described above. In one embodiment, of the present disclosure, therefore, the nucleic acid sequence encoding a variable region of the recombinant antibody is at least about 70% (e.g., from about 70% to about 100%) identical to the reference sequence. In another embodiment, the nucleic acid sequence encoding a variable region of the recombinant antibody is at least about 75% (e.g., from about 75% to about 100%) identical to the reference sequence. In other embodiments, the nucleic acid sequence encoding a variable region of the recombinant antibody is at least about 80% (e.g., from about 80% to about 100%), at least about 85% (e.g., from about 85% to about 100%), or at least about 90% (e.g., from about 90% to about 100%) identical to the reference sequence. In a specific embodiment, the reference sequence corresponds to a sequence as set forth in any one of SEQ ID NOs.:9, 11, 13, 15, 17, 19 25 or 27.

Thus, the present disclosure in other embodiments further provides isolated polynucleotides which encode novel recombinant antibody sequences, including chimerical antibody sequences, disclosed herein. Optionally, the isolated polynucleotide encodes a portion of a recombinant (e.g., chimeric) antibody that specifically binds to a diagnostically relevant region of a *T. cruzi* protein selected from the group consisting of FP3, FP6 and FP10 protein. In one embodiment, the polynucleotide encodes a $V_H$ region selected from the group consisting of a $V_H$ region comprising an amino acid sequence substantially identical to the sequence as set forth in any one or more of SEQ ID NOs.:12, 16, 20 or 28. In another embodiment the polynucleotide encodes a $V_L$ region comprising an amino acid sequence that is substantially identical to the sequence as set forth in any one or more of SEQ ID NOs.:10, 14, 18 or 26. In still another embodiment, the polynucleotide encodes a $V_L$ region comprising complementarity determining region sequences.

In still another embodiment, the polynucleotide encodes a $V_H$ region selected from the group consisting of a $V_H$ region comprising an amino acid sequence substantially identical to the sequence encoded by any one or more of SEQ ID NOs.:9, 13, 17 or 27. In yet another embodiment, the polynucleotide encodes a $V_H$ region comprising complementarity determining region sequences. In another embodiment, the polynucleotide encodes a $V_L$ region selected from the group consisting of a $V_L$ region comprising an amino acid sequence substantially identical to the sequence encoded by any one or more of SEQ ID NOs.:11, 15, 19 or 25. In still yet another embodiment, the polynucleotide encodes a $V_L$ region comprising complementarity determining region sequences.

In one embodiment, the antibodies can be further modified to reduce the immunogenicity to a human relative to the native antibody by mutating one or more amino acids in the non-human portion of the antibody that are potential epitopes for human T-cells in order to eliminate or reduce the immunogenicity of the antibody when exposed to the human immune system. Suitable mutations include, for example, substitutions, deletions and insertions of one or more amino acids.

In one embodiment, the recombinant antibodies of the present disclosure can be further modified for immobilization onto a suitable solid phase. Immobilization can be achieved through covalent or non-covalent (for example, ionic, hydrophobic, or the like) attachment to the solid phase. Suitable modifications are known in the art and include the addition of a functional group or chemical moiety to either the C-terminus or the N-terminus of one of the amino acid sequences comprised by the recombinant antibody to facilitate cross-linking or attachment of the recombinant antibody to the solid support. Exemplary modifications include the addition of functional groups such as S-acetylmercaptosuccinic anhydride (SAMSA) or S-acetyl thioacetate (SATA), or addition of one or more cysteine residues to the N- or C-terminus of the amino acid sequence. Other cross-linking reagents are known in the art, and many are commercially available (see, for example, catalogues from Pierce Chemical Co. (Rockford, Ill., USA) and Sigma-Aldrich; Saint Louis, Mo., USA). Examples include, but are not limited to, diamines, such as 1,6-diaminohexane; dialdehydes, such as glutaraldehyde;

bis-N-hydroxysuccinimide esters, such as ethylene glycol-bis(succinic acid N-hydroxysuccinimide ester), disuccinimidyl glutarate, disuccinimidyl suberate, and ethylene glycol-bis(succinimidylsuccinate); diisocyanates, such as hexamethylenediisocyanate; bis oxiranes, such as 1,4 butanediyl diglycidyl ether; dicarboxylic acids, such as succinyldisalicylate; 3-maleimidopropionic acid N-hydroxysuccinimide ester, and the like.

Other modifications include the addition of one or more amino acids at the N- or C-terminus, such as histidine residues to allow binding to $Ni^{2+}$ derivatized surfaces, or cysteine residues to allow disulfide bridge formation or binding to SULFOLINK™ agarose. Alternatively, the antibody can be modified to include one or more chemical spacers at the N-terminus or C-terminus in order to distance the recombinant antibody optimally from the solid support. Spacers that can be used include, but are not limited to, 6-aminohexanoic acid; 1,3-diamino propane; 1,3-diamino ethane; and short amino acid sequences, such as polyglycine sequences, of 1 to 5 amino acids.

In an alternative embodiment, the recombinant antibodies optionally can be conjugated to a carrier protein, such as bovine serum albumin (BSA), casein, or thyroglobulin, in order to immobilize them onto a solid phase.

In another embodiment, the present disclosure provides for modification of the recombinant antibodies to incorporate a detectable label. Detectable labels according to the disclosure preferably are molecules or moieties which can be detected directly or indirectly and are chosen such that conjugation of the detectable label to the recombinant antibody preferably does not interfere with the specific binding of the antibody to its target *T. cruzi* protein. Methods of labeling antibodies are well-known in the art and include, for example, the use of bifunctional cross-linkers, such as SAMSA (S-acetylmercaptosuccinic anhydride), to link the recombinant antibody to the detectable label. Other cross-linking reagents such as are known in the art or which similar to those described above likewise can be used.

Detectable labels for use with the recombinant antibodies of the present disclosure include, for example, those that can be directly detected, such as radioisotopes, fluorophores, chemiluminophores, enzymes, colloidal particles, fluorescent microparticles, and the like. The detectable label is either itself detectable or can be reacted with one or more additional compounds to generate a detectable product. Thus, one skilled in the art will understand that directly detectable labels of the disclosure can require additional components, such as substrates, triggering reagents, light and the like to enable detection of the label. Examples of detectable labels include, but are not limited to, chromogens, radioisotopes (such as, e.g., $^{125}I$, $^{131}I$, $^{32}P$, $^{3}H$, $^{35}S$ and $^{14}C$), fluorescent compounds (such as fluorescein, rhodamine, ruthenium tris bipyridyl and lanthanide chelate derivatives), chemiluminescent compounds (such as, e.g., acridinium and luminol), visible or fluorescent particles, nucleic acids, complexing agents, or catalysts such as enzymes (such as, e.g., alkaline phosphatase, acid phosphatase, horseradish peroxidase, β-galactosidase, β-lactamase, luciferase). In the case of enzyme use, addition of, for example, a chromo-, fluoro-, or lumogenic substrate preferably results in generation of a detectable signal. Other detection systems such as time-resolved fluorescence, internal-reflection fluorescence, and Raman spectroscopy are optionally also useful.

The present disclosure also provides for the use of labels that are detected indirectly. Indirectly detectable labels typically involve the use of an "affinity pair," i.e., two different molecules, where a first member of the pair is coupled to the recombinant antibody of the present disclosure, and the second member of the pair specifically binds to the first member. Binding between the two members of the pair is typically chemical or physical in nature. Examples of such binding pairs include, but are not limited to: antigens and antibodies; avidin/streptavidin and biotin; haptens and antibodies specific for haptens; complementary nucleotide sequences; enzyme cofactors/substrates and enzymes; and the like.

F. PREPARATION OF ANTIBODIES

Polyclonal Abs can be raised in a mammalian host by one or more injections of an immunogen and, if desired, an adjuvant. Typically, the immunogen (and adjuvant) is injected in the mammal by multiple subcutaneous or intraperitoneal injections. The immunogen can include a TCA or a TCA-fusion polypeptide. Examples of adjuvants include Freund's complete and monophosphoryl Lipid A synthetic-trehalose dicorynomycolate (MPL-TDM). To improve the immune response, an immunogen can be conjugated to a polypeptide that is immunogenic in the host, such as keyhole limpet hemocyanin (KLH), serum albumin, bovine thyroglobulin, and soybean trypsin inhibitor. Protocols for antibody production are well-known (Ausubel et al., 1987; Harlow, E., and D. Lane. 1988. Antibodies: A laboratory manual. Cold Spring Harbor Laboratory Press, Cold Spring Harbor. 726 pp; Harlow, E., and D. Lane. 1999. Using antibodies: A laboratory manual. Cold Spring Harbor Laboratory PRess, Cold Spring Harbor, N.Y.). Alternatively, pAbs can be made in chickens, producing IgY molecules (Schade, R., et al. 1996. The production of avian (egg yolk) antibodies: IgY. The report and recommendations of ECVAM workshop. *Alternatives to Laboratory Animals (ATLA)*. 24:925-934).

Methods of raising monoclonal antibodies against a desired antigen are well known in the art. For example, monoclonal antibodies can be made using the hybridoma method first described by Kohler et al., *Nature*, 256:495 (1975). In general in the hybridoma method, a mouse or other appropriate host animal, such as a hamster or macaque monkey, is immunized by multiple subcutaneous or intraperitoneal injections of antigen and a carrier and/or adjuvant at multiple sites. Two weeks later, the animals are boosted, and about 7 to 14 days later animals are bled and the serum is assayed for anti-antigen titer. Animals can be boosted until titer plateaus.

The splenocytes of the mice are extracted and fused with myeloma cells using a suitable fusing agent, such as polyethylene glycol, to form a hybridoma cell (see, for example, Goding, *Monoclonal Antibodies: Principles and Practice*, pp. 59-103 (Academic Press, 1986); Galfre et al., *Nature*, 266:550 (1977)). Suitable myeloma cell lines are known in the art and include, but are not limited to, murine myeloma lines, such as those derived from MOP-21 and MC-11 mouse tumors (available from the Salk Institute Cell Distribution Center, San Diego, Calif., USA), as well as SP-2, SP2/0 and X63-Ag8-653 cells (available from the American Type Culture Collection (ATCC), Manassas, Va., USA). Human myeloma and mouse-human heteromyeloma cell lines also have been described for the production of human monoclonal antibodies (see, for example, Kozbor, J. *Immunol.*, 133:3001 (1984); Brodeur et al., *Monoclonal Antibody Production Techniques and Applications*, pp. 51-63 (Marcel Dekker, Inc., New York, 1987)). The hybridoma cells thus prepared can be seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

The hybridoma cells obtained through such a selection are then assayed to identify clones which secrete antibodies capable of binding the *T. cruzi* antigen used in the initial immunization, for example, by immunoprecipitation or by an in vitro binding assay, such as radioimmunoassay (RIA) or enzyme-immunoassay (EIA or ELISA). The binding affinity of the monoclonal antibody can optionally be determined, for example, by the Scatchard analysis of Munson et al., *Anal. Biochem.*, 107:220 (1980).

After hybridoma cells are identified that produce antibodies of the desired specificity, the clones can be subcloned by limiting dilution procedures, for example the procedure described by Wands et al. (*Gastroenterology* 80:225-232 (1981)), and grown by standard methods (see, for example, Goding, ibid.). Suitable culture media for this purpose include, for example, D-MEM, IMDM or RPMI-1640 medium. Alternatively, the hybridoma cells can be grown in vivo as ascites tumors in an animal.

The monoclonal antibodies secreted by the subclones optionally can be isolated from the culture medium, ascites fluid, or serum by conventional immunoglobulin purification procedures such as, for example, protein A chromatography, hydroxylapatite chromatography, gel electrophoresis, dialysis, or affinity chromatography.

Examples 1-4 (See, the Example section) illustrate just one approach to obtaining mAbs to the TCAs found in FP3, FP6, FP10 and FRA polypeptides (e.g., the polypeptides represented by the amino acid sequences of SEQ ID NOs.:2, 4, 6 and 8).

G. PREPARATION OF RECOMBINANT ANTIBODIES

The recombinant antibodies of the present disclosure can comprise antigen-binding domain sequences (for example, the $V_H$ and/or $V_L$ sequences, or a portion thereof) derived from, for example, a monoclonal antibody produced by a human or non-human animal, such as a rodent, rabbit, canine, feline, bovine, equine, porcine, ape or chicken. Alternatively, antigen-binding domains with the desired binding activity can be selected through the use of combinatorial libraries expressed in lambda phage, on the surface of bacteriophage, bacteria or yeast, or screened by display on other biological (for example, retrovirus or polysome) or non-biological systems using standard techniques (See, for example, Marks, J. D. et. al., *J. Mol. Biol.* 222:581-597 (1991); Barbas, C. F. III et. al., *Proc. Natl. Acad. Sci. USA* 89:4457-4461 (1992)). The libraries can be composed of native antigen-binding domains isolated from an immunized or unimmunized host, synthetic or semi-synthetic antigen-binding domains, or modified antigen-binding domains.

1. Recombinant Abs Generally

In one embodiment of the present disclosure, the recombinant antibodies comprise antigen-binding domains derived from monoclonal antibodies that bind to the *T. cruzi* protein of interest.

In one embodiment of the present disclosure, the recombinant antibodies are derived from monoclonal antibodies raised to a *T. cruzi* antigen derived from a diagnostically relevant region of a *T. cruzi* protein. In another embodiment, the recombinant antibodies are derived from monoclonal antibodies raised to a *T. cruzi* antigen, such as FP3, FP6, or FP10. In another embodiment, the recombinant antibodies are derived from monoclonal antibodies raised to a *T. cruzi* antigen comprising all or a fragment (for example, a fragment comprising one or more epitopes) of FP3, FP6 or FP10. In a further embodiment, the recombinant antibodies are derived from monoclonal antibodies raised to a *T. cruzi* antigen comprising a sequence substantially identical to the sequence as set forth in any one of SEQ ID NOs.:2, 4 or 6.

Optionally, the monoclonal antibody is expressed by a cell line selected from the group consisting of HBFP3, HBPep2, and HBFP10. In an alternative embodiment, the cell line is Chagas 8-367-171.

Once a monoclonal antibody has been prepared, DNA encoding the monoclonal antibody or the variable regions thereof can readily be isolated by standard techniques, for example by using oligonucleotide probes that are capable of binding specifically to genes encoding the heavy and light chains or the variable regions of the monoclonal antibody, or by RT-PCR of the mRNA encoding the monoclonal antibody using primers to conserved regions (for example, the IgG primer sets available from Novagen (EMD Biosciences, Inc.), San Diego, Calif., USA).

Once isolated, the DNA can be, for example, cloned into an appropriate expression vector and introduced into a suitable host cell, such as *E. coli* cells, yeast cells, simian COS cells, Chinese hamster ovary (CHO) cells, human embryonic kidney (HEK) cells (for example, HEK 293), or myeloma cells that do not otherwise produce immunoglobulin protein, in order to produce recombinant monoclonal antibodies. Optionally, in one embodiment, the anti-*T. cruzi* mouse-human chimeric antibodies of the disclosure are produced in a Chinese Hamster Ovary (CHO) cell line, which is advantageous in that they can be produced in quantities sufficient for commercial use. Preferably, the mammalian host cells are CHO cell lines and HEK 293 cell lines. Another preferred host cell is the B3.2 cell line (e.g., Abbott Laboratories, Abbott Bioresearch Center, Worcester, Mass.), or another dihydrofolate reductase deficient (DHFR-) CHO cell line (e.g., available from Invitrogen Corp., Carlsbad, Calif.).

Alternatively, the DNA encoding the monoclonal antibody or the variable regions thereof can be used to produce chimeric antibodies, humanized antibodies and antibody fragments by standard methods known in the art.

For example, chimeric monoclonal antibodies can be produced by cloning the DNA encoding the variable regions of the monoclonal antibody into mammalian expression vector(s) containing antibody heavy and light chain constant region genes derived from a different host species. Many eukaryotic antibody expression vectors that are either stably integrated or exist as extrachromosomal elements have been described and are known to those of ordinary skill in the art. In general, antibody expression vectors are plasmids comprising the gene encoding the heavy chain constant region and/or the gene encoding the light chain constant region, an upstream enhancer element and a suitable promoter.

A wide variety of expression control sequences may be used in the present disclosure. Such useful expression control sequences include the expression control sequences associated with structural genes of the foregoing expression vectors as well as any sequence known to control the expression of genes of prokaryotic or eukaryotic cells or their viruses, and various combinations thereof. Examples of suitable control sequences for directing transcription in mammalian cells include the early and late promoters of SV40 and adenovirus, for example, the adenovirus major late promoter, the MT-1 (metallothionein gene) promoter, the human cytomegalovirus immediate-early gene promoter (CMV), the human elongation factor 1α (EF-1α) promoter, the *Drosophila* minimal heat shock protein 70 promoter, the Rous Sarcoma Virus (RSV) promoter, the human ubiquitin C (UbC) promoter, the human growth hormone terminator, SV40 or adenovirus E1b region polyadenylation signals and the Kozak consensus sequence (Kozak, *J Mol Biol.*, 196:947-50 (1987)).

For example, for human constant regions, the antibody expression vector can comprise the human IgG1 (human Cγ1) and human kappa constant region (human Cκ) genes and the immunoglobulin H chain enhancer element. The vector can also contain a bacterial origin of replication and selection marker. Optional inclusion of a selection marker, as is known in the art, allows for selection and amplification under defined growth conditions, for example the dihydrofolate reductase (DHFR) gene provides for selection and amplification in mammalian cells with methotrexate. Construction of a vector appropriate for antibody expression starting from a commercial mammalian expression vector, can be readily achieved by the skilled technician. As described herein various vectors including pBV, pJV, and pBOS vectors, as well as variety of intermediary vectors and plasmids can be employed for antibody production. pBV, pJV, and pBOS vectors were acquired from Abbott Bioresearch Center (Worcester, Mass.). Other similar plasmids and vectors are commercially available and/or readily constructed.

Introduction of the expression construct(s) into appropriate host cells results in production of complete chimeric antibodies of a defined specificity (see, for example, Morrison, S. L. et al., *Proc. Natl. Acad. Sci. USA* 81: 6851-6855 (1984)). The heavy and light chain coding sequences can be introduced into the host cell individually on separate plasmids or together on the same vector.

Depending on the vector system used, many different immortalized cell lines can serve as suitable hosts, these include, but are not limited to, myeloma (for example, X63-Ag8.653), hybridoma (for example, Sp2/0-Ag14), lymphoma, insect cells (for example sf9 cells), human embryonic kidney cells (for example, HEK 293) and Chinese Hamster Ovary (CHO) cells. The expression constructs can be introduced into the host cells using a variety of techniques known in the art, including but not limited to, calcium phosphate precipitation, protoplast fusion, lipofection, retrovirus-derived shuttle vectors, and electroporation.

Chimeric antibodies and antibody fragments can also be produced in other expression systems including, but not limited to, baculovirus, yeast, bacteria (such as *E. coli*), and in vitro in cell-free systems, such as rabbit reticulocyte lysate.

The recombinant antibody can be isolated from the host cells by standard immunoglobulin purification procedures such as, for example, cross-flow filtration, ammonium sulphate precipitation, protein A chromatography, hydroxylapatite chromatography, gel electrophoresis, dialysis, affinity chromatography, or combinations thereof.

Alternatively, antibody fragments can be generated from a purified antibody preparation by conventional enzymatic methods, for example, F(ab')$_2$ fragments can be produced by pepsin cleavage of the intact antibody, and Fab fragments can be produced by briefly digesting the intact antibody with papain.

Recombinant bispecific and heteroconjugate antibody fragments having specificities for at least two different antigens can be prepared as full length antibodies or as antibody fragments (such as F(ab')$_2$ bispecific antibody fragments). Antibody fragments having more than two valencies (for example, trivalent or higher valency antibody fragments) also are contemplated. Bispecific antibodies, heteroconjugate antibodies, and multi-valent antibodies can be prepared by standard methods known to those skilled in the art.

2. Monovalent Abs

Monovalent Abs do not cross-link each other. One method involves recombinant expression of Ig light chain and modified heavy chain. Heavy chain truncations generally at any point in the Fc region prevents heavy chain cross-linking. Alternatively, the relevant cysteine residues are substituted with another amino acid residue or are deleted, preventing crosslinking by disulfide binding. In vitro methods are also suitable for preparing monovalent Abs. Abs can be digested to produce fragments, such as Fab (Harlow and Lane, 1988, supra; Harlow and Lane, 1999, supra).

3. Humanized and Human Abs

Humanized forms of non-human Abs that bind a TCA are chimeric Igs, Ig chains or fragments (such as Fv, Fab, Fab', F(ab')$_2$ or other antigen-binding subsequences of Abs) that contain minimal sequence derived from non-human Ig.

Generally, a humanized antibody has one or more amino acid residues introduced from a non-human source. These non-human amino acid residues are often referred to as "import" residues that are typically taken from an "import" variable domain. Humanization is accomplished by substituting rodent CDRs or CDR sequences for the corresponding sequences of a human antibody (Jones, P. T., et al. 1986. Replacing the complementarity-determining regions in a human antibody with those from a mouse. *Nature.* 321:522-5; Riechmann, L., et al. 1988. Reshaping human antibodies for therapy. *Nature.* 332:323-7; Verhoeyen, M., et al. 1988. Reshaping human antibodies: grafting an antilysozyme activity. *Science.* 239:1534-6). Such "humanized" Abs are chimeric Abs (Cabilly et al., 1989), wherein substantially less than an intact human variable domain has been substituted by the corresponding sequence from a non-human species. In practice, humanized Abs are typically human Abs in which some CDR residues and possibly some FR residues are substituted by residues from analogous sites in rodent Abs. Humanized Abs include human Igs (recipient antibody) in which residues from a complementary determining region (CDR) of the recipient are replaced by residues from a CDR of a non-human species (donor antibody), such as mouse, rat or rabbit, having the desired specificity, affinity and capacity. In some instances, corresponding non-human residues replace Fv framework residues of the human Ig. Humanized Abs can include residues that are found neither in the recipient antibody nor in the imported CDR or framework sequences. In general, the humanized antibody contains substantially all of at least one, and typically two, variable domains, in which most if not all of the CDR regions correspond to those of a non-human Ig and most if not all of the FR regions are those of a human Ig consensus sequence. The humanized antibody optimally also comprises at least a portion of an Ig constant region (Fc), typically that of a human Ig (Jones et al., 1986; Presta, 1992; Riechmann et al., 1988).

Human Abs can also be produced using various techniques, including phage display libraries (Hoogenboom, H. R., et al. 1991. Multi-subunit proteins on the surface of filamentous phage: methodologies for displaying antibody (Fab) heavy and light chains. *Nucleic Acids Res.* 19:4133-7; Marks, J. D., et al. 1991. By-passing immunization. Human antibodies from V-gene libraries displayed on phage. *J Mol Biol.* 222: 581-97) and human mAbs (Boerner, P., et al. 1991. Production of antigen-specific human monoclonal antibodies from in vitro-primed human splenocytes. *J Immunol.* 147:86-95; Reisfeld, R. A., and S. Sell. 1985. Monoclonal antibodies and cancer therapy: Proceedings of the Roche-UCLA symposium held in Park City, Utah, Jan. 26-Feb. 2, 1985. Alan R. Liss, New York. 609 pp). Introducing human Ig genes into transgenic animals in which the endogenous Ig genes have been partially or completely inactivated can be exploited to synthesize human Abs. Upon challenge, human antibody production is observed, which closely resembles that seen in humans in all respects, including gene rearrangement, assembly, and antibody repertoire (Fishwild, D. M., et al. 1996. High-avidity human IgG kappa monoclonal antibodies from a novel strain of minilocus transgenic mice. *Nat Biotechnol.* 14:845-51; Lonberg and Huszar, 1995; Lonberg et al., 1994; Marks et al., 1992; Lonberg, N., and R. M. Kay. U.S. Pat. No. 5,569,825. 1996; Lonberg, N., and R. M. Kay. U.S. Pat. No. 5,633,425. 1997a; Lonberg, N., and R. M. Kay. U.S. Pat. No. 5,661,016. 1997b; Lonberg, N., and R. M. Kay. U.S. Pat. No. 5,625,126. 1997c; Surani, A., et al. U.S. Pat. No. 5,545,807. 1996).

3. Bi-specific Abs

Bi-specific mAbs bind at least two different antigens. For example, a binding specificity is a TCA; the other is for any antigen of choice.

The recombinant production of bi-specific Abs is often achieved by co-expressing two Ig heavy-chain/light-chain pairs, each having different specificities. The random assortment of these Ig heavy and light chains in the resulting hybridomas (quadromas) produce a potential mixture of ten different antibody molecules, of which only one has the desired bi-specific structure. The desired antibody can be purified using affinity chromatography or other techniques (Traunecker, A., et al. 1991. Myeloma based expression system for production of large mammalian proteins. *Trends Biotechnol.* 9:109-13; Wabl, M., J. Berg, and E. Lotscher. WO 93/08829. 1993).

To manufacture a bi-specific antibody, variable domains with the desired antibody-antigen combining sites are fused to Ig constant domain sequences (Suresh, M. R., A. C. Cuello, and C. Milstein. 1986. Bispecific monoclonal antibodies from hybrid hybridomas. *Methods Enzymol.* 121:210-28). The fusion is usually with an Ig heavy-chain constant domain, comprising at least part of the hinge, CH2, and CH3 regions. The first heavy-chain constant region (CH1) containing the site necessary for light-chain binding is in at least one of the fusions. DNAs encoding the Ig heavy-chain fusions and, if desired, the Ig light chain, are inserted into separate expression vectors and are co-transfected into a suitable host organism.

The interface between a pair of antibody molecules can be engineered to maximize the percentage of heterodimers that are recovered from recombinant cell culture (Carter, P., L. et al. WO 96/27011. 1996). In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine). This mechanism increases the yield of the heterodimer over unwanted end products, such as homodimers.

Bi-specific Abs can be prepared as full length Abs or antibody fragments (e.g., Fab'$_2$ bi-specific Abs). One technique to generate bi-specific Abs exploits chemical linkage. Intact Abs can be proteolytically cleaved to generate Fab'$_2$ fragments (Brennan, M., et al. 1985. Preparation of bispecific antibodies by chemical recombination of monoclonal immunoglobulin G1 fragments. *Science.* 229:81-3). Fragments are reduced with a dithiol complexing agent, such as sodium arsenite, to stabilize vicinal dithiols and prevent intermolecular disulfide formation. The generated Fab' fragments are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bi-specific antibody.

Fab' fragments can be directly recovered from *E. coli* and chemically coupled to form bi-specific Abs. For example, fully humanized bi-specific Fab'$_2$ Abs can be produced (Shalaby, M. R., et al. 1992. Development of humanized bispecific antibodies reactive with cytotoxic lymphocytes and tumor cells overexpressing the HER2 protooncogene. *J Exp Med.* 175:217-25). Each Fab' fragment is separately secreted from *E. coli* and directly coupled chemically in vitro, forming the bi-specific antibody.

Various techniques for making and isolating bi-specific antibody fragments directly from recombinant cell culture have also been described. For example, leucine zipper motifs can be exploited (Kostelny, S. A., et al. 1992. Formation of a bispecific antibody by the use of leucine zippers. *J Immunol.* 148:1547-53). Peptides from the Fos and Jun polypeptides are linked to the Fab' portions of two different Abs by gene fusion. The antibody homodimers are reduced at the hinge region to form monomers and then re-oxidized to form antibody heterodimers. This method can also produce antibody homodimers. "Diabody" technology provides an alternative method to generate bi-specific antibody fragments (Holliger et al., 1993). The fragments consist of a heavy-chain $V_H$ connected to a light-chain $V_L$ by a linker that is too short to allow pairing between the two domains on the same chain. The $V_H$ and $V_L$ domains of one fragment are forced to pair with the complementary $V_L$ and $V_H$ domains of another fragment, forming two antigen-binding sites. Another strategy for making bi-specific antibody fragments is the use of single-chain Fv (sFv) dimers (Gruber, M., et al. 1994. Efficient tumor cell lysis mediated by a bispecific single chain antibody expressed in *Escherichia coli*. *J Immunol.* 152:5368-74). Abs with more than two valencies can also be made, such as tri-specific Abs (Tutt, A., et al. 1991. Trispecific F(ab')3 derivatives that use cooperative signaling via the TCR/CD3 complex and CD2 to activate and redirect resting cytotoxic T cells. *J Immunol.* 147:60-9). Exemplary bi-specific Abs can bind to two different epitopes on a given TCA.

H. TESTING OF RECOMBINANT ANTIBODIES

The ability of the recombinant antibody to specifically bind to the target *T. cruzi* antigen can be assessed by standard immunological techniques (see, for example, *Current Protocols in Immunology*, Coligan, J. E., et al. (ed.), J. Wiley & Sons, New York, N.Y.). For example, by radioimmunoassay (RIA) or enzyme immunoassay (EIA or ELISA). In one embodiment of the present disclosure, the recombinant antibody demonstrates substantially the same specificity as the monoclonal antibody from which the antigen-binding domains are derived.

The recombinant antibodies optionally can also be tested for their binding affinity to the target *T. cruzi* antigen by measuring the equilibrium dissociation constant ($K_D$) by standard techniques. In one embodiment of the present disclosure, the recombinant antibodies (e.g., chimeric antibodies) have a $K_D$ less than about 1 μM. In another embodiment, the recombinant antibodies (e.g., chimeric antibodies) have a $K_D$ less than about 100 nM.

Other standard tests also can be done on the antibodies, for example, the pI value of the antibodies can be obtained.

Optionally, the recombinant antibodies (e.g., chimeric antibodies) are subjected to epitope mapping procedures to identify the region of the target antigen to which they bind. A variety of methods of epitope mapping are known in the art (see, for example, *Current Protocols in Immunology*, Coligan, J. E., et al. (ed.), J. Wiley & Sons, New York, N.Y.) and include, for example, phage and yeast display methods. Phage and yeast display methods can also be combined with random mutagenesis techniques in order to more precisely map the residues of the target antigen involved in antibody binding (see, for example, Chao, G., et al., *J. Mol. Biol.*, 10:539-50 (2004)).

In one embodiment of the present disclosure, the residues of the target antigen to which the recombinant antibodies bind are identified by a technique that combines scanning alanine mutagenesis with yeast display. The technique generally involves the preparation of a series of oligonucleotides encoding peptides each representing the target region of the antigen and in which each individual amino acid in this region was sequentially substituted by alanine. The target region of the antigen is determined either from the antigen used in the initial immunization to prepare the parent monoclonal antibody, or from a preliminary "low-resolution" screening using yeast or phage display. A wildtype version of the antigen is used as a control. Each oligonucleotide is cloned into an appropriate yeast display vector and each alanine mutant transformed into a suitable host, such as *E. coli*. Plasmid DNA is extracted and sequenced and clones are selected based on sequencing. Yeast display vectors are known in the art and are commercially available (for example, pYD1 available from Invitrogen Corp., Carlsbad, Calif., USA).

The selected clones are then transformed into *Saccharomyces cerevesiae* cells, for example, EBY100 cells (Invitrogen Corp.), and individual yeast clones cultured and induced for peptide expression. The induced yeast cells expressing the alanine mutants on the cell surface are incubated with the recombinant antibody and bound antibody is detected by conventional methods, for example using a labeled secondary antibody. Key residues in the target antigenic region can then be determined based on the identification of alanine mutants unable to bind to the recombinant antibody. A loss of antibody binding activity indicates that the mutant includes an alanine residue at a position that forms part of the epitope for the recombinant antibody.

I. USES OF RECOMBINANT ANTIBODIES

The recombinant antibodies of the present disclosure are suitable for use, for example, as diagnostic reagents for the detection of *T. cruzi*, and/or as standardization reagents, positive control reagents or calibrator reagents in assays or kits for the detection of *T. cruzi* antibodies in place of traditional plasma or serum. Standardization reagents can be used, for example, to establish standard curves for interpolation of antibody concentration. Positive controls can be used to establish assay performance characteristics and/or quantitate and monitor the integrity of the antigen(s) used in the assay. The present disclosure also provides for the use of a plurality of the recombinant antibodies, each recombinant antibody capable of specifically binding to a different *T. cruzi* antigen, as standardized antibody sensitivity panels. Such sensitivity panels can be used, for example, in place of traditional plasma or serum for quality control of *T. cruzi* antibody detection kits, to establish assay performance characteristics and/or quantitate and monitor the integrity of the antigen(s) used in the assay. The present disclosure also contemplates the use of the recombinant antibodies in the treatment or prevention of a *T. cruzi* infection.

One embodiment of the present disclosure thus provides for an immunodiagnostic reagent comprising one or more recombinant antibodies, each capable of specifically binding a diagnostically relevant region of a *T. cruzi* protein.

In one embodiment of the present disclosure, the immunodiagnostic reagent comprises a plurality of (for example, two or more) recombinant antibodies each capable of detecting a different *T. cruzi* antigen.

The immunodiagnostic reagent can be tailored for a specific end use by appropriate selection of the recombinant antibodies it comprises, thus making the immunodiagnostic reagent compatible with a number of existing *T. cruzi* detection assay formats and kits. Tailoring the immunodiagnostic reagent in this manner also allows the reagent to be optimized for detection of certain stages of *T. cruzi* infection.

The present disclosure further provides for a method of standardizing *T. cruzi* antibody detection assays using an immunodiagnostic reagent comprising a plurality of recombinant antibodies, each capable of specifically binding to a different TCA, as a sensitivity panel.

The present disclosure additionally provides for a method for detecting the presence of TCAs which comprises contacting a test sample suspected of containing TCAs with an immunodiagnostic reagent comprising one or more recombinant antibodies, each capable of specifically binding a TCA, under conditions that allow formation of recombinant antibody:antigen complexes and detecting any recombinant antibody:antigen complexes formed.

The present disclosure also encompasses a method for detecting the presence of *T. cruzi* antibodies which comprises contacting a test sample suspected of containing *T. cruzi* antibodies with one or more antigens specific for the *T. cruzi* antibodies, under conditions that allow formation of antigen/antibody complexes, detecting the antigen:antibody complexes, and using an immunodiagnostic reagent comprising one or more recombinant antibodies, each capable of specifically binding one of the antigens used in the method, as a positive control or standardization reagent.

The immunodiagnostic reagents of the present disclosure are suitable for use with assays and kits monitoring *T. cruzi* responses in man as well as other vertebrate species susceptible to *T. cruzi* infection and capable of generating an antibody response thereto. The immunodiagnostic reagents thus have human medical as well as veterinary applications.

The present disclosure also encompasses the use of the recombinant antibodies and variable regions described herein in directed molecular evolution technologies such as phage display technologies, and bacterial and yeast cell surface display technologies, in order to produce novel recombinant antibodies in vitro (See, for example, Johnson et al., *Current Opinion in Structural Biology* 3:564 (1993) and Clackson et al., *Nature* 352:624 (1991)).

Optionally the immunodiagnostic reagent of the disclosure, e.g., the chimeric antibodies, can be used in commercial platform immunoassays.

J. KITS COMPRISING RECOMBINANT ANTIBODIES

The present disclosure further provides for therapeutic, diagnostic and quality control kits comprising one or more recombinant antibodies of the disclosure.

One aspect of the present disclosure provides diagnostic kits for the detection of *T. cruzi*. The kits comprise one or more recombinant antibodies of the present disclosure. The recombinant antibodies can be provided in the kit as detection reagents, either for use to capture and/or detect *T. cruzi* antigens or for use as secondary antibodies for the detection of antigen:antibody complexes. Alternatively, the recombinant antibodies can be provided in the kit as a positive control reagent, a standardization reagent, calibration reagent or a sensitivity panel. In various embodiments, the diagnostic kit can further comprise reagents for detection of *T. cruzi* antigens or reagents for the detection of *T. cruzi* antibodies. In one embodiment, the present disclosure provides a diagnostic kit comprising reagents for detection of *T. cruzi* antibodies, including one or more antigens specific for the *T. cruzi* antibodies, and a positive control or standardization reagent comprising one or more recombinant antibodies of the disclosure, each capable of specifically binding one of the one or more antigens included in the kit.

Thus, the present disclosure further provides for diagnostic and quality control kits comprising one or more antibodies of the disclosure. Optionally the assays, kits and kit components of the disclosure are optimized for use on commercial platforms (e.g., immunoassays on the Prism®, AxSYM®, ARCHITECT® and EIA (Bead) platforms of Abbott Laboratories, Abbott Park, Ill., as well as other commercial and/or in vitro diagnostic assays). Additionally, the assays, kits and kit components can be employed in other formats, for example, on electrochemical or other hand-held or point-of-care assay systems. The present disclosure is, for example, applicable to the commercial Abbott Point of Care (i-STAT®, Abbott Laboratories, Abbott Park, Ill.) electrochemical immunoassay system that performs sandwich immunoassays for several cardiac markers, including TnI, CKMB and BNP. Immunosensors and methods of operating them in single-use test devices are described, for example, in US Patent Applications 20030170881, 20040018577, 20050054078 and 20060160164 which are incorporated herein by reference. Additional background on the manufacture of electrochemical and other types of immunosensors is found in U.S. Pat. No. 5,063,081 which is also incorporated by reference for its teachings regarding same.

Optionally the kits include quality control reagents (e.g., sensitivity panels, calibrators, and positive controls). Preparation of quality control reagents is well known in the art, and is described, e.g., on a variety of immunodiagnostic product insert sheets. Sensitivity panel members optionally can be prepared in varying amounts containing, e.g., known quantities of antibody ranging from "low" to "high", e.g., by spiking known quantities of the antibodies according to the disclosure into an appropriate assay buffer (e.g., a phosphate buffer). These sensitivity panel members optionally are used to establish assay performance characteristics, and further optionally are useful indicators of the integrity of the immunoassay kit reagents, and the standardization of assays.

The antibodies provided in the kit can incorporate a detectable label, such as a fluorophore, radioactive moiety, enzyme, biotin/avidin label, chromophore, chemiluminescent label, or the like, or the kit may include reagents for labeling the antibodies or reagents for detecting the antibodies (e.g., detection antibodies) and/or for labeling the antigens or reagents for detecting the antigen. The antibodies, calibrators and/or controls can be provided in separate containers or pre-dispensed into an appropriate assay format, for example, into microtiter plates.

The kits can optionally include other reagents required to conduct a diagnostic assay or facilitate quality control evaluations, such as buffers, salts, enzymes, enzyme co-factors, substrates, detection reagents, and the like. Other components, such as buffers and solutions for the isolation and/or treatment of a test sample (e.g., pretreatment reagents), may also be included in the kit. The kit may additionally include one or more other controls. One or more of the components of the kit may be lyophilized and the kit may further comprise reagents suitable for the reconstitution of the lyophilized components.

The various components of the kit optionally are provided in suitable containers. As indicated above, one or more of the containers may be a microtiter plate. The kit further can include containers for holding or storing a sample (e.g., a container or cartridge for a blood or urine sample). Where appropriate, the kit may also optionally contain reaction vessels, mixing vessels and other components that facilitate the preparation of reagents or the test sample. The kit may also include one or more instruments for assisting with obtaining a test sample, such as a syringe, pipette, forceps, measured spoon, or the like.

The kit further can optionally include instructions for use, which may be provided in paper form or in computer-readable form, such as a disc, CD, DVD or the like.

K. ADAPTATION OF KITS

The kit (or components thereof), as well as the method of determining the detecting the presence or concentration of *T. cruzi* antigens in a test sample by an assay using the components and methods described herein, can be adapted for use in a variety of automated and semi-automated systems (including those wherein the solid phase comprises a microparticle), as described, e.g., in U.S. Pat. Nos. 5,089,424 and 5,006,309, and as commercially marketed, e.g., by Abbott Laboratories (Abbott Park, Ill.) as ARCHITECT®.

Some of the differences between an automated or semi-automated system as compared to a non-automated system (e.g., ELISA) include the substrate to which the first specific binding partner (e.g., *T. cruzi* capture antibody) is attached (which can impact sandwich formation and analyte reactivity), and the length and timing of the capture, detection and/or any optional wash steps. Whereas a non-automated format such as an ELISA may require a relatively longer incubation time with sample and capture reagent (e.g., about 2 hours) an automated or semi-automated format (e.g., ARCHITECT®, Abbott Laboratories) may have a relatively shorter incubation time (e.g., approximately 18 minutes for ARCHITECT®). Similarly, whereas a non-automated format such as an ELISA may incubate a detection antibody such as the conjugate reagent for a relatively longer incubation time (e.g., about 2 hours), an automated or semi-automated format (e.g., ARCHITECT®) may have a relatively shorter incubation time (e.g., approximately 4 minutes for the ARCHITECT®).

Other platforms available from Abbott Laboratories include, but are not limited to, AxSYM®, IMx® (see, e.g., U.S. Pat. No. 5,294,404, which is hereby incorporated by reference in its entirety), PRISM®, EIA (bead), and Quantum™ II, as well as other platforms. Additionally, the assays, kits and kit components can be employed in other formats, for example, on electrochemical or other hand-held or point-of-care assay systems. The present disclosure is, for example, applicable to the commercial Abbott Point of Care (i-STAT®, Abbott Laboratories) electrochemical immunoassay system that performs sandwich immunoassays. Immunosensors and their methods of manufacture and operation in single-use test devices are described, for example in, U.S. Pat. No. 5,063,081, U.S. Pat. App. Pub. No. 2003/0170881, U.S. Pat. App. Pub. No. 2004/0018577, U.S. Pat. App. Pub. No. 2005/0054078, and U.S. Pat. App. Pub. No. 2006/0160164, which are incorporated in their entireties by reference for their teachings regarding same.

In particular, with regard to the adaptation of a *T. cruzi* antigen assay to the I-STAT® system, the following configuration is preferred. A microfabricated silicon chip is manufactured with a pair of gold amperometric working electrodes and a silver-silver chloride reference electrode. On one of the working electrodes, polystyrene beads (0.2 mm diameter) with immobilized capture antibody are adhered to a polymer coating of patterned polyvinyl alcohol over the electrode. This chip is assembled into an I-STAT® cartridge with a fluidics format suitable for immunoassay. On a portion of the wall of the sample-holding chamber of the cartridge there is a layer comprising the second detection antibody labeled with alkaline phosphatase (or other label). Within the fluid pouch of the cartridge is an aqueous reagent that includes p-aminophenol phosphate.

In operation, a sample suspected of containing a *T. cruzi* antigen is added to the holding chamber of the test cartridge and the cartridge is inserted into the I-STAT® reader. After the second antibody (detection antibody) has dissolved into the sample, a pump element within the cartridge forces the sample into a conduit containing the chip. Here it is oscillated to promote formation of the sandwich between the *T. cruzi* antigen, *T. cruzi* capture antibody, and the labeled detection antibody. In the penultimate step of the assay, fluid is forced out of the pouch and into the conduit to wash the sample off the chip and into a waste chamber. In the final step of the assay, the alkaline phosphatase label reacts with p-aminophenol phosphate to cleave the phosphate group and permit the liberated p-aminophenol to be electrochemically oxidized at the working electrode. Based on the measured current, the reader is able to calculate the amount of *T. cruzi* antigen in the sample by means of an embedded algorithm and factory-determined calibration curve.

It further goes without saying that the methods and kits as described herein necessarily encompass other reagents and methods for carrying out the immunoassay. For instance, encompassed are various buffers such as are known in the art and/or which can be readily prepared or optimized to be employed, e.g., for washing, as a conjugate diluent, and/or as a calibrator diluent. An exemplary conjugate diluent is ARCHITECT® conjugate diluent employed in certain kits (Abbott Laboratories, Abbott Park, Ill.) and containing 2-(N-morpholino)ethanesulfonic acid (MES), a salt, a protein blocker, an antimicrobial agent, and a detergent. An exemplary calibrator diluent is ARCHITECT® human calibrator diluent employed in certain kits (Abbott Laboratories, Abbott Park, Ill.), which comprises a buffer containing MES, other salt, a protein blocker, and an antimicrobial agent.

To gain a better understanding of the disclosure described herein, the following examples are set forth. It will be understood that these examples are intended to describe illustrative embodiments of the disclosure and are not intended to limit the scope of the disclosure in any way.

EXAMPLES

Example 1

Cell Lines Producing Antibodies Against *T. cruzi* Antigen FP3 (Chagas FP3 12-392-150-110)

In this example, a hybridoma cell line that produces mAbs that recognize and bind Chagas FP3 recombinant antigen was produced. Mice were immunized with the FP3 recombinant antigen (SEQ ID NO.:2), the anti-FP3 antibody-producing mice euthanized, spleen cells harvested and fused with myeloma cells, and mAb anti-FP3 hybridoma cell lines were isolated. The resulting cell line HBFP3 was produced.

Immunogen Preparation

The Chagas FP3 antigen cell line was provided by Dr. Louis Kirchoff's laboratory of the University of Iowa, for a seed bank in Lake County, Ill. The cDNA sequence encoding this antigen (SEQ ID NO.:1) was cloned into the pET expression vectors under the control of T7 promoter and expressed in suitable *E. coli* host cells [BLR(DE3)pLysS or BL21 (DE3)]. The T7 RNA polymerase was encoded by the lambda DE3 lysogen inserted into the host bacterial genome and under the control of the lacUVS promoter. Isopropyl β-D-thiogalactopyranoside (IPTG) was added to the cells to induce T7 RNA polymerase expression, which in turn bound to the T7 promoter and resulted in the expression of the cloned gene. Plates of the transformed cells were streaked to isolate a single colony and cell banks were prepared. Subsequently, the *E. coli* was grown, and a cell paste was prepared for purification.

First, the recombinant FP3 antigen was purified from clarified supernatant by recirculating the clarified supernatant during loading. Second, spuriously bound contaminants where removed from the Immobilized Metal Affinity Chromatography (IMAC) column by washing the affinity column with a high salt buffer. Third, the His-tagged (amino end) recombinant FP3 polypeptide was eluted from the column by competitively removing His-tagged antigen with imidazole. Subsequently, the eluted proteins were fractioned and analyzed by sodium dodecyl sulfate-polyacrylamide gel electrophoresis (SDS-PAGE). Fractions that contained the recombinant FP3 antigen without significant contamination were pooled and concentrated. After concentration, the FP3 antigen was further purified by size exclusion chromatography using a 2000 ml Sephacryl S-300 sizing column, analyzed by SDS-PAGE and concentrated.

Animal Immunization

RBf/dnJ female mice (all mice were obtained from Jackson Laboratories; Bar Harbor, Me.) were immunized twice with purified Chagas FP4 recombinant antigen (containing the target FP3 sequence) and once with purified Chagas FP3 recombinant antigen, using the Freunds Adjuvant System, prior to checking the antisera for sufficient titer. The inoculum was prepared by diluting the antigen in 0.9% sodium chloride and emulsifying with an equal volume of adjuvant. At weeks 0 and 3, a 20 μg boost of FP4 (containing the target FP3 sequence) was administered to the mice. At week 6, a 10 μg boost of FP3 was administered to the mice. Freunds Complete Adjuvant was used for the primary boost delivered subcutaneously, and Freunds Incomplete Adjuvant was used for the next 2 intradermal boosts. Two weeks after the third boost, a sera sample was taken for a specific anti-*T. cruzi* titer test, which resulted in the selection of mouse #241 for the fusion experiment. Three days prior to the fusion, mouse #241 was administered a pre-fusion boost of 5 μg of the FP3 recombinant antigen.

Hybridoma Creation (Cell Fusion Experiment)

Hybridomas were developed using the polyethylene glycol (PEG)-mediated fusion technique described in Galfre et al. (Galfre, G., et al. 1977. Antibodies to major histocompatibility antigens produced by hybrid cell lines. *Nature.* 266:550-2). The RBf/dnJ mouse #241 was euthanized three days after the pre-fusion boost, and the spleen was harvested. The B-cells were perfused from the spleen, washed and re-suspended in an equal number of SP2/0 myeloma cells (ATTC deposit CRL-1581). The total cells were pelleted, and the fusion was performed with 1 ml of polyethylene glycol (PEG) and cultured at 37° C. in HAT-supplemented GIBCO® Hybridoma Serum Free Medium (H-SFM; Invitrogen Corp., Carlsbad, Calif.) with 10% fetal bovine serum (FBS;

Hyclone; Logan, Utah). Cells were plated into 96-well tissue culture plates and incubated in a humidified 37° C. incubator. The hybrids were tested 10-14 days later for anti-*T. cruzi* FP3 reactivity in a microtiter enzyme immunoassay (EIA). The results indicated hybrid 12-392 secreted anti-FP3 specific antibody.

Hybridoma Cloning and Subcloning

Hybridoma 12-392 was selected for limiting dilution cloning. The cells were suspended and then serially diluted $10^4$, $10^5$ and $10^6$ into 20 ml of H-SFM with 10% FBS. Each dilution was plated into a 96-well tissue culture plate with 0.2 ml cell suspension per well. The plates were incubated for 10-14 days at 37° C. in a humidified incubator. As growth became apparent, the supernates were tested in an anti-FP3 microtiter EIA that resulted in the selection of clone 12-392-150.

Clone 12-392-150 was selected for subcloning using fluorescence activated cell sorting (FACS). A cell suspension was stained with goat anti-mouse-Alexa Fluor 488 (Invitrogen Corp., Carlsbad, Calif.). Single cell isolates from the top 5-8% of this stained cell population were deposited in a 96-well tissue culture plate with 0.2 ml of H-SFM with 10% FBS. The plates were incubated for 10-14 days at 37° C. in a humidified incubator. As growth became apparent, the supernates were tested in an anti-FP3 microtiter EIA that resulted in the selection of clone 12-392-150-110 (HBFP3).

HBFP3 was expanded in tissue culture to a 850 cm² roller bottle, cell passage 5, in H-SFM with 10% FBS. The pass 5 cell suspension was pelleted, re-suspended in freeze medium and dispensed into cryovials. The vials were stored in liquid nitrogen storage tanks.

Example 2

Cell Lines Producing Antibodies Against Chagas TcF Recombinant Antigen (Chagas 9-638-132-115)

Immunogen Source

The purified TcF recombinant antigen (containing the PEP2 sequence) used for animal immunizations was obtained from Corixa Corporation (Seattle, Wash.).

Animal Immunization

RBf/dnJ female mice were immunized three times with purified Chagas TcF recombinant antigen, using the Freunds Adjuvant System, prior to checking the antisera for sufficient titer. The inoculum was prepared by diluting the antigen in 0.9% sodium chloride and emulsifying with an equal volume of adjuvant. At weeks 0, 6, and 12, a 20 µg boost of TcF was administered to the mice. Freunds Complete Adjuvant was used for the primary boost delivered subcutaneously and Freunds Incomplete Adjuvant was used for the next 2 intradermal boosts. Two weeks after the 3rd boost, a sera sample was taken for a specific anti-*T. cruzi* titer test, which resulted in the selection of mouse #115 for the fusion experiment. Three days prior to the fusion, mouse #115 was administered a pre-fusion boost of 10 µg of the TcF recombinant antigen and 10 µg of the TcF Pep2 peptide.

Hybridoma Creation

Hybridomas were developed using PEG-mediated fusion technique described in Galfre et al. (Galfre et al., 1977). The RBf/dnJ mouse #115 was euthanized three days after the pre-fusion boost, and the spleen was harvested. The B-cells were perfused from the spleen, washed and re-suspended in an equal number of SP2/0 myeloma cells (ATTC deposit CRL-1581). The total cells were pelleted, and the fusion was performed with 1 ml of PEG and cultured at 37° C. in HAT-supplemented GIBO® H-SFM (Invitrogen Corp., Carlsbad, Calif.) with 10% FBS (Hyclone, Logan, Utah). Cells were plated into 96-well tissue culture plates and incubated in a humidified 37° C. incubator. The hybrids were tested 10-14 days later for anti-*T. cruzi* Pep2 reactivity in a microtiter EIA. The results indicated hybrid 9-638 secreted anti-Pep2 specific antibody.

Hybridoma Cloning and Subcloning

Hybridoma 9-638 was selected for limiting dilution cloning. The cells were suspended and then serially diluted $10^4$, $10^5$ and $10^6$ into 20 ml of H-SFM with 10% FBS. Each dilution was plated into a 96-well tissue culture plate with 0.2 ml cell suspension per well. The plates were incubated for 10-14 days at 37° C. in a humidified incubator. As growth became apparent, the supernates were tested in an anti-Pep2 microtiter EIA, and clone 9-638-132 was selected.

Clone 9-638-132 was selected for subcloning using FACS. A cell suspension was stained with goat anti-mouse-Alexa Fluor 488. Single cell isolates from the top 1% of this stained cell population were deposited in a 96-well tissue culture plate with 0.2 ml of H-SFM with 10% FBS. The plates were incubated for 10-14 days at 37° C. in a humidified incubator. As growth became apparent, the supernates were tested in an anti-Pep2 microtiter EIA, and clone 9-638-132-115 was selected.

Clone 9-638-132-115 was expanded in tissue culture to a 850 cm² roller bottle, cell passage 6, in H-SFM with 10% FBS. The pass 5 cell suspension was pelleted. The pellet was then re-suspended in freeze medium and dispensed into cryovials. The vials were stored in liquid nitrogen storage Example 3

Cell Lines Producing Antibodies Against Chagas FP10 Recombinant Antigen (Chagas 10-745-140)

Immunogen Source

The Chagas FP10 antigen (SEQ ID NO.:6) cell line was obtained from the laboratory of Dr. Louis Kirchoff, University of Iowa, for a seed bank in Lake County. The cDNA sequence (SEQ ID NO.:5) encoding this antigen was cloned into the pET expression vectors, and the cells were processed and recombinant antigen purified as outlined in Example 1.

Animal Immunization

RBf/dnJ female mice were immunized three times with purified Chagas FP10 recombinant antigen using the Freunds Adjuvant System prior to checking the antisera for sufficient titer. The inoculum was prepared by diluting the antigen in 0.9% sodium chloride and emulsifying with an equal volume of adjuvant. At weeks 0, 3, and 6, a 20 µg boost was administered to the mice. Freunds Complete Adjuvant was used for the primary boost delivered subcutaneously, and Freunds Incomplete Adjuvant was used for the next 2 intradermal boosts. Two weeks after the 3rd boost, a sera sample was taken for a specific anti-*T. cruzi* titer test, and mouse #230 was selected for the fusion experiment. Three days prior to the fusion, mouse #230 was administered a pre-fusion boost consisting of 25 µg of the FP10 recombinant antigen and 25 µg of a 14 amino acid synthetic peptide representing the L-domain of the FP10 recombinant antigen.

Hybridoma Creation

Hybridomas were developed using PEG-mediated fusion technique described in Galfre et al. (Galfre et al., 1977). The RBf/dnJ mouse #230 was euthanized three days after the pre-fusion boost, and the spleen was harvested. The B-cells were perfused from the spleen, washed and re-suspended in an equal number of SP2/0 myeloma cells (ATTC deposit CRL-1581). The total cells were pelleted, and the fusion was performed with 1 ml of PEG and cultured at 37° C. in HAT-supplemented GIBCO® H-SFM (Invitrogen Corp., Carlsbad, Calif.) with 10% FBS (Hyclone, Logan, Utah). Cells were plated into 96-well tissue culture plates and incubated in a humidified 37° C. incubator. The resulting hybridomas were tested 10-14 days later for anti-*T. cruzi* FP10 reactivity in an EIA. A hybridoma secreting anti-*T. cruzi* FP10 mAb known as 10-745 was selected.

Hybridoma Cloning

Hybrid 10-745 was selected for a limiting dilution cloning. The cells were suspended and then serially diluted $10^4$, $10^5$ and $10^6$ into 20 ml of H-SFM with 10% FBS. Each dilution was plated into a 96-well tissue culture plate with 0.2 ml cell suspension per well. The plates were incubated for 10-14 days at 37° C. in a humidified incubator. As growth became apparent, the supernates were tested in an anti-FP10 microtiter EIA that resulted in the selection of clone 10-745-140.

Clone 10-745-140 was expanded in tissue culture to a T75-flask, cell passage 2, in IMDM with 10% FBS. The pass 2 cell suspension was pelleted by centrifugation. The pellet was then resuspended in freeze medium and dispensed into appropriately labeled cryovials. The vials were stored in liquid nitrogen storage tanks.

Example 4

Cell Lines Producing Antibodies Against Chagas FRA Recombinant Antigen (Chagas FRA 8-367-171)

Immunogen Source

The *T. cruzi* antigen cell line containing the FRA region (SEQ ID NO.:8) comprised in the FP6 polypeptide, was obtained from the laboratory of Dr. Louis Kirchoff, University of Iowa, for a seed bank in Lake County. The cDNA sequence encoding this antigen (SEQ ID NO.:7) was cloned into the pET expression vectors, and the cells were processed and recombinant antigen purified as outlined in Example 1.

Animal Immunizations

BALB/c female mice were immunized three times with purified Chagas recombinant antigen FP6 using the Freunds Adjuvant System prior to checking the antisera for sufficient titer. The inoculum was prepared by diluting the antigen in 0.9% sodium chloride and emulsifying with an equal volume of adjuvant. At weeks 0, 4, and 10, a 10 μg boost was administered to the mice. Freunds Complete Adjuvant was used for the primary boost delivered subcutaneously and Freunds Incomplete Adjuvant was used for the next 2 intradermal boosts. Two weeks after the 3rd boost, a sera sample was taken for a specific anti-*T. cruzi* titer test, and mouse #1907 was selected for the fusion experiment. Three days prior to fusion, mouse #1907 was administered a pre-fusion boost consisting of 25 μg of the recombinant antigen and 25 μg of a synthetic peptide representing the FRA-domain of the recombinant antigen.

Hybridoma Creation

Hybridomas were developed using PEG-mediated fusion technique described in Galfre et al. (Galfre et al., 1977). The BALB/c mouse #1907 was euthanized three days after the pre-fusion boost, and the spleen was harvested. The B-cells were perfused from the spleen, washed and re-suspended in an equal number of SP2/0 myeloma cells (ATTC deposit CRL-1581). The total cells were pelleted, and the fusion was performed with 1 ml of PEG and cultured at 37° C. in HAT-supplemented GIBCO® H-SFM (Invitrogen Corp., Carlsbad, Calif.) with 10% FBS (Hyclone, Logan, Utah). Cells were plated into 96-well tissue culture plates and incubated in a humidified 37° C. incubator. The resulting hybridomas were tested 10-14 days later for anti-*T. cruzi* FRA-domain reactivity in an EIA. A hybridoma secreting anti-*T. cruzi* FRA-domain mAb known as 8-367 was selected.

Hybridoma Cloning

Hybrid 8-367 was selected for a limiting dilution cloning. The cells were suspended and then serially diluted $10^4$, $10^5$ and $10^6$ dilutions into 20 ml of H-SFM with 10% FBS. Each dilution was plated into a 96-well tissue culture plate with 0.2 ml cell suspension per well. The plates were incubated for 10-14 days at 37° C. in a humidified incubator. As growth became apparent, the supernates were tested in an anti-FRA microtiter EIA, and clone 8-367-171 was selected.

Clone 8-367-171 was expanded in tissue culture to a T75-flask, cell passage 3, in IMDM with 10% FBS. The pass 2 cell suspension was pelleted, re-suspended in freeze medium and dispensed into cryovials. The vials were stored in liquid nitrogen storage tanks.

Example 5

Cell Lines Producing Chimeric Anti-*T. cruzi* FP3 mAbs (Chagas FP3 12-392-150CHO2580-104)

In this and the subsequent examples directed towards the creation of mammalian cell lines that express mouse-human chimeric monoclonal antibodies, the following overall approach was taken. After identifying hybridoma cells lines that secreted the desired mAbs (such as the hybridomas of Examples 1-4), mRNA was isolated from these cells and the antibody gene sequences identified. The $V_L$ and $V_H$ sequences were then cloned into pBOS vectors, which supplied the human antibody constant sequences (Mizushima S, Nagata S., "pEF-BOS, a powerful mammalian expression vector." *Nucleic Acids Res.* 1990 Sep. 11; 18(17):5322 and US 2005/0227289 (incorporated by reference for its teachings regarding the use of these vectors and the vectors themselves)), which were then co-transfected in a transient expression system to confirm that the resulting chimeric antibodies were functional. Upon confirmation, the $V_L$ sequences were subcloned into pJV, and the $V_H$ sequences into pBV; these vectors where then used to construct a stable pBJ expression vector. The pJV plasmid was obtained from Abbott Laboratories (Abbott Bioresearch Center, Worcester, Mass.) and comprises a SV40 promoter, a murine DHFR gene, an enhancer, a promoter, and a lambda stuffer. The pBV plasmid (also obtained from Abbott Laboratories, Abbott Bioresearch Center, Worcester, Mass.) comprises an enhancer, a promoter, and a lambda stuffer. Chinese Hamster Ovary (CHO) cells were then transfected with pBJ, stable transfectants selected, and the secreted antibodies tested again. FIG. 1 shows a schematic summary of the chimeric antibodies, where the murine variable region genes (antigen binding portion) are transferred into vectors where the human constant region genes are appended.

Identification of Mouse $V_H$ and $V_L$ Sequences

Hybridoma cell line HBFP3 (Example 1) was cultured in H-SFM to obtain ~5×$10^6$ cells for mRNA purification according to standard mRNA extraction protocols. The purified mRNA was used as a template with a mouse Ig primer set (Novagen (EMD Biosciences, Inc.); Madison, Wis.) in an RT-PCR reaction. Positive PCR products were observed from the heavy chain (H) primers B and C (HB and HC clones) and from the light chain (L) primers A, B, C, and G (LA, LB, LC, and LG clones). All positive PCR products were gel-purified and cloned into pCR TOPO 2.1 TA vector (Invitrogen Corp., Carlsbad, Calif.). The plasmid DNA was purified from transformed bacterial cells and the $V_H$ or $V_L$ inserts were confirmed by EcoRI digestion for each RT-PCR reaction that generated appropriately sized products. The correct $V_H$ or $V_L$ gene sequence was selected after sequence alignments confirmed a consensus sequence among the clones. Chagas TOPO-TA clone HB1 contained the correct $V_H$ gene sequence, and Chagas TOPO-TA clone LG3 contained the correct $V_L$ gene sequence.

Cloning Murine $V_H$ and $V_L$ Genes into pBOS Vectors

A pair of PCR primers containing a partial Kappa signal sequence with an Nru I site on the 5'-primer, and a BsiW I site on the 3'-primer was used to amplify the mouse $V_L$ gene from TOPO clone LG3. Additionally, a pair of primers containing a partial heavy chain signal sequence and an Nru I site on the 5'-primer, and Sal I site on 3'-primer was used to amplify the mouse $V_H$ gene from TOPO clone HB1. The $V_L$ PCR product was digested with Nru I and BsiW I restriction enzymes and ligated into pBOS-hCk vector digested with the same enzymes. The $V_H$ PCR product was digested with Nru I and Sal I restriction enzymes and ligated into pBOS-hCg1 vector digested with the same enzymes. Plasmids from a number of transformed bacterial colonies were sequenced to confirm the presence of either the Chagas $V_H$ or $V_L$ gene in their respective vectors. Chagas 12-392-150 $V_H$_pBOS-H clone 4 and Chagas 12-392-150 $V_L$_pBOS-L clone 5 were deemed correct.

Chimeric mAb Production and Functional Confirmation

Endotoxin-free plasmid preparations of Chagas 12-392-150 $V_H$_pBOS-H clone 1 and Chagas 12-392-150 $V_L$_pBOS-L clone 4 were used for transient transfection into COS 7L cells by electroporation (GENE PULSER®, Bio-Rad; Hercules, Calif.). The transfected cells were incubated at 37° C. in a 5% $CO_2$ incubator for three days. The chimeric antibody produced by the COS 7L cells were harvested by centrifugation at 4000 rpm for 20 minutes and then purified using a protein A affinity column (POROS A; Applied Biosystems; Foster City, Calif.). To confirm activity, the harvested antibody was assayed using surface plasmon resonance on a BIACORE® instrument (Biacore (GE Healthcare); Piscataway, N.J.).

CHO Cell Line Stable Expression Vector Cloning

Figure 2:
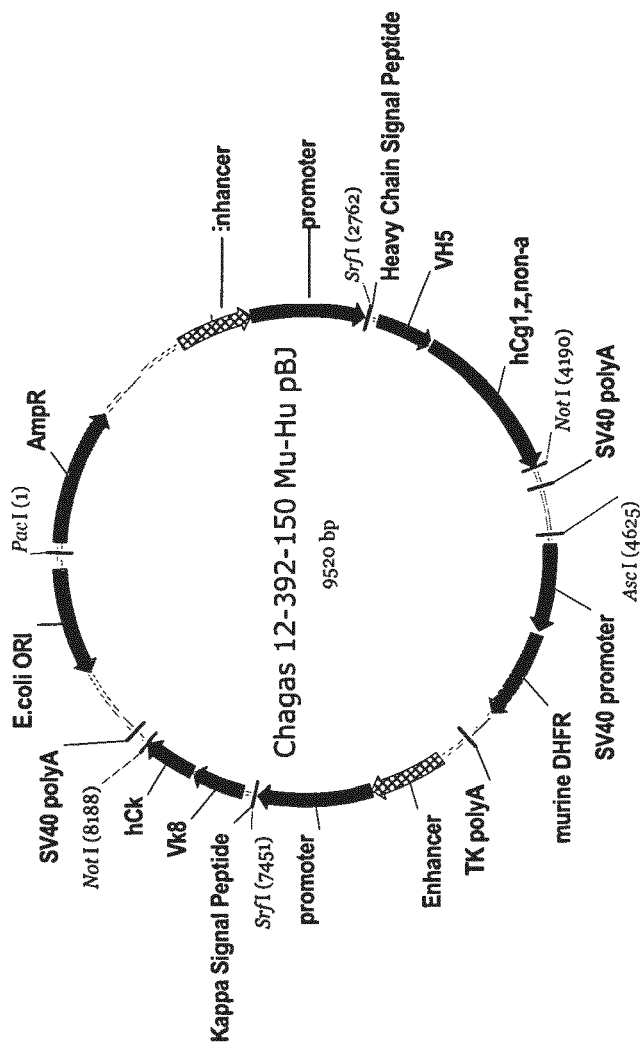
FIG. 2 depicts schematically the plasmid Chagas 12-392-150 Mu-Hu_pBJ, plasmid size: 9520 nucleotides. An ampicillin resistance gene ORF is located at bases 60-917; an enhancer is located at bases 1551-2021; a promoter is located at bases 2023-2744; a heavy chain signal peptide is located at bases 2772-2828; a $V_H$ gene is located at bases 2829-3194; a human constant hgG1, z, non-a is located at bases 3195-4187; a SV40 Poly A is located at bases 4219-4413; a SV40 promoter is located at bases 4684-5229; a murine DHFR is located at bases 5257-5820; a TK poly A is located at bases 5847-6213; an enhancer is located at bases 6241-6711; a promoter is located at bases 6712-7433; a kappa signal peptide is located at bases 7460-7525; a $V_L$ gene is located at bases 7526-7861; a human constant kappa is located at bases 7862-8185; a SV40 Poly A is located at bases 8198-8392; and a pUC origin is located at bases 8759-9432 (complementary).

Chagas 12-392-150 $V_H$_pBOS-H clone 1 and Chagas 12-392-150 $V_L$_pBOS-L clone 4 were used to construct a plasmid to generate a stable, transfected CHO cell line. First, Srf I and Not I were used to isolate the $V_H$-CH and $V_L$-CL genes from the pBOS vectors; these fragments were then cloned into pBV or pJV vectors, respectively. Both vectors were acquired from Abbott Bioresearch Center (Worcester, Mass.) and contained regulatory sequences needed for the expression of the antibody genes. The resulting pBV and pJV clones were analyzed by Srf I/Not I restriction enzyme digestion and sequenced to determine Chagas 10-745 $V_H$_pBV clone 4 and Chagas 12-392-150_pJV clone 1 were correct. Second, the correct pBV or pJV clones were both digested with Pac I and Asc I, and the resulting $V_H$-CH and $V_L$-CL-containing DNA fragments were ligated to form a single pBJ plasmid that contained both heavy and light chain genes. The pBJ clones were screened by Srf I/Not I digestion to confirm the presence of both antibody genes. The plasmid map for Chagas 12-392-150 Mu-Hu_pBJ clone 4 is shown in FIG. 2; the double-stranded polynucleotide sequences of VH gene and VL gene containing regions (and flanking sequences) are shown in FIGS. 3A-C.

CHO cell line B3.2 acquired from the Abbott Bioresearch Center containing a deficient dihydrofolate reductase (DHFR) gene was used for transfection and stable antibody expression. CHO B3.2 cells were transfected with Chagas 12-392-150 Mu-Hu_pBJ clone 1 using calcium phosphate-mediated transfection. The transfected CHO cells were cultured for several weeks with media lacking thymidine to select for those cells that had incorporated the functional DHFR gene present in the pBJ plasmid. Fluorescence-activated cell sorting (FACS) was used to sort individual cells from the transfected pool into 96-well plates. An antigen-specific EIA was used to rank antibody production among the clones, and the highest producers were expanded and re-assayed. Clones were then weaned into serum-free media. The growth characteristics, antibody production and clonality of the clones were monitored. Chagas FP3 clone 12-392-150 CHO 2580-104 was sub-cloned by sorting individual cells into 96-well plates and then expanded to produce purified antibody.

Example 6

Cell Lines Producing Chimeric Anti-*T. cruzi* Pep2 Epitope (Anti-TcF and Anti-FP6) mAbs (Chagas Pep2 Clone 9-638-1928)

Identification of Mouse $V_H$ and $V_L$ Sequences

Hybridoma cell line HBPep2 (Example 2) was cultured in H-SFM to obtain ~5×10⁶ cells for mRNA purification according to standard mRNA extraction protocols. The purified mRNA was used as a template with a mouse Ig primer set (Novagen (EMD Biosciences, Inc.)) for a RT-PCR reaction. Positive PCR products were observed from the heavy chain (H) primers B and E (HB and HE clones) and from the light chain (L) primers B, C, D, E, F and G (LB, LC, LD, LE, LF and LG clones). All positive PCR products were gel-purified and cloned into pCR TOPO 2.1 TA vector (Invitrogen Corp., Carlsbad, Calif.). The plasmid DNA was purified from transformed bacterial cells and the $V_H$ or $V_L$ inserts were confirmed by EcoRI digestion for each RT-PCR reaction that generated appropriately sized products. The correct $V_H$ or $V_L$ gene sequence was selected after sequence alignments confirmed a consensus sequence among the clones. Chagas TOPO-TA clone HE2 contained the correct $V_H$ gene sequence, and Chagas TOPO-TA clone LG1 contained the correct $V_L$ gene sequence.

Cloning Murine $V_H$ and $V_L$ Genes into pBOS Vectors

A pair of PCR primers containing a partial Kappa signal sequence and an Nru I site on the 5'-primer, and a BsiW I site on the 3'-primer was used to amplify the mouse $V_L$ gene from TOPO clone LG1. Additionally, a pair of primers containing a partial heavy chain signal sequence and an Nru I site on the 5'-primer, and Sal I site on 3'-primer was used to amplify the mouse $V_H$ gene from TOPO clone HE2. The $V_L$ PCR product was digested with Nru I and BsiW I restriction enzymes and ligated into pBOS-hCk vector digested with the same enzymes. The $V_H$ PCR product was digested with Nru I and Sal I restriction enzymes and ligated into pBOS-hCg1 vector digested with the same enzymes. Plasmids from a number of transformed bacterial colonies were sequenced to confirm the presence of either the Chagas $V_H$ or $V_L$ gene in their respective vectors. Chagas 9-638 $V_H$_pBOS-H clone A2 and Chagas 9-638 $V_L$_pBOS-L clone B6 were deemed correct.

Chimeric mAb Production and Functional Confirmation

Endotoxin-free plasmid preparations of Chagas 9-638 $V_H$_pBOS-H clone A2 and Chagas 9-638 $V_L$_pBOS-L clone B6 were used for transient transfection into COS 7L cells by electroporation (GENE PULSER®, Bio-Rad, Hercules, Calif.). The transfected cells were incubated at 37° C. in a 5% $CO_2$ incubator for three days. The chimeric antibody produced by the COS 7L cells were harvested by centrifugation at 4000 rpm for 20 minutes and then purified using a protein A affinity column (POROS A; Applied Biosystems). To confirm activity, the harvested antibody was assayed using surface plasmon resonance on a BIACORE® instrument (Biacore (GE Healthcare); Piscataway, N.J.). Affinity was approximately 2.6 nM.

CHO Cell Line Stable Expression Vector Cloning

Figure 4:
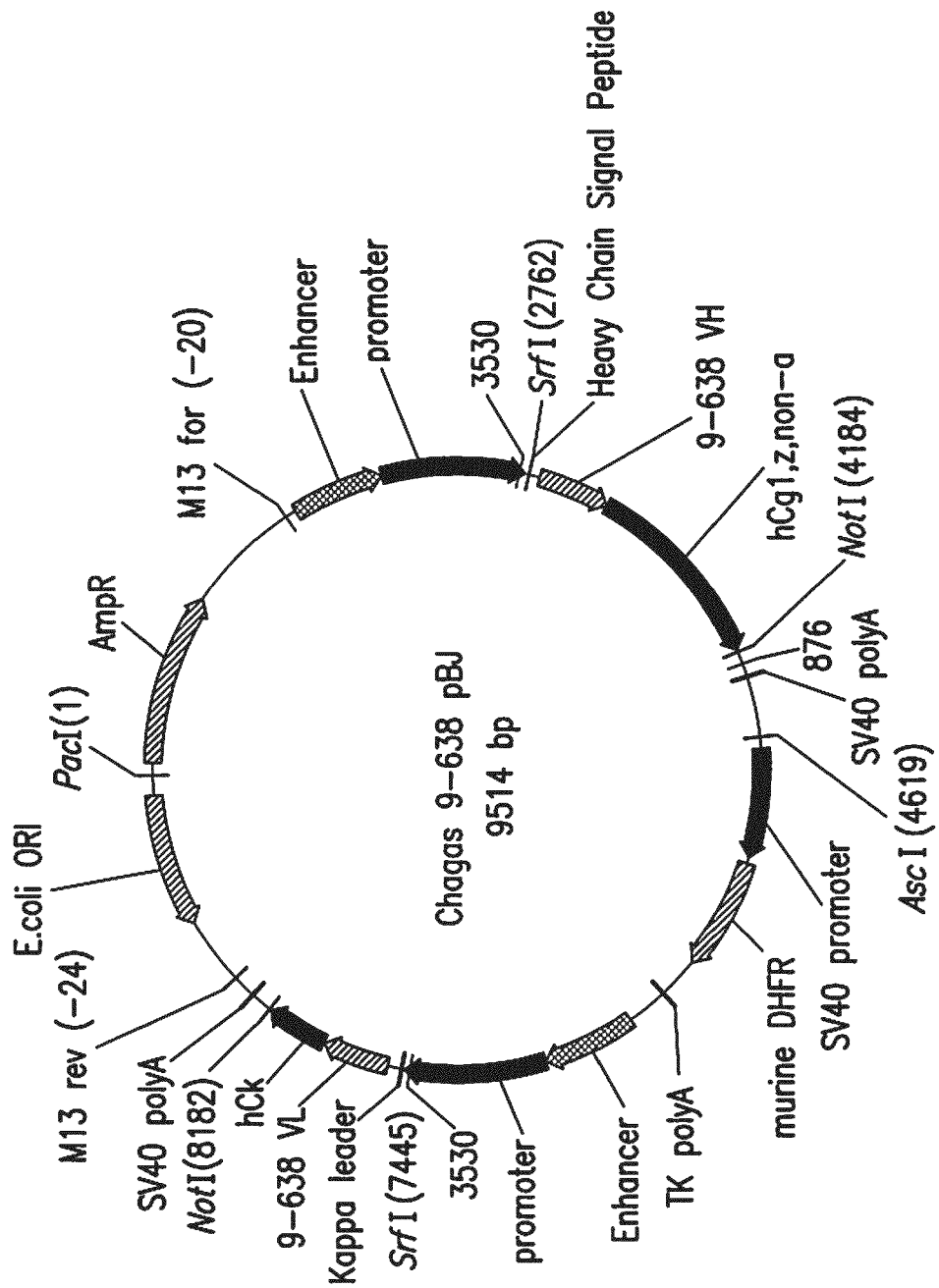
FIG. 4 depicts schematically the plasmid Chagas 9-638 Mu-Hu_pBJ, plasmid size: 9514 nucleotides. An ampicillin resistance gene ORF is located at bases 60-917; an enhancer is located at bases 1551-2021; a promoter is located at bases 2023-2744; a heavy chain signal peptide is located at bases 2772-2828; a $V_H$ gene is located at bases 2829-3188; a human constant hgG1, z, non-a is located at bases 3189-4181; a SV40 poly A is located at bases 4213-4407; a SV40 promoter is located at bases 4678-5223; a murine DHFR is located at bases 5251-5814; a TK poly A is located at bases 5841-6207; an enhancer is located at bases 6235-6705; a promoter is located at bases 6706-7427; a kappa signal peptide is located at bases 7454-7519; a $V_L$ gene is located at bases 7520-7858; a human constant kappa is located at bases 7859-8179; a SV40 Poly A is located at bases 8192-8386; and a pUC origin is located at bases 8753-9426 (complementary).
Figure 5:
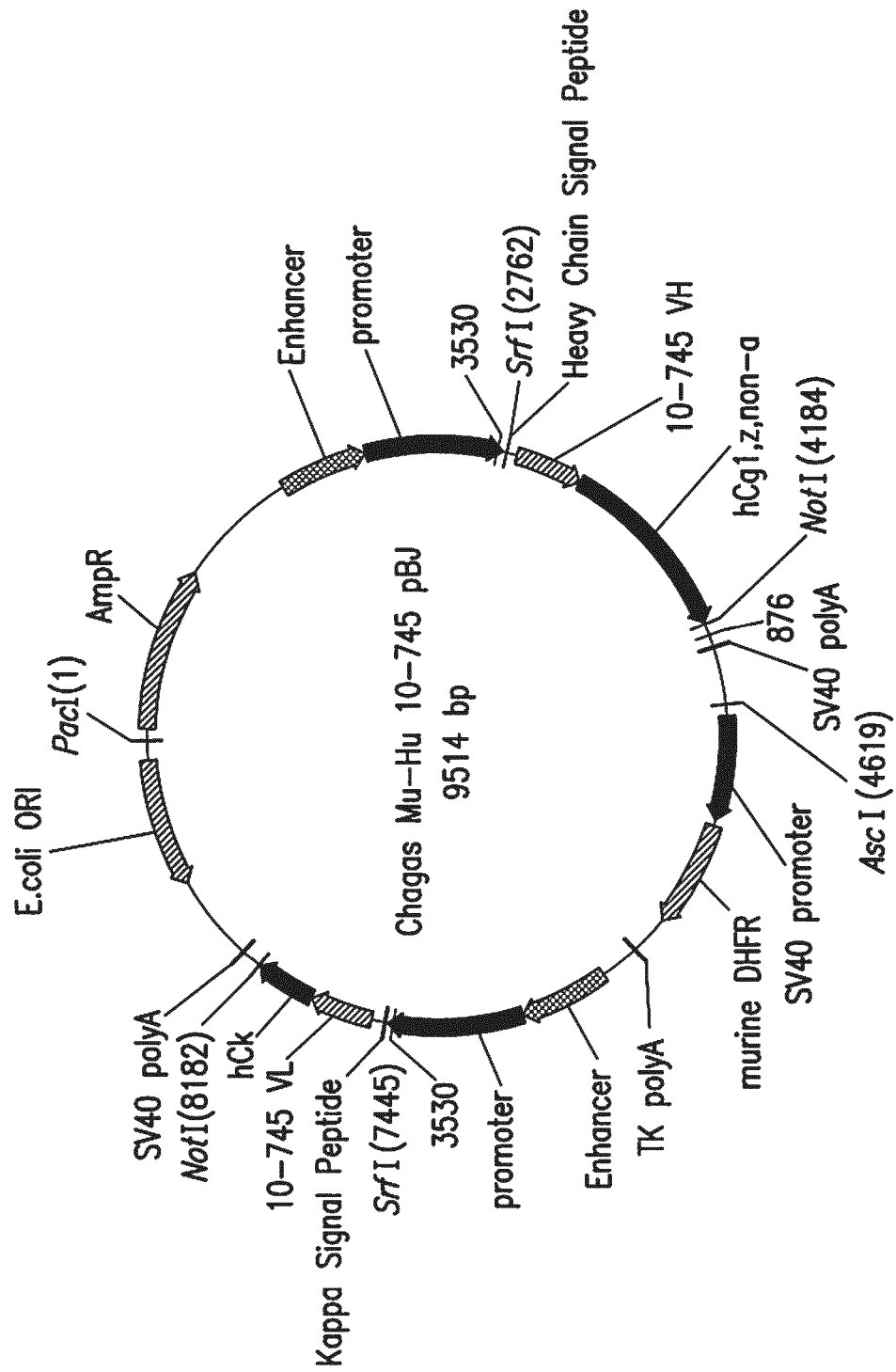
FIG. 5 depicts schematically the plasmid Chagas 10-745 Mu-Hu_pBJ, plasmid size: 9514 nucleotides. An ampicillin resistance gene ORF is located at bases 60-917; an enhancer is located at bases 1551-2021; a promoter is located at bases 2023-2744; a heavy chain signal peptide is located at bases 2772-2828; a $V_H$ gene is located at bases 2829-3188; a human constant IgG1, z, non-a is located at bases 3189-4181; a SV40 Poly A is located at bases 4213-4407; a SV40 promoter is located at bases 4678-5223; a Murine DHFR is located at bases 5251-5814; a TK poly A is located at bases 5841-6207; an enhancer is located at bases 6235-6705; a promoter is located at bases 6706-7427; a kappa signal peptide is located at bases 7454-7519; a $V_L$ gene is located at bases 7520-7855; a human constant kappa is located at bases 7856-8179; a SV40 poly A is located at bases 8192-8386; and a pUC origin bases 8753-9426 (complementary).

Chagas 9-638 $V_H$_pBOS-H clone A2 and Chagas 9-638 $V_L$_pBOS-L clone B6 were used to construct a plasmid to generate a stable, transfected CHO cell line. First, Srf I and Not I were used to isolate the $V_H$-CH and $V_L$-CL genes from the pBOS vectors; these fragments were then cloned into pBV or pJV vectors, respectively. The resulting pBV and pJV clones were analyzed by Srf I/Not I restriction enzyme digestion and sequenced to determine Chagas 9-638 $V_H$_pBV clone 10 and Chagas 9-638_pJV clone 10 were correct. Second, the correct pBV or pJV clones were both digested with Pac I and Asc I, and the resulting $V_H$-CH and $V_L$-CL-containing DNA fragments were ligated to form a single pBJ plasmid that contains both heavy and light chain genes. The pBJ clones were screened by Srf I/Not I digestion to confirm the presence of both antibody genes. The plasmid map for Chagas 9-638 Mu-Hu_pBJ clone 2 is shown in FIG. 4.

CHO cell line B3.2 acquired from the Abbott Bioresearch Center containing a deficient DHFR gene was used for transfection and stable antibody expression. CHO B3.2 cells were transfected with Chagas 9-638 Mu-Hu_pBJ clone 2 using calcium phosphate-mediated transfection. The transfected CHO cells were cultured for several weeks with media lacking thymidine to select for those cells that had incorporated the functional DHFR gene present in the pBJ plasmid. FACS was used to sort individual cells from the transfected pool into 96-well plates. An antigen-specific EIA was used to rank antibody production among the clones, and the highest producers were expanded and re-assayed. Clones were then weaned into serum-free media. The growth characteristics, antibody production and clonality of the clones were monitored. Chagas Pep2 clone 9-638-1145 was chosen and re-subcloned by sorting individual cells into 96-well plates, and then Chagas Pep2 clone 9-638-1928 expanded to produce purified antibody.

Example 7

Cell Lines Producing Chimeric Anti-*T. cruzi* FP10 mAbs (Chagas FP10 10-745-3796)

Identification of Mouse $V_H$ and $V_L$ Sequences

Hybridoma cell line HBFP10 (Example 3) was cultured in H-SFM to obtain ~5×10$^6$ cells for mRNA purification according to standard mRNA extraction protocols. The purified mRNA was used as a template with a mouse Ig primer set (Novagen (EMD Biosciences, Inc.)) for a RT-PCR reaction. Positive PCR products were observed from the heavy chain (H) primers B (HB clones) and from the light chain (L) primers B, C, and G (LB, LC and LG clones). All positive PCR products were gel-purified and cloned into pCR TOPO 2.1 TA vector (Invitrogen Corp., Carlsbad, Calif.). The plasmid DNA was purified from transformed bacterial cells and the $V_H$ or $V_L$ inserts were confirmed by EcoRI digestion for each RT-PCR reaction that generated appropriately sized products. The correct $V_H$ or $V_L$ gene sequence was selected after sequence alignments confirmed a consensus sequence among the clones. Chagas TOPO-TA clone HB3 contained the correct $V_H$ gene sequence, and Chagas TOPO-TA clone LG1 contained the correct $V_L$ gene sequence.

Cloning Murine $V_H$ and $V_L$ Genes into pBOS Vectors

A pair of PCR primers containing a partial Kappa signal sequence and an Nru I site on the 5'-primer, and a BsiW I site on the 3'-primer was used to amplify the mouse $V_L$ gene from TOPO clone LG1. Additionally, a pair of primers containing a partial heavy chain signal sequence and an Nru I site on the 5'-primer, and Sal I site on 3'-primer was used to amplify the mouse $V_H$ gene from TOPO clone HB3. The $V_L$ PCR product was digested with Nru I and BsiW I restriction enzymes and ligated into pBOS-hCk vector digested with the same enzymes. The $V_H$ PCR product was digested with Nru I and Sal I restriction enzymes and ligated into pBOS-hCg1 vector digested with the same enzymes. Plasmids from a number of transformed bacterial colonies were sequenced to confirm the presence of either the Chagas $V_H$ or $V_L$ gene in their respective vectors. Chagas 10-745 $V_H$_pBOS-H clone 4 and Chagas 10-745 $V_L$_pBOS-L clone 5 were deemed correct.

Chimeric mAb Production and Functional Confirmation

Endotoxin-free plasmid preparations of Chagas 10-745 $V_H$_pBOS-H clone 4 and Chagas 10-745 $V_L$_pBOS-L clone 5 were used for transient transfection into COS 7L cells by electroporation (GENE PULSER®, Bio-Rad). The transfected cells were incubated at 37° C. in a 5% $CO_2$ incubator for three days. The chimeric antibody produced by the COS 7L cells were harvested by centrifugation at 4000 rpm for 20 minutes and then purified using a protein A affinity column (POROS A; Applied Biosystems). To confirm activity, the harvested antibody was assayed using surface plasmon resonance on a BIACORE® instrument (Biacore (GE Healthcare)).

CHO Cell Line Stable Expression Vector Cloning

Chagas 10-745 $V_H$_pBOS-H clone 4 and Chagas 10-745 $V_L$_pBOS-L clone 5 were used to construct a plasmid to generate a stable, transfected CHO cell line. First, Srf I and Not I were used to isolate the $V_H$-CH and $V_L$-CL genes from the pBOS vectors; these fragments were then cloned into pBV or pJV vectors, respectively. The resulting pBV and pJV clones were analyzed by Srf I/Not I restriction enzyme digestion and sequenced to determine Chagas 10-745 $V_H$_pBV clone 1 and Chagas 10-745_pJV clone 1 were correct. Second, the correct pBV or pJV clones were both digested with Pac I and Asc I, and the resulting $V_H$-CH and $V_L$-CL-containing DNA fragments were ligated to form a single pBJ plasmid that contains both heavy and light chain genes. The pBJ clones were screened by Srf I/Not I digestion to confirm the presence of both antibody genes. The plasmid map for Chagas 10-745 Mu-Hu_pBJ clone 1 is shown in FIG. 5.

CHO cell line B3.2 acquired from the Abbott Bioresearch Center containing a deficient DHFR gene was used for transfection and stable antibody expression. CHO B3.2 cells were transfected with Chagas 10-745 Mu-Hu_pBJ clone 1 using calcium phosphate-mediated transfection. The transfected CHO cells were cultured for several weeks with media lacking thymidine to select for those cells that had incorporated the functional DHFR gene present in the pBJ plasmid. FACS was used to sort individual cells from the transfected pool into 96-well plates. An antigen-specific EIA was used to rank antibody production among the clones, and the highest producers were expanded and re-assayed. Clones were then weaned into serum-free media. The growth characteristics, antibody production and clonality of the clones were monitored. Chagas FP10 clone 10-745-3649 was sub-cloned by sorting individual cells into 96-well plates and then expanded to produce purified antibody.

Example 8

Cell Lines Producing Chimeric Anti-*T. cruzi* FRA mAbs (Prophetic Example)

Identification of Mouse $V_H$ and $V_L$ Sequences

Hybridoma cell line HBFRA (Example 4) is cultured in H—SFM to obtain ~5×10$^6$ cells for mRNA purification according to standard mRNA extraction protocols. The purified mRNA is used as a template with a mouse Ig primer set (Novagen (EMD Biosciences, Inc.)) for a RT-PCR reaction. Positive PCR products are observed from the heavy chain (H) primers and from the light chain (L) primers. All positive PCR products are gel-purified and cloned into pCR TOPO 2.1 TA vector (Invitrogen Corp., Carlsbad, Calif.). The plasmid DNA is purified from transformed bacterial cells and the $V_H$ or $V_L$ inserts are confirmed by EcoRI digestion for each RT-PCR reaction that generated appropriately sized products. The correct $V_H$ or $V_L$ gene sequence is selected after sequence alignments confirm a consensus sequence among the clones.

Cloning Murine $V_H$ and $V_L$ Genes into pBOS Vectors

A pair of PCR primers containing a partial Kappa signal sequence and an Nru I site on the 5'-primer, and a BsiW I site on the 3'-primer is used to amplify the mouse $V_L$ gene from TOPO. Additionally, a pair of primers containing a partial heavy chain signal sequence and an Nru I site on the 5'-primer, and Sal I site on 3'-primer is used to amplify the mouse $V_H$ gene from TOPO clone. The $V_L$ PCR product is digested with Nru I and BsiW I restriction enzymes and ligated into pBOS-hCk vector digested with the same enzymes. The $V_H$ PCR product is digested with Nru I and Sal I restriction enzymes and ligated into pBOS-hCg1 vector digested with the same enzymes. Plasmids from a number of transformed bacterial colonies are sequenced to confirm the presence of either the Chagas $V_H$ or $V_L$ gene in their respective vectors (Chagas $V_H$_pBOS-H and Chagas $V_L$_pBOS-L).

Chimeric mAb Production and Functional Confirmation

Endotoxin-free plasmid preparations of Chagas $V_H$_pBOS-H and Chagas $V_L$_pBOS-L are used for transient transfection into COS 7L cells by electroporation (GENE PULSER®, Bio-Rad) or other transfection method. The transfected cells are incubated at 37° C. in a 5% $CO_2$ incubator for about three days. The chimeric antibody produced by the COS 7L cells is harvested by centrifugation at 4000 rpm for 20 minutes and then purified using a protein A affinity column (POROS A; Applied Biosystems; Foster City, Calif.). To confirm activity, the harvested antibody is assayed by, for example using surface plasmon resonance on a BIACORE® instrument (Biacore (GE Healthcare)).

CHO Cell Line Stable Expression Vector Cloning

Chagas $V_H$_pBOS-H and Chagas $V_L$_pBOS-L are used to construct a plasmid to generate a stable, transfected CHO cell line. First, Srf I and Not I are used to isolate the $V_H$-CH and $V_L$-CL genes from the pBOS vectors; these fragments are then cloned into pBV or pJV vectors, respectively. The resulting pBV and pJV clones are analyzed by Srf I/Not I restriction enzyme digestion and sequenced to determine that the clones are correct. Second, the correct pBV or pJV clones are both digested with Pac I and Asc I, and the resulting $V_H$-CH and $V_L$-CL-containing DNA fragments are ligated to form a single pBJ plasmid that contains both heavy and light chain genes. The pBJ clones are screened by Srf I/Not I digestion to confirm the presence of both antibody genes, resulting in Chagas Mu-Hu_pBJ.

A CHO cell line, such as CHO B3.2, containing a deficient DHFR gene is used for transfection and stable antibody expression. CHO B3.2 cells are transfected with Chagas Mu-Hu_pBJ using calcium phosphate-mediated transfection or other transfection protocol. The transfected CHO cells are cultured for several weeks with media lacking thymidine to select for those cells that incorporate the functional DHFR gene present in the pBJ plasmid. FACS can be used to sort individual cells from the transfected pool into 96-well plates. An antigen-specific EIA can be used to rank antibody production among the clones, and the highest producers are expanded and re-assayed. Clones are then weaned into serum-free media. The growth characteristics, antibody production and clonality of the clones are monitored. If desired, cell line clones can be sub-cloned by sorting individual cells into 96-well plates and then expanded to produce purified antibody.

Example 9

Kinetics/Affinity Determination of Recombinant Chimeric Chagas Antibody for Chagas Antigen TcF The kinetics/affinity were determined using a high density, goat anti-human IgG Fc capture biosensor on a BIAcore 2000. The flow cells were first equilibrated with a running buffer composed of HBS-EP spiked with 6 g/L of Carboxymethyl-Dextran (hereinafter referred to as a "Running Buffer") (Fluka) and 6 g/L BSA for 5 minutes at flow rate of 10 μL/minutes. Next, recombinant chimeric anti-Chagas monoclonal antibody, namely, 9-638-132 (Pep2 epitope in TcF and FP6), 10-745-140 (FP10) and 12-392-150 (FP3), each diluted into Running Buffer, were injected over individual flow cells and captured by the biosensor with one flow cell left blank as a reference flow cell. The buffer flow rate was increased to 100 μL/minute and the flow cells were washed for 10 minutes prior to a 150 μL injection of the antigen at various concentrations from 0 to 100 nM in Running Buffer followed by Running Buffer alone for 60 to 360 seconds. The anti-human IgG capture biosensor was then regenerated with three 33 μL injections of 100 mM $H_3PO_4$ and the steps above were repeated until all concentrations of each Chagas antigen were tested in duplicate. The binding kinetics, association ($k_a$) and dissociation ($k_d$), were monitored for each antigen injection by sensorgrams and the kinetics/affinity were determined by Scrubber 2.0 software (BioLogic Software Pty Ltd., Australia). The interactions between the recombinant chimeric anti-Chagas monoclonal antibodies with the Pep2 epitope within the Chagas TcF antigen are shown below in Table 14.

TABLE 14

| Chimeric Chagas Ab | $k_a$ ($M^{-1}s^{-1}$) | $k_d$ ($s^{-1}$) | $K_D$ (M) |
|---|---|---|---|
| 9-638-132 | 4.0 × $10^6$ | 1.7 × $10^{-2}$ | 4.1 × $10^{-9}$ |
| 10-745-140 | No binding was observed. | | |
| 12-392-150 | | | |

Example 10

Kinetics/Affinity Determination of Recombinant Chimeric Chagas Antibody for Chagas Antigens FP3 and FP10

The kinetics/affinity were determined using a high density, anti-$His_4$ capture biosensor on a BIAcore 2000. The flow cells were first equilibrated with a Running Buffer (as defined above in Example 9) composed of HBS-EP buffer spiked with 1% BSA and 1% Tween 20 for 5 minutes at a flow rate 50 μL/minute. Next, Chagas antigens (each antigen contains a His$_6$ tag), namely FP10 and FP3, were each diluted into Running Buffer, injected over individual flow cells, and captured by the biosensor with one flow cell left blank as a reference flow cell. The buffer flow rate was increased to 100 μL/minute and the flow cells were washed for 5 minutes prior to a 150 μL injection of each of the recombinant Chimeric anti-Chagas monoclonal antibodies, namely, 9-638-132 (Pep2 epitope in TcF and FP6), 10-745-140 (FP10) and 12-392-150 (FP3), at various concentrations from 0 to 300 nM in Running Buffer followed by Running Buffer alone for 60 to 360 seconds. The anti-His$_4$ capture biosensor was then regenerated with two 35 μL injections of Gentle Ab/Ag Elution Buffer (Pierce) spiked with 2.5 mM H$_3$PO$_4$ and two 25 μL injections of 5 mM H$_3$PO$_4$ and the steps above were repeated until all concentrations of each Chimeric anti-Chagas antibody were tested in duplicate. The binding kinetics, association ($k_a$) and dissociation ($k_d$) were monitored for each antibody injection by sensorgrams and the kinetics/affinity were determined by Scrubber 2.0 software (BioLogic Software Pty Ltd., Australia). The interactions between the recombinant chimeric anti-Chagas monoclonal antibodies with the Chagas FP10 antigen are shown below in Table 15. The interactions between the recombinant chimeric anti-Chagas monoclonal antibodies with the Chagas FP3 antigen are shown below in Table 16.

TABLE 15

| Chimeric Chagas Ab | $k_a$ (M$^{-1}$s$^{-1}$) | $k_d$ (s$^{-1}$) | $K_D$ (M) |
|---|---|---|---|
| 9-638-132 | No binding was observed. | | |
| 10-745-140 | 1.2 × 10$^5$ | 3.6 × 10$^{-4}$ | 2.9 × 10$^{-9}$ |
| 12-392-150 | No binding was observed. | | |

TABLE 16

| Chimeric Chagas Ab | $k_a$ (M$^{-1}$s$^{-1}$) | $k_d$ (s$^{-1}$) | $K_D$ (M) |
|---|---|---|---|
| 9-638-132 | No binding was observed. | | |
| 10-745-140 | | | |
| 12-392-150 | 2.7 × 10$^6$ | 3.8 × 10$^{-4}$ | 1.4 × 10$^{-10}$ |

Example 11

Kinetics/Affinity Determination of Murine Chagas Antibody for Chagas Antigens

The kinetics/affinity were determined using a high density, rabbit anti-mouse IgG capture biosensor on a BIAcore 2000. The flow cells were first equilibrated with a Running Buffer composed of HBS-EP buffer spiked with 1% BSA, 1% Carboxymethyl-Dextran ("Running Buffer") (Fluka), and 0.1% Tween 20 at 5 μL/minute for 5 minutes. Next, each murine anti-Chagas antibody (namely, monoclonal antibodies (mAbs) 8-367-171 (FRA), 9-638-132 (Pep2 epitope in TcF and FP6), 10-745-140 (FP10) and 12-392-150 (FP3) diluted into Running Buffer, was injected over individual flow cells and captured by the biosensor. The buffer flow rate was increased to 60 μl/min and the flow cells were washed for 5 minutes prior to a 150 μL injection of Chagas antigen at various concentrations from 0 to 200 nM in Running Buffer followed by Running Buffer alone for 60 to 360 seconds. The flow rate was then changed to 10 μL/minute and the anti-mouse IgG capture biosensor was then regenerated with one 30 μL injection of 10 mM Glycine pH 1.7 and the steps above were repeated until all concentrations of each Chagas antigen were tested in duplicate. The binding kinetics, association ($k_a$) and dissociation ($k_d$) were monitored for each antigen injection by sensorgrams and the kinetics/affinity were determined by Scrubber 2.0 software (BioLogic Software Pty Ltd., Australia).

For Chagas antigens FRA, FP6, TcF, and FP3, the flow cell containing anti-Chagas mAb 10-745-140 was used as the reference flow cell. The flow cell containing anti-Chagas mAb 9-638-132 was used as the reference flow cell for Chagas antigen FP10. The interaction between the monoclonal anti-Chagas antibodies with the Chagas FRA antigen itself is shown below in Table 17. The interaction between the monoclonal anti-Chagas antibodies with the FRA and the Chagas PEP2 epitope of the Chagas FP6 antigen is shown below in Table 18. The interaction between the monoclonal anti-Chagas antibodies with the Chagas PEP2 epitope of the Chagas TcF antigen is shown below in Table 19. The interaction between the monoclonal anti-Chagas antibodies with the Chagas FP10 antigen is shown below in Table 20. The interaction between the monoclonal anti-Chagas antibodies with the Chagas FP3 antigen is shown below in Table 21.

TABLE 17

| Murine Chagas Ab | $k_a$ (M$^{-1}$s$^{-1}$) | $k_d$ (s$^{-1}$) | $K_D$ (M) |
|---|---|---|---|
| 8-367-171 | 3.6 × 10$^6$ | 1.3 × 10$^{-1}$ | 3.7 × 10$^{-8}$ |
| 9-638-132 | No binding was observed | | |
| 10-745-140 | | | |
| 12-392-150 | | | |

TABLE 18

| Murine Chagas Ab | $k_a$ (M$^{-1}$s$^{-1}$) | $k_d$ (s$^{-1}$) | $K_D$ (M) |
|---|---|---|---|
| 8-367-171 | 1.5 × 10$^6$ | 7.9 × 10$^{-3}$ | 5.2 × 10$^{-9}$ |
| 9-638-132 | Binding was observed, but could not be fit to 1:1 model | | |
| 10-745-140 | No binding was observed | | |
| 12-392-150 | | | |

TABLE 19

| Murine Chagas Ab | $k_a$ (M$^{-1}$s$^{-1}$) | $k_d$ (s$^{-1}$) | $K_D$ (M) |
|---|---|---|---|
| 8-367-171 | No binding was observed | | |
| 9-638-132 | 2.1 × 10$^6$ | 1.2 × 10$^{-2}$ | 5.7 × 10$^{-9}$ |
| 10-745-140 | No binding was observed | | |
| 12-392-150 | | | |

TABLE 20

| Murine Chagas Ab | $k_a$ (M$^{-1}$s$^{-1}$) | $k_d$ (s$^{-1}$) | $K_D$ (M) |
|---|---|---|---|
| 8-367-171 | No binding was observed | | |
| 9-638-132 | | | |
| 10-745-140 | 1.1 × 10$^5$ | 2.2 × 10$^{-4}$ | 1.9 × 10$^{-9}$ |
| 12-392-150 | No binding was observed | | |

TABLE 21

| Murine Chagas Ab | $k_a$ (M$^{-1}$s$^{-1}$) | $k_d$ (s$^{-1}$) | $K_D$ (M) |
|---|---|---|---|
| 8-367-171 | No binding was observed | | |
| 9-638-132 | | | |
| 10-745-140 | | | |
| 12-392-150 | 5.6 × 10$^5$ | 5 × 10$^{-5}$ | 8 × 10$^{-11}$ |

One skilled in the art would readily appreciate that the present disclosure is well adapted to carry out the objects and obtain the ends and advantages mentioned, as well as those inherent therein. The molecular complexes and the methods, procedures, treatments, molecules, specific compounds described herein are presently representative of preferred embodiments, are exemplary, and are not intended as limitations on the scope of the disclosure. It will be readily apparent to one skilled in the art that varying substitutions and modifications may be made to the disclosure disclosed herein without departing from the scope and spirit of the disclosure.

All patents and publications mentioned in the specification are indicative of the levels of those skilled in the art to which the disclosure pertains. All patents and publications are herein incorporated by reference to the same extent as if each individual publication was specifically and individually indicated to be incorporated by reference.

What is claimed is:

1. An immunodiagnostic reagent comprising an isolated, monoclonal antibody that specifically binds to a diagnostically relevant region of a *T. cruzi* polypeptide, wherein said monoclonal antibody comprises a variable light ($V_L$) region comprising an amino acid sequence as set forth in SEQ ID NO:14 and a variable heavy ($V_H$) region comprising an amino acid sequence as set forth in SEQ ID NO:16.

2. The immunodiagnostic reagent according to claim 1, wherein said monoclonal antibody is
   an antibody that specifically binds to an epitope comprised by an amino acid sequence as set forth in SEQ ID NO.:4.

3. An isolated, monoclonal antibody comprising a variable light ($V_L$) region comprising an amino acid sequence as set forth in SEQ ID NO:14 and a variable heavy ($V_H$) region comprising an amino acid sequence as set forth in SEQ ID NO:16.

4. The isolated, monoclonal antibody of claim 3, wherein said monoclonal antibody is
   an antibody that specifically binds to an epitope comprised by an amino acid sequence as set forth in SEQ ID NO.:4.

5. An isolated antibody expressed by a cell line deposited with the American Type Tissue Collection and identified by patent deposit designation PTA-8138.

6. An isolated antibody expressed by a cell line deposited with the American Type Tissue Collection and identified by patent deposit designation PTA-8137.

7. An isolated polypeptide comprising a portion of a monoclonal antibody which binds to a diagnostically relevant region of a *T. cruzi* polypeptide, wherein said monoclonal antibody comprises
   a variable light ($V_L$) region comprising an amino acid sequence as set forth in SEQ ID NO.:14 and a variable heavy ($V_H$) region comprising an amino acid sequence as set forth in SEQ ID NO.:16.

8. A cell line that expresses a monoclonal antibody that specifically binds to a diagnostically relevant region of a *T. cruzi* polypeptide, wherein said cell line is PTA-8137 or PTA-8138.

9. A method of detecting a *T. cruzi* antigen comprising the steps of:
   (a) contacting a test sample suspected of containing a *T. cruzi* antigen with the immunodiagnostic reagent of claim 1 under conditions that allow formation of antibody:antigen complexes; and
   (b) detecting presence of any antibody:antigen complexes formed, presence of said complexes indicating presence of said *T. cruzi* antigen.

10. A method of detecting a *T. cruzi* antigen comprising the steps of:
- (a) contacting a test sample suspected of containing a *T. cruzi* antigen with the immunodiagnostic reagent of claim 1 under conditions that allow formation of antibody:antigen complexes; and
- (b) contacting said antibody:antigen complexes with a conjugate comprising an antibody attached to a detectable label, for a time and under conditions sufficient for said antibody of said conjugate to bind to said antigen of said antibody:antigen complexes and to allow for formation of antibody:antigen:conjugate complexes; and
- (c) detecting a signal generated by said label, wherein presence of said signal indicates detection of said *T. cruzi* antigen.

11. A diagnostic kit for the detection of *T. cruzi* antigen comprising said immunodiagnostic reagent of claim 1.

* * * * *